US007262043B2

(12) United States Patent
Anderson et al.

(10) Patent No.: US 7,262,043 B2
(45) Date of Patent: *Aug. 28, 2007

(54) β-SECRETASE ENZYME COMPOSITIONS AND METHODS

(75) Inventors: John P. Anderson, San Francisco, CA (US); Guriqbal Basi, Palo Alto, CA (US); Minh Tam Doan, Hayward, CA (US); Normand Frigon, Milbrae, CA (US); Varghese John, San Francisco, CA (US); Michael Power, Fremont, CA (US); Sukanto Sinha, San Francisco, CA (US); Gwen Tatsuno, Oakland, CA (US); Jay Tung, Belmont, CA (US); Shuwen Wang, Hershey, PA (US); Lisa McConlogue, Burlingame, CA (US)

(73) Assignee: Elan Pharmaceuticals, Inc., South San Francisco, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 11/090,399

(22) Filed: Mar. 25, 2005

(65) Prior Publication Data

US 2005/0196839 A1     Sep. 8, 2005

Related U.S. Application Data

(63) Continuation of application No. 09/723,722, filed on Nov. 28, 2000, now Pat. No. 7,115,410, which is a continuation of application No. 09/501,708, filed on Feb. 10, 2000, now abandoned, which is a continuation-in-part of application No. 09/471,669, filed on Dec. 24, 1999, said application No. 09/501,708 is a continuation-in-part of application No. 09/471,669, filed on Dec. 24, 1999.

(60) Provisional application No. 60/139,172, filed on Jun. 15, 1999, provisional application No. 60/119,571, filed on Feb. 10, 1999.

(51) Int. Cl.
*C12N 9/64* (2006.01)
*C12P 21/06* (2006.01)

(52) U.S. Cl. ..................... 435/226; 435/69.1
(58) Field of Classification Search ............... 435/226, 435/69.1, 325, 320.1; 536/23.2
See application file for complete search history.

(56) References Cited

U.S. PATENT DOCUMENTS

| 5,424,205 | A | 6/1995 | Dovey et al. |
|---|---|---|---|
| 5,455,169 | A | 10/1995 | Mullan |
| 5,593,846 | A | 1/1997 | Schenk et al. |
| 5,733,768 | A | 3/1998 | Dixon et al. |
| 5,744,346 | A | 4/1998 | Chrysler et al. |
| 5,750,349 | A | 5/1998 | Suzuki et al. |
| 5,766,846 | A | 6/1998 | Schlossmacher et al. |
| 5,795,963 | A | 8/1998 | Mullan |
| 5,837,672 | A | 11/1998 | Schenk et al. |
| 5,849,560 | A | 12/1998 | Abraham |
| 5,863,756 | A | 1/1999 | Barr et al. |
| 5,877,015 | A | 3/1999 | Hardy et al. |
| 5,942,400 | A | 8/1999 | Anderson et al. |
| 6,025,180 | A | 2/2000 | Powell et al. |
| 6,162,630 | A | 12/2000 | Powell et al. |
| 6,211,428 | B1 | 4/2001 | Singh et al. |
| 6,221,645 | B1 | 4/2001 | Chrysler et al. |
| 6,245,884 | B1 | 6/2001 | Hook |
| 6,245,964 | B1 | 6/2001 | McConlogue et al. |
| 6,313,268 | B1 | 11/2001 | Hook |
| 6,319,489 | B1 | 11/2001 | Powell et al. |
| 6,319,689 | B1 | 11/2001 | Powell et al. |
| 6,329,163 | B1 | 12/2001 | Anderson et al. |
| 6,358,725 | B1 | 3/2002 | Christie et al. |
| 6,361,975 | B1 | 3/2002 | Christie et al. |
| 6,420,534 | B1 | 7/2002 | Gurney et al. |
| 6,440,698 | B1 | 8/2002 | Gurney et al. |
| 6,500,667 | B1 | 12/2002 | Gurney et al. |
| 6,627,739 | B1 | 9/2003 | Anderson |
| 6,699,671 | B1 | 3/2004 | Gurney et al. |

(Continued)

FOREIGN PATENT DOCUMENTS

EP     848 062 A2     6/1998

(Continued)

OTHER PUBLICATIONS

U.S. Appl. No. 10/817,979, Gurney et al.

(Continued)

*Primary Examiner*—Rebecca E. Prouty
*Assistant Examiner*—Malgorzata A. Walicka
(74) *Attorney, Agent, or Firm*—Townsend and Townsend and Crew, LLP

(57) ABSTRACT

Disclosed are various forms of an active, isolated β-secretase enzyme in purified and recombinant form. This enzyme is implicated in the production of amyloid plaque components which accumulate in the brains of individuals afflicted with Alzheimer's disease. Recombinant cells that produce this enzyme either alone or in combination with some of its natural substrates (β-APPwt and β-APPsw) are also disclosed, as are antibodies directed to such proteins. These compositions are useful for use in methods of selecting compounds that modulate β-secretase. Inhibitors of β-secretase are implicated as therapeutics in the treatment of neurodegenerative diseases, such as Alzheimer's disease.

4 Claims, 48 Drawing Sheets

U.S. PATENT DOCUMENTS

| | | | |
|---|---|---|---|
| 6,706,485 | B1 | 3/2004 | Gurney et al. |
| 6,727,074 | B2 | 4/2004 | Gurney et al. |
| 6,737,510 | B1 | 5/2004 | Gurney et al. |
| 6,753,163 | B2 | 6/2004 | Gurney et al. |
| 6,790,610 | B2 | 9/2004 | Gurney et al. |
| 6,797,487 | B2 | 9/2004 | Gurney et al. |
| 6,825,023 | B1 | 11/2004 | Gurney et al. |
| 6,828,117 | B2 | 12/2004 | Gurney et al. |
| 6,835,565 | B1 | 12/2004 | Gurney et al. |
| 6,844,148 | B1 | 1/2005 | Gurney et al. |
| 6,852,482 | B1 | 2/2005 | Gurney et al. |
| 2001/0021391 | A1 | 9/2001 | Gurney et al. |
| 2002/0037315 | A1 | 3/2002 | Gurney et al. |
| 2002/0081634 | A1 | 6/2002 | Gurney et al. |
| 2004/0043408 | A1 | 3/2004 | Gurney et al. |
| 2004/0048303 | A1 | 3/2004 | Gurney et al. |
| 2004/0166507 | A1 | 8/2004 | Gurney et al. |
| 2004/0234976 | A1 | 11/2004 | Gurney et al. |

FOREIGN PATENT DOCUMENTS

| | | |
|---|---|---|
| EP | 855 442 A2 | 7/1998 |
| EP | 855 444 A2 | 7/1998 |
| EP | 1 445 263 A1 | 8/2004 |
| GB | 2 364 059 B | 1/2004 |
| GB | 2 389 113 B | 2/2004 |
| GB | 2 389 114 B | 2/2004 |
| GB | 2 389 182 B | 2/2004 |
| WO | WO96/20725 A2 | 7/1996 |
| WO | WO96/31122 A1 | 10/1996 |
| WO | WO96/40885 A2 | 12/1996 |
| WO | WO97/47314 | 12/1997 |
| WO | WO98/11236 | 3/1998 |
| WO | WO98/13488 | 4/1998 |
| WO | WO98/21589 | 5/1998 |
| WO | WO98/26059 | 6/1998 |
| WO | WO98/37226 A1 | 8/1998 |
| WO | WO99/31236 A2 | 6/1999 |
| WO | WO99/34004 A2 | 8/1999 |
| WO | WO99/46281 A2 | 9/1999 |
| WO | WO99/64587 A1 | 12/1999 |
| WO | WO 00/17369 A2 | 3/2000 |
| WO | WO 00/23576 A2 | 4/2000 |
| WO | WO 00/47618 A3 | 8/2000 |
| WO | WO 00/56871 A2 | 9/2000 |
| WO | WO 00/58479 A1 | 10/2000 |
| WO | WO 00/69262 A1 | 11/2000 |
| WO | WO 01/68266 A1 | 11/2000 |
| WO | WO 01/00663 A2 | 1/2001 |
| WO | WO 01/00665 A2 | 1/2001 |
| WO | WO 01/23533 A2 | 4/2001 |
| WO | WO 01/29563 A1 | 4/2001 |
| WO | WO 01/31054 A1 | 5/2001 |
| WO | WO 01/36600 A1 | 5/2001 |
| WO | WO 01/38487 A2 | 5/2001 |
| WO | WO 01/49097 A2 | 7/2001 |
| WO | WO 01/49098 A2 | 7/2001 |
| WO | WO 01/50829 A2 | 7/2001 |

OTHER PUBLICATIONS

U.S. Appl. No. 10/477,076, Gurney et al.
U.S. Appl. No. 09/668,314, Gurney et al.
U.S. Appl. No. 09/548,370, Gurney et al.
U.S. Appl. No. 09/548,369, Gurney et al.
U.S. Appl. No. 09/548,365, Gurney et al.
U.S. Appl. No. 09/404,133, Gurney et al.
U.S. Appl. No. 09/277,229, Citron et al.
U.S. Appl. No. 60/210,292, Hong et al.
U.S. Appl. No. 60/178,368, Lin et al.
U.S. Appl. No. 60/177,836, Lin et al.
U.S. Appl. No. 60/169,232, Gurney et al.
U.S. Appl. No. 60/168,060, Lin et al.
U.S. Appl. No. 60/155,493, Gurney et al.
U.S. Appl. No. 60/141,363, Lin et al.
U.S. Appl. No. 60/139,172, Anderson et al.
U.S. Appl. No. 60/119,571, Basi et al.
U.S. Appl. No. 60/114,408, Basi et al.
U.S. Appl. No. 60/101,594, Gurney et al.
Baldwin et al., "Crystal structures of native and inhibited forms of human cathepsin D: Implications for lysosomal targeting and drug design," *PNAS*, 90:6796-6800 (1993).
Bork, P., "Powers and Pitfalls in Sequence Analysis: The 70% Hurdle," *Genome Research*, 10:398-400 (2000).
Broun et al., "Catalytic Plasticity of Fatty Acid Modification Enzymes Underlying Chemical Diversity," *Science*, 282:131-133 (1998).
Brown et al., "Evaluation of Cathepsins D and G and EC 3.4.24.15 as Candidate β-Secretase Proteases Using Peptide and Amyloid Precursor Protein Substrates," *Journal of Neurochemistry*, 66:2436-2445 (1996).
Chevallier et al., "Cathepsin D displays in vitro β-secretase-like specificity," *Brain Research*, 750:11-19 (1997).
Chyung et al., "Novel β-Secretase Cleavage of β-Amyloid Precursor Protein in the Endoplasmic Reticulum/Intermediate Compartment of NT2N Cells," *Journal of Cell Biology*, 138:671-680 (1997).
Das et al., "Estrogenic responses in estrogen receptor-α deficient mice reveal a distinct estrogen signaling pathway," *PNAS*, 94:12786-12791 (1997).
Declaration of Michael Bienkowski, Ph.D. in U.S. Appl. No. 09/548,368.
Dennis et al., "Kunitz Domain Inhibitors of Tissue Factor-Factor VIIa," *J. Biol. Chem.*, 269(35):22129-22136 (1994).
Diedrich et al., "Nucleotide sequence of a cDNA encoding mouse cathepsin D," *Nucleic Acids Research*, 18:7184 (1990).
Elan Corporation, plc and Pharmacia Corporation announce research collaboration, News Aug. 9, 2000, www.elancorp.com.
Examination Report for United Kingdom Application 00121314.9 dated Nov. 1, 2002.
Examination Report for United Kingdom Application 00121314.9 dated Jul. 21, 2003.
Examination Report for United Kingdom Application 00121314.9 dated Oct. 30, 2003.
Examination Report for United Kingdom Application 0318112.0 dated Nov. 19, 2003.
Search and Examination Report for United Kingdom Application 0318112.0 dated Sep. 24, 2003.
Search and Examination Report for United Kingdom Application 0318107.0 dated Sep. 25, 2003.
Search and Examination Report for United Kingdom Application 0318113.8 dated Sep. 25, 2003.
Examination Report for United Kingdom Application 0318113.8 dated Nov. 19, 2003.
Examination Report for European Application 00919298.0 dated Oct. 30, 2003.
Search Report for European Application 04006991.6 dated Jun. 11, 2004.
Examination Report for New Zealand Application 534876 dated Aug. 27, 2004.
Examination Report for European Application 00919298.0 dated Sep. 20, 2004.
International Preliminary Examination Report for PCT application PCT/US00/03819 dated Sep. 4, 2002.
Evin et al., "Alzheimer's disease amyloid precursor protein (βAPP): proteolytic processing, secretases and βA4 amyloid production," *Amyloid: Int. J. Exp. Clin. Invest.* 1:263-280 (1994).
Haass et al., "Amyloid β-peptide is Produced by Cultured Cells During Normal Metabolism," *Nature*, 359:322-325 (1992).
Haass et al., "The Swedish Mutation Causes Early-Onset Alzheimer's Disease by β-Secretase Cleavage Within the Secretory Pathway," *Nature Medicine*, 12:1291-1296 (1995).
Haass et al., "β-Amyloid Peptide and 3-kDa Fragment are Derived by Distinct Cellular Mechanisms," *Journal of Biochemistry*, 268:3021-3024 (1993).

Hardy, J., "Framing beta-amyloid," *Nature Genetics*, 1(4):233-234 (1992).

Hirosawa et al., "Characterization of cDNA Clones Selected by the GeneMark Analysis from Size-Fractionated cDNA Libraries From Human Brain," *DNA Res.*, 6(5):329-336 (1999).

Hussain et al., "Identification of a Novel Aspartic Protease (Asp 2) as β-Secretase," *Molecular and Cellular Neuroscience*, 14:419-427 (1999).

Jackson et al., "The p47[phox] Mouse Knock-Out Model of Chronic Granulomatous Disease," *J. Exp. Med.*, 182:751-758 (1995).

Kang et al., "The Precursor of Alzheimer's Disease Amyloid A4 Protein Resembles a Cell-Surface Receptor," *Nature*, 325:733-736 (1987).

Kick et al., "Structure-based design and combinatorial chemistry yield low nanomolar inhibitors of cathepsin D," *Chem. & Biol.*, 4:297-307 (1997).

Kitaguchi et al., "Novel Precursor of Alzheimer's Disease Amyloid Protein Shows Protease Inhibitory Activity," *Nature*, 331:530-532 (1988).

Knops et al., "Cell-type and Amyloid Precursor Protein-type Specific Inhibition of Aβ Release by Bafilomycin A1, a Selective Inhibitor of Vacuolar ATPases," *Journal of Biological Chemistry*, 270:2419-2422 (1995).

Koo et al., "Evidence that Production and Release of Amyloid β-Protein Involves the Endocytic Pathway," *Journal of Biological Chemistry*, 269:17386-17389 (1994).

Kristie, T. M., "The Mouse Homologue of the Human Transcription Factor C1 (Host Cell Factor)," *J. Biol. Chem.*, 272(42):26749-26755 (1997).

Li et al., "Cloning and Characterization of Three New Murine Genes Encoding Short Homologues of RNase P RNA*," *J. Biol. Chem.*, 270(42):25281-25285 (1995).

Majer et al., "Structure-based subsite specificity mapping of human cathepsin D using statine-based inhibitors," *Protein Science*, 6:1458-1466 (1997).

Mullan et al., "A Pathogenic Mutation for Probable Alzheimer's Disease in the APP Gene at the N-Terminus of β-Amyloid," *Nature Genetics*, 1:345-347 (1992).

Office Action dated May 6, 2002 in U.S. Appl. No. 09/548,368.

PCT Search report for PCT/US99/20881.

PCT Search report for PCT/US00/03819.

Ponte et al., "A New A4 Amyloid mRNA Contains a Domain Homologous to Serine Proteinase Inhibitors," *Nature*, 331:525-527 (1988).

Raabe et al., "Knockout of the abetalipoproteinemia gene in mice: Reduced lipoprotein secretion in heterozygotes and embryonic lethality in homozygotes," *PNAS*, 95:8686-8691 (1998).

Saftig et al., "Amyloidogenic Processing of Human Amyloid Precursor Protein in Hippocampal Neurons Devoid of Cathepsin D," *Journal of Biological Chemistry*, 271:27241-27244 (1996).

Schechter et al., "On the size of the active site in proteases. I. Papain," *Biochemical and Biophysical Research Communications*, 27:157-162 (1967).

Seubert et al., "Secretion of β-amyloid Precursor Protein Cleaved at the Amino Terminus of the β-amyloid Peptide," *Nature*, 361:260-263 (1993).

Sinha et al., "Purification and Cloning of Amyloid Precursor Protein β-Secretase from Human Brain," *Nature*, 402:537-540 (1999).

Sun et al., "Gene Structure, Chromosomal Localization, and Expression of the Murine Homologue of Human Proteinase Inhibitor 6 (PI-6) Suggests Divergence of PI-6 from the Ovalbumin Serpins*," *J. Biol. Chem.*, 270(27): 16089-16096 (1995).

Szecsi, "The Aspartic Proteases," *Scand. J. Clin. Lab. Invest.*, 52 (suppl. 210): 5-22 (1992).

Tanzi et al., "Protease Inhibitor Domain Encoded by an Amyloid Protein Precursor mRNA Associated with Alzheimer's Disease," *Nature*, 331:528-530 (1988).

Thompson et al., "Expression and characterization of human β-Secretase from candidates metalloendopeptidase MP78 and cathepsin D in βAPP-overexpressing cells," *Molecular Brain Research*, 48(2):206-214 (1997).

Umans et al., "Targeted Inactivation of the Mouse $_{a2}$-Macroglobulin Gene*," *J. Biol. Chem.*, 270(34):19778-19785 (1995).

Van de Loo et al., "An oleate 12-hydroxylase from *Ricinus communis* L. is a fatty acyl desaturase homolog," *PNBS*, 92:6743-6747 (1995).

Vasser et al., "β-secretase Cleavage of Alzheimer's Amyloid Precursor Protein by the Transmembrane Aspartic Protease BACE," *Science*, 286(5440):735-741 (1999).

Yan et al., "Membrane-anchored Aspartyl Protease with Alzheimer's Disease β-Secretase Activity," *Nature*, 402:533-537 (1999).

Young et al., "HIV-1 Protease Inhibitors Based on Hydroxyethylene Dipeptide Isosteres: An Investigation into the Role of the $P_1$ Side Chain on Structure-Activity," *J. Med. Chem.*, 35:1702-1709 (1992).

Zhao et al., "β-Secretase Processing of the β-Amyloid Precursor Protein in Transgenic Mice Is Efficient in Neurons but Inefficient in Astrocytes," *Journal of Biological Chemistry*, 271:31407-31411 (1996).

```
ATGGCCCAAGCCCTGCCCTGGCTCCTGCTGTGGATGGGCGCGGGAG
TGCTGCCTGCCCACGGCACCCAGCACGGCATCCGGCTGCCCCTGCG
CAGCGGCCTGGGGGGCGCCCCCTGGGGCTGCGGCTGCCCCGGGA
GACCGACGAAGAGCCCGAGGAGCCCGGCCGGAGGGGCAGCTTTGT
GGAGATGGTGGACAACCTGAGGGGCAAGTCGGGGCAGGGCTACTAC
GTGGAGATGACCGTGGGCAGCCCCCGCAGACGCTCAACATCCTGG
TGGATACAGGCAGCAGTAACTTTGCAGTGGGTGCTGCCCCCACCC
CTTCCTGCATCGCTACTACCAGAGGCAGCTGTCCAGCACATACCGGG
ACCTCCGGAAGGGTGTGTATGTGCCCTACACCCAGGGCAAGTGGGA
AGGGGAGCTGGGCACCGACCTGGTAAGCATCCCCCATGGCCCCAAC
GTCACTGTGCGTGCCAACATTGCTGCCATCACTGAATCAGACAAGTT
CTTCATCAACGGCTCCAACTGGGAAGGCATCCTGGGGCTGGCCTATG
CTGAGATTGCCAGGCCTGACGACTCCCTGGAGCCTTTCTTTGACTCT
CTGGTAAAGCAGACCCACGTTCCCAACCTCTTCTCCCTGCAGCTTTG
TGGTGCTGGCTTCCCCCTCAACCAGTCTGAAGTGCTGGCCTCTGTCG
GAGGGAGCATGATCATTGGAGGTATCGACCACTCGCTGTACACAGGC
AGTCTCTGGTATACACCCATCCGGCGGGAGTGGTATTATGAGGTGAT
CATTGTGCGGGTGGAGATCAATGGACAGGATCTGAAAATGGACTGCA
AGGAGTACAACTATGACAAGAGCATTGTGGACAGTGGCACCACCAAC
CTTCGTTTGCCCAAGAAAGTGTTTGAAGCTGCAGTCAAATCCATCAAG
GCAGCCTCCTCCACGGAGAAGTTCCCTGATGGTTTCTGGCTAGGAGA
GCAGCTGGTGTGCTGGCAAGCAGGCACCACCCCTTGGAACATTTTCC
CAGTCATCTCACTCTACCTAATGGGTGAGGTTACCAACCAGTCCTTCC
GCATCACCATCCTTCCGCAGCAATACCTGCGGCCAGTGGAAGATGTG
GCCACGTCCCAAGACGACTGTTACAAGTTTGCCATCTCACAGTCATC
CACGGGCACTGTTATGGGAGCTGTTATCATGGAGGGCTTCTACGTTG
TCTTTGATCGGGCCCGAAAACGAATTGGCTTTGCTGTCAGCGCTTGC
CATGTGCACGATGAGTTCAGGACGGCAGCGGTGGAAGGCCCTTTTG
TCACCTTGGACATGGAAGACTGTGGCTACAACATTCCACAGACAGAT
GAGTCAACCCTCATGACCATAGCCTATGTCATGGCTGCCATCTGCGC
CCTCTTCATGCTGCCACTCTGCCTCATGGTGTGTCAGTGGCGCTGCC
TCCGCTGCCTGCGCCAGCAGCATGATGACTTTGCTGATGACATCTCC
CTGCTGAAG
```

FIG. 1A

```
CCATGCCGGCCCCTCACAGCCCCGCCGGGAGCCCGAGCCCGCTGCCCAGG
CTGGCCGCCGCSGTGCCGATGTAGCGGGCTCCGGATCCCAGCCTCTCCCCT
GCTCCCGTGCTCTGCGGATCTCCCTGACCGCTCTCCACAGCCCGGACCCG
GGGGCTGGCCCAGGGCCCTGCAGGCCCTGGCGTCCTGATGCCCCAAGCT
CCCTCTCCTGAGAAGCCACCAGCACCACCCAGACTTGGGGGCAGGCGCCA
GGGACGGACGTGGGCCAGTGCGAGCCCAGAGGGCCCGAAGGCCGGGGCC
CACCATGGCCCAAGCCCTGCCCTGGCTCCTGCTGTGGATGGGCGCGGGAG
TGCTGCCTGCCCACGGCACCCAGCACGGCATCCGGCTGCCCCTGCGCAGC
GGCCTGGGGGGCGCCCCCTGGGGCTGCGGCTGCCCCGGGAGACCGACG
AAGAGCCCGAGGAGCCCGGCCGGAGGGGCAGCTTTGTGGAGATGGTGGAC
AACCTGAGGGGCAAGTCGGGGCAGGGCTACTACGTGGAGATGACCGTGGG
CAGCCCCCCGCAGACGCTCAACATCCTGGTGGATACAGGCAGCAGTAACTT
TGCAGTGGGTGCTGCCCCCACCCCTTCCTGCATCGCTACTACCAGAGGCA
GCTGTCCAGCACATACCGGGACCTCCGGAAGGGTGTGTATGTGCCCTACAC
CCAGGGCAAGTGGGAAGGGGAGCTGGGCACCGACCTGGTAAGCATCCCCC
ATGGCCCAACGTCACTGTGCGTGCCAACATTGCTGCCATCACTGAATCAGA
CAAGTTCTTCATCAACGGCTCCAACTGGGAAGGCATCCTGGGGCTGGCCTAT
GCTGAGATTGCCAGGCCTGACGACTCCCTGGAGCCTTTCTTTGACTCTCTGG
TAAAGCAGACCCACGTTCCCAACCTCTTCTCCCTGCAGCTTTGTGGTGCTGG
CTTCCCCCTCAACCAGTCTGAAGTGCTGGCCTCTGTCGGAGGGAGCATGAT
CATTGGAGGTATCGACCACTCGCTGTACACAGGCAGTCTCTGGTATACACCC
ATCCGGCGGGAGTGGTATTATGAGGTGATCATTGTGCGGGTGGAGATCAAT
GGACAGGATCTGAAAATGGACTGCAAGGAGTACAACTATGACAAGAGCATTG
TGGACAGTGGCACCACCAACCTTCGTTTGCCCAAGAAAGTGTTTGAAGCTGC
AGTCAAATCCATCAAGGCAGCCTCCTCCACGGAGAAGTTCCCTGATGGTTTC
TGGCTAGGAGAGCAGCTGGTGTGCTGGCAAGCAGGCACCACCCCTTGGAAC
ATTTTCCCAGTCATCTCACTCTACCTAATGGGTGAGGTTACCAACCAGTCCTT
CCGCATCACCATCCTTCCGCAGCAATACCTGCGGCCAGTGGAAGATGTGGC
CACGTCCCAAGACGACTGTTACAAGTTTGCCATCTCACAGTCATCCACGGGC
ACTGTTATGGGAGCTGTTATCATGGAGGGCTTCTACGTTGTCTTTGATCGGG
CCCGAAAACGAATTGGCTTTGCTGTCAGCGCTTGCCATGTGCACGATGAGTT
CAGGACGGCAGCGGTGGAAGGCCCTTTTGTCACCTTGGACATGGAAGACTG
TGGCTACAACATTCCACAGACAGATGAGTCAACCCTCATGACCATAGCCTAT
GTCATGGCTGCCATCTGCGCCCTCTTCATGCTGCCACTCTGCCTCATGGTGT
GTCAGTGGCGCTGCCTCCGCTGCCTGCGCCAGCAGCATGATGACTTTGCTG
ATGACATCTCCCTGCTGAAGTGAGGAGGCCCATGGGCAGAAGATAGAGATT
CCCCTGGACCACACCTCCGTGGTTCACTTTGGTCACAAGTAGGAGACACAGA
TGGCACCTGTGGCCAGAGCACCTCAGGACCCTCCCCACCCACCAAATGCCT
CTGCCTTGATGGAGAAGGAAAAGGCTGGCAAGGTGGGTTCCAGGGACTGTA
CCTGTAGGAAACAGAAAAGAGAAGAAAGAAGCACTCTGCTGGCGGGAATAC
TCTTGGTCACCTCAAATTTAAGTCGGGAAATTCTGCTGCTTGAAACTTCAGCC
CTGAACCTTTGTCCACCATTCCTTTAAATTCTCCAACCCAAAGTATTCTTCTTT
TCTTAGTTTCAGAAGTACTGGCATCACACGCAGGTTACCTTGGCGTGTGTCC
CTGTGGTACCCTGGCAGAGAAGAGACCAAGCTTGTTTCCCTGCTGGCCAAA
GTCAGTAGGAGAGGATGCACAGTTTGCTATTTGCTTTAGAGACAGGGACTGT
ATAAACAAGCCTAACATTGGTGCAAAGATTGCCTCTTGAATT
```

FIG. 1B

MAQALPWLLLWMGAGVLPAHGTQHGIRLPLRSGLGGAPLGLRL
PRETDEEPEEPGRRGSFVEMVDNLRGKSGQGYYVEMTVGSPP
QTLNILVDTGSSNFAVGAAPHPFLHRYYQRQLSSTYRDLRKGVY
VPYTQGKWEGELGTDLVSIPHGPNVTVRANIAAITESDKFFINGS
NWEGILGLAYAEIARPDDSLEPFFDSLVKQTHVPNLFSLQLCGAG
FPLNQSEVLASVGGSMIIGGIDHSLYTGSLWYTPIRREWYYEVIIV
RVEINGQDLKMDCKEYNYDKSIVDSGTTNLRLPKKVFEAAVKSIK
AASSTEKFPDGFWLGEQLVCWQAGTTPWNIFPVISLYLMGEVTN
QSFRITILPQQYLRPVEDVATSQDDCYKFAISQSSTGTVMGAVIM
EGFYVVFDRARKRIGFAVSACHVHDEFRTAAVEGPFVTLDMEDC
GYNIPQTDESTLMTIAYVMAAICALFMLPLCLMVCQWRCLRCLR
QQHDDFADDISLLK

FIG. 2A

ETDEEPEEPGRRGSFVEMVDNLRGKSGQGYYVEMTVGSPPQT
LNILVDTGSSNFAVGAAPHPFLHRYYQRQLSSTYRDLRKGVYVP
YTQGKWEGELGTDLVSIPHGPNVTVRANIAAITESDKFFINGSNW
EGILGLAYAEIARPDDSLEPFFDSLVKQTHVPNLFSLQLCGAGFP
LNQSEVLASVGGSMIIGGIDHSLYTGSLWYTPIRREWYYEVIIVRV
EINGQDLKMDCKEYNYDKSIVDSGTTNLRLPKKVFEAAVKSIKAA
SSTEKFPDGFWLGEQLVCWQAGTTPWNIFPVISLYLMGEVTNQ
SFRITILPQQYLRPVEDVATSQDDCYKFAISQSSTGTVMGAVIME
GFYVVFDRARKRIGFAVSACHVHDEFRTAAVEGPFVTLDMEDC
GYNIPQTDESTLMTIAYVMAAICALFMLPLCLMVCQWRCLRCLR
QQHDDFADDISLLK

FIG. 2B

MAQALPWLLLWMGAGVLPAHGTQHGIRLPLRSGLGGAPLGLRL
PRETDEEPEEPGRRGSFVEMVDNLRGKSGQGYYVEMTVGSPP
QTLNILVDTGSSNFAVGAAPHPFLHRYYQRQLSSTYRDLRKGVY
VPYTQGKWEGELGTDLVSIPHGPNVTVRANIAAITESDKFFINGS
NWEGILGLAYAEIARPDDSLEPFFDSLVKQTHVPNLFSLQLCGAG
FPLNQSEVLASVGGSMIIGGIDHSLYTGSLWYTPIRREWYYEVIIV
RVEINGQDLKMDCKEYNYDKSIVDSGTTNLRLPKKVFEAAVKSIK
AASSTEKFPDGFWLGEQLVCWQAGTTPWNIFPVISLYLMGEVTN
QSFRITILPQQYLRPVEDVATSQDDCYKFAISQSSTGTVMGAVIM
EGFYVVFDRARKRIGFAVSACHVHDEFRTAAVEGPFVTLDMEDC
GYNIPQTDE<u>DYKDDDDK</u>

FIG. 3A

ETDEEPEEPGRRGSFVEMVDNLRGKSGQGYYVEMTVGSPPQT
LNILVDTGSSNFAVGAAPHPFLHRYYQRQLSSTYRDLRKGVYVP
YTQGKWEGELGTDLVSIPHGPNVTVRANIAAITESDKFFINGSNW
EGILGLAYAEIARPDDSLEPFFDSLVKQTHVPNLFSLQLCGAGFP
LNQSEVLASVGGSMIIGGIDHSLYTGSLWYTPIRREWYYEVIIVRV
EINGQDLKMDCKEYNYDKSIVDSGTTNLRLPKKVFEAAVKSIKAA
SSTEKFPDGFWLGEQLVCWQAGTTPWNIFPVISLYLMGEVTNQ
SFRITILPQQYLRPVEDVATSQDDCYKFAISQSSTGTVMGAVIME
GFYVVFDRARKRIGFAVSACHVHDEFRTAAVEGPFVTLDMEDC
GYNIPQTDE<u>DYKDDDDK</u>

| | | | | | | | | | | | | | | | | |
|---|---|---|---|---|---|---|---|---|---|---|---|---|---|---|---|---|
| tac | cag | agg | cag | ctg | tcc | agc | aca | tac | cgg | gac | ctc | cgg | aag | ggt | gtg | 384 |
| Tyr | Gln | Arg | Arg | Leu | Ser | Ser | Thr | Tyr | Arg | Asp | Leu | Arg | Lys | Gly | Val | |
| | 115 | | | | | 120 | | | | | 125 | | | | | |
| tat | gtg | ccc | tac | acc | cag | ggc | aag | tgg | gaa | ggg | gag | ctg | ggc | acc | gac | 432 |
| Tyr | Val | Pro | Tyr | Thr | Gln | Gly | Lys | Trp | Glu | Gly | Glu | Leu | Gly | Thr | Asp | |
| | 130 | | | | | 135 | | | | | 140 | | | | | |
| ctg | gta | agc | atc | ccc | cat | ggc | ccc | aac | gtc | act | gtg | cgt | gcc | aac | att | 480 |
| Leu | Val | Ser | Ile | Pro | His | Gly | Pro | Asn | Val | Thr | Val | Arg | Ala | Asn | Ile | |
| 145 | | | | | 150 | | | | | 155 | | | | | 160 | |

N-glycos

| | | | | | | | | | | | | | | | | |
|---|---|---|---|---|---|---|---|---|---|---|---|---|---|---|---|---|
| gct | gcc | atc | act | gaa | tca | gac | aag | ttc | atc | aac | ggc | tcc | aac | tgg | | 528 |
| Ala | Ala | Ile | Thr | Glu | Ser | Asp | Lys | Phe | Ile | Asn | Gly | Ser | Asn | Trp | | |
| | | 165 | | | | | 170 | | | | | 175 | | | | |

N-glycos

| | | | | | | | | | | | | | | | | |
|---|---|---|---|---|---|---|---|---|---|---|---|---|---|---|---|---|
| gaa | ggc | atc | ctg | ggg | ctg | gcc | tat | gct | gag | att | gcc | agg | cct | gac | gac | 576 |
| Glu | Gly | Ile | Leu | Gly | Leu | Ala | Tyr | Ala | Glu | Ile | Ala | Arg | Pro | Asp | Asp | |
| | | 180 | | | | | 185 | | | | | 190 | | | | |
| tcc | ctg | gag | cct | ttc | ttt | gac | tct | ctg | gta | aag | cag | acc | cac | gtt | ccc | 624 |
| Ser | Leu | Glu | Pro | Phe | Phe | Asp | Ser | Leu | Val | Lys | Gln | Thr | His | Val | Pro | |
| | | 195 | | | | | 200 | | | | | 205 | | | | |
| aac | ctc | ttc | tcc | ctg | cag | ctt | tgt | ggt | gct | ggc | ttc | ccc | ctc | aac | cag | 672 |
| Asn | Leu | Phe | Ser | Leu | Gln | Leu | Cys | Gly | Ala | Gly | Phe | Pro | Leu | Asn | Gln | |
| 210 | | | | | 215 | | | | | 220 | | | | | | |

N-glycos

Fig. 5C

```
tct gaa gtg ctg gcc tct gtc gga ggg agc atg atc att gga ggt atc    720
Ser Glu Val Leu Ala Ser Val Gly Gly Ser Met Ile Ile Gly Gly Ile
225                     230                 235                 240
N-gly gac cac tcg ctg tac aca ggc agt ctc tgg tat aca ccc atc cgg cgg    768
Asp His Ser Leu Tyr Thr Gly Ser Leu Trp Tyr Thr Pro Ile Arg Arg
            245                 250                 255 gag tgg tat tat gag gtg atc att gtg cgg gtg gag atc aat gga cag    816
Glu Trp Tyr Tyr Glu Val Ile Ile Val Arg Val Glu Ile Asn Gly Gln
        260                 265                 270 gat ctg aaa atg gac tgc aag gag tac aac tat gac aag agc att gtg    864
Asp Leu Lys Met Asp Cys Lys Glu Tyr Asn Tyr Asp Lys Ser Ile Val
    275                 280                 285 gac agt ggc acc acc aac ctt cgt ttg ccc aag aaa gtg ttt gaa gct    912
Asp Ser Gly Thr Thr Asn Leu Arg Leu Pro Lys Lys Val Phe Glu Ala
290                 295                 300 gca gtc aaa tcc atc aag gca gcc tcc acg gag aag ttc cct gat        960
Ala Val Lys Ser Ile Lys Ala Ala Ser Thr Glu Lys Phe Pro Asp
305                 310                 315                 320
        <--Active-D--> ggt ttc tgg cta gga gag cag ctg gtg tgc tgg caa gca ggc acc acc   1008
Gly Phe Trp Leu Gly Glu Gln Leu Val Cys Trp Gln Ala Gly Thr Thr
            325                 330                 335
```

Fig. 5D

```
cct tgg aac att ttc cca gtc atc tca ctc tac cta atg ggt gag gtt    1056
Pro Trp Asn Ile Phe Pro Val Ile Ser Leu Tyr Leu Met Gly Glu Val
340                         345                 350 acc aac cag tcc ttc cgc atc acc atc ctt ccg caa tac cag ctg cgg    1104
Thr Asn Gln Ser Phe Arg Ile Thr Ile Leu Pro Gln Tyr Gln Leu Arg
        355                     360                 365
        [N-glycos]

cca gtg gaa gat gtg gcc acg tcc caa gac gac tgt tac aag ttt gcc    1152
Pro Val Glu Asp Val Ala Thr Ser Gln Asp Asp Cys Tyr Lys Phe Ala
370                     375                 380 atc tca cag tca tcc acg ggc act gtt atg gga gct gtt atc atg gag    1200
Ile Ser Gln Ser Ser Thr Gly Thr Val Met Gly Ala Val Ile Met Glu
385                 390                 395                 400 ggc ttc tac gtt gtc ttc gat cgg gcc cga aaa cga att ggc ttt gct    1248
Gly Phe Tyr Val Val Phe Asp Arg Ala Arg Lys Arg Ile Gly Phe Ala
            405                 410                 415 gtc agc gct tgc cat gtg cac gat gag ttc agg acg gca gcg gtg gaa    1296
Val Ser Ala Cys His Val His Asp Glu Phe Arg Thr Ala Ala Val Glu
420                 425                 430

[Internal peptide sequence]
```

Fig. 5E

```
ggc cct ttt gtc acc ttg gac atg gaa gac tgt ggc tac aac att cca    1344
Gly Pro Phe Val Thr Leu Asp Met Glu Asp Cys Gly Tyr Asn Ile Pro
435                     440                     445 cag aca gat gag tca acc ctc atg acc ata gcc tat gtc atg gct gcc    1392
Gln Thr Asp Glu Ser Thr Leu Met Thr Ile Ala Tyr Val Met Ala Ala
        450                     455                     460
                                              |―――Transmembrane――― atc tgc gcc ctc ttc atg ctg cca ctc tgc ctc atg gtg tgt cag tgg    1440
Ile Cys Ala Leu Phe Met Leu Pro Leu Cys Leu Met Val Cys Gln Trp
465                     470                     475             480
―――――――――――――――――――――|    |―――Transmembrane――― cgc tgc ctc cgc tgc ctg cgc cag cag cat gat gac ttt gct gat gac    1488
Arg Cys Leu Arg Cys Leu Arg Gln Gln His Asp Asp Phe Ala Asp Asp
            485                     490                     495 atc tcc ctg ctg aag tga                                            1506
Ile Ser Leu Leu Lys
        500
```

```
          E   T   D   E   E   P   E   E   P   G   R   R   G   S   F   V   E   M   V   D   N
       GARACNGAYGARGARCCNGARGARCCNGGNMGNMGNGGNWSNTTYGTNGARATGGTNGAYAAY  63
```

[ 3427-3430 →  5' primer set 1 ]          [ ← 3431-3434  3' primer set 1 ]

[ 3448-3451 → 5' primer set 2 ]          [ ← 3452-3455  3' primer set 2 ]

↓ 1° HNC/primer set 1

(3428+3433)
54 bp product

↓ 1°HNC & IMR32/ primer set 2

72 bp product sequence:

```
                        set2         3460
                        [5']   ←  5' RACE primer
         CCCGAAGAGCCCGGCCGGAGGGGCAGCTTTGTCGA  35
          P   E   E   P   G   R   R   G   S   F   V
                            ORF  →                [3']
                        3' RACE primer             set 2
                            3459
```

Fig. 9

|  | 10 | 20 | 30 | 40 |
|---|---|---|---|---|
| Hump501prot | MAQALPWLLLWMGAG | VLPAHGTQHGIR | LPLRSGL | GGAPLG | 40 |
| Musp501prot | MAPALHWLLLWVGSGM | LPAQGTHLGIR | LPLRSGL | AGPPLG | 40 |

|  | 50 | 60 | 70 | 80 |
|---|---|---|---|---|
| Hump501prot | LRLPRETDEEPEEPGRRGSFVEMVDNLRGKSGQGYYVEMT | 80 |
| Musp501prot | LRLPRETDEESEEPGRRGSFVEMVDNLRGKSGQGYYVEMT | 80 |

|  | 90 | 100 | 110 | 120 |
|---|---|---|---|---|
| Hump501prot | VGSPPQTLNILVDTGSSNFAVGAAPHPFLHRYYQRQLSST | 120 |
| Musp501prot | VGSPPQTLNILVDTGSSNFAVGAAPHPFLHRYYQRQLSST | 120 |

|  | 130 | 140 | 150 | 160 |
|---|---|---|---|---|
| Hump501prot | YRDLRKGVYVPYTQGKWEGELGTDLVSIPHGPNVTVRANI | 160 |
| Musp501prot | YRDLRKGVYVPYTQGKWEGELGTDLVSIPHGPNVTVRANI | 160 |

|  | 170 | 180 | 190 | 200 |
|---|---|---|---|---|
| Hump501prot | AAITESDKFFINGSNWEGILGLAYAEIARPDDSLEPFFDS | 200 |
| Musp501prot | AAITESDKFFINGSNWEGILGLAYAEIARPDDSLEPFFDS | 200 |

|  | 210 | 220 | 230 | 240 |
|---|---|---|---|---|
| Hump501prot | LVKQTHVPNLFSLQLCGAGFPLNQSEVLASVGGSMIIGGI | 240 |
| Musp501prot | LVKQTHIPNIFSLQLCGAGFPLNQTEALASVGGSMIIGGI | 240 |

|  | 250 | 260 | 270 | 280 |
|---|---|---|---|---|
| Hump501prot | DHSLYTGSLWYTPIRREWYYEVIIVRVEINGQDLKMDCKE | 280 |
| Musp501prot | DHSLYTGSLWYTPIRREWYYEVIIVRVEINGQDLKMDCKE | 280 |

|  | 290 | 300 | 310 | 320 |
|---|---|---|---|---|
| Hump501prot | YNYDKSIVDSGTTNLRLPKKVFEAAVKSIKAASSTEKFPD | 320 |
| Musp501prot | YNYDKSIVDSGTTNLRLPKKVFEAAVKSIKAASSTEKFPD | 320 |

|  | 330 | 340 | 350 | 360 |
|---|---|---|---|---|
| Hump501prot | GFWLGEQLVCWQAGTTPWNIFPVISLYLMGEVTNQSFRIT | 360 |
| Musp501prot | GFWLGEQLVCWQAGTTPWNIFPVISLYLMGEVTNQSFRIT | 360 |

|  | 370 | 380 | 390 | 400 |
|---|---|---|---|---|
| Hump501prot | ILPQQYLRPVEDVATSQDDCYKFAISQSSTGTVMGAVIME | 400 |
| Musp501prot | ILPQQYLRPVEDVATSQDDCYKFAVSQSSTGTVMGAVIME | 400 |

|  | 410 | 420 | 430 | 440 |
|---|---|---|---|---|
| Hump501prot | GFYVVFDRARKRIGFAVSACHVHDEFRTAAVEGPFVTLDM | 440 |
| Musp501prot | GFYVVFDRARKRIGFAVSACHVHDEFRTAAVEGPFVTADM | 440 |

|  | 450 | 460 | 470 | 480 |
|---|---|---|---|---|
| Hump501prot | EDCGYNIPQTDESTLMTIAYVMAAICALFMLPLCLMVCQW | 480 |
| Musp501prot | EDCGYNIPQTDESTLMTIAYVMAAICALFMLPLCLMVCQW | 480 |

|  | 490 | 500 |
|---|---|---|
| Hump501prot | RCLRCLRQQHDDFADDISLLK | 501 |
| Musp501prot | RCLRCLRHQHDDFGDDISLLK | 501 |

FIG. 10

CTGTTGGGCTCGCGGTTGAGGACAAACTCTTCGCGGTCTTTCCAGTACTCT
TGGATCGGAAACCCGTCGGCCTCCGAACGGTACTCCGCCACCGAGGGACCT
GAGCGAGTCCGCATCGACCGGATCGGAAACCTCTCGACTGTTGGGGTGAG
TACTCCCTCTCAAAAGCGGGCATGACTTCTGCGCTAAGATTGTCAGTTTCC
AAAAACGAGGAGGATTTGATATTCACCTGGCCGCGGTGATGCCTTTGAGG
GTGGCCGCGTCCATCTGGTCAGAAAAGACAATCTTTTTGTTGTCAAGCTTG
AGGTGTGGCAGGCTTGAGATCTGGCCATACACTTGAGTGACAATGACATCC
ACTTTGCCTTTCTCTCCACAGGTGTCCACTCCCAGGTCCAACTGCAGGTCG
ACTCTAGACCC

FIG. 11A

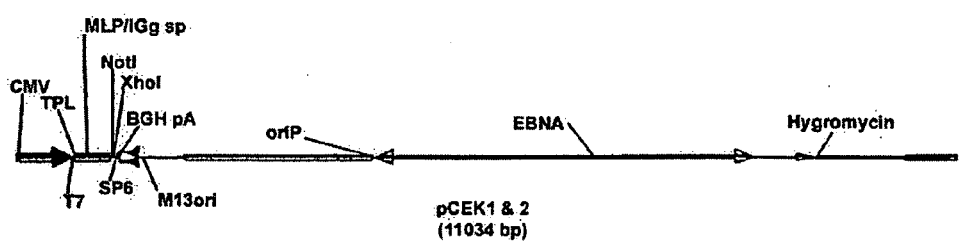

```
cgcggttgag gacaaactct tcgcggtctt tccagtactc ttggatcgga aacccgtcgg    840
cctccgaacg gtactccgcc accgagggac ctgagcgagt ccgcatcgac cggatcggaa    900
                                 splice donor
aacctctcga ctgttggggt gagtactccc tctcaaaagc gggcatgact tctgcgctaa    960
gattgtcagt ttccaaaaac gaggaggatt tgatattcac ctggcccgcg gtgatgcctt   1020
tgagggtggc cgcgtccatc tggtcagaaa agacaatctt tttgttgtca agcttgaggt   1080
gtggcaggct tgagatctgg ccatacactt gagtgacaat gacatccact ttgcttttct   1140
splice acceptor         SalI
ctccacaggt gtccactccc agtccaact gcaggtcgac tctagacccg gggaattctg    1200
cagatatcca tcacactggc cgcactcgtc cccagcccgc ccgggagctg cgagccgcga   1260
gctggattat ggtggcctga gcagccaacg cagccgcagg agcccggagc ccttgcccct   1320
gcccgcgccg ccgcccgcg ggggaccag cccgcgcccg ggaagccgcc accggcccgc    1380
cctcccagcc ccgccgggag cccgcgcccg ctgcccaggc tgcccgccgc cgtgccgatg   1440
tagcgggctc cggatcccag cctctcccct gctcccgtgc tctgcggatc tcccctgacc   1500
gctctccaca gcccgaccc ggggctggc ccaggcccct gcaggccctg gcgtcctgat    1560
gcccccaagc tccctctcct gagaagccac cagcaccacc cagacttggg ggcaggcgcc   1620
```

Figure 13C

```
aggacggac gtggccagt gcgagcccag aggcccgaa ggccggggcc cacc atg                1677
                                                         Met
                                                          1 gcc caa gcc ctg ccc tgg ctc ctg ctg tgg atg ggc gcg gga gtg ctg            1725
Ala Gln Ala Leu Pro Trp Leu Leu Leu Trp Met Gly Ala Gly Val Leu
                     5                      10                  15 cct gcc cac ggc acc cag cac ggc atc cgg ctg ccc ctg cgc agc ggc            1773
Pro Ala His Gly Thr Gln His Gly Ile Arg Leu Pro Leu Arg Ser Gly
             20                      25                      30 ctg ggg ggc gcc ccc ctg ggg ctg cgg ctg ccc cgg gag acc gac gaa            1821
Leu Gly Gly Ala Pro Leu Gly Leu Arg Leu Pro Arg Glu Thr Asp Glu
     35                      40                      45 gag ccc gag gag ccc cgg agg ggc cgg agc ttt gtg gag atg gtg gac            1869
Glu Pro Glu Glu Pro Gly Arg Arg Gly Ser Phe Val Glu Met Val Asp
 50                      55                      60                  65 aac ctg agg ggc aag tcg ggg cag ggc tac tac gtg gag atg acc gtg            1917
Asn Leu Arg Gly Lys Ser Gly Gln Gly Tyr Tyr Val Glu Met Thr Val
             70                      75                      80 ggc agc ccc ccg cag acg ctc aac atc ctg gtg gat aca ggc agc agt            1965
Gly Ser Pro Pro Gln Thr Leu Asn Ile Leu Val Asp Thr Gly Ser Ser
             85                      90                      95
```

Figure 13D

```
aac ttt gca gtg ggt gct gcc ccc cac ccc ttc ctg cat cgc tac tac    2013
Asn Phe Ala Val Gly Ala Ala Pro His Pro Phe Leu His Arg Tyr Tyr
             100                     105                     110 cag agg cag ctg tcc agc aca tac cgg gac ctc cgg aag ggt gtg tat    2061
Gln Arg Gln Leu Ser Ser Thr Tyr Arg Asp Leu Arg Lys Gly Val Tyr
             115                     120                     125 gtg ccc tac acc cag ggc aag tgg gaa ggg gag ctg ggc acc gac ctg    2109
Val Pro Tyr Thr Gln Gly Lys Trp Glu Gly Glu Leu Gly Thr Asp Leu
             130                     135                     140                 145 gta agc atc ccc cat ggc ccc aac gtc act gtg cgt gcc aac att gct    2157
Val Ser Ile Pro His Gly Pro Asn Val Thr Val Arg Ala Asn Ile Ala
             150                     155                     160 gcc atc act gaa tca gac aag ttc ttc atc aac ggc tcc aac tgg gaa    2205
Ala Ile Thr Glu Ser Asp Lys Phe Phe Ile Asn Gly Ser Asn Trp Glu
             165                     170                     175 ggc atc ctg ggg ctg gcc tat gct gag att gcc agg cct gac gac tcc    2253
Gly Ile Leu Gly Leu Ala Tyr Ala Glu Ile Ala Arg Pro Asp Asp Ser
             180                     185                     190 ctg gag cct ttc ttt gac tct ctg gta aag cag acc cac gtt ccc aac    2301
Leu Glu Pro Phe Phe Asp Ser Leu Val Lys Gln Thr His Val Pro Asn
             195                     200                     205
```

Figure 13E

```
ctc ttc tcc ctg cag ctt tgt ggt gct ggc ttc ccc ctc aac cag tct    2349
Leu Phe Ser Leu Gln Leu Cys Gly Ala Gly Phe Pro Leu Asn Gln Ser
210                 215                 220                 225 gaa gtg ctg gcc tct gtc gga ggg agc atg atc att gga ggt atc gac    2397
Glu Val Leu Ala Ser Val Gly Gly Ser Met Ile Ile Gly Gly Ile Asp
        230                 235                 240 cac tcg ctg tac aca ggc agt ctc tgg tat aca ccc atc cgg cgg gag    2445
His Ser Leu Tyr Thr Gly Ser Leu Trp Tyr Thr Pro Ile Arg Arg Glu
    245                 250                 255 tgg tat tat gag gtc atc att gtg cgg gtg gag atc aat gga cag gat    2493
Trp Tyr Tyr Glu Val Ile Ile Val Arg Val Glu Ile Asn Gly Gln Asp
260                 265                 270 ctg aaa atg gac tgc aag gag tac aac tat gac aag agc att gtg gac    2541
Leu Lys Met Asp Cys Lys Glu Tyr Asn Tyr Asp Lys Ser Ile Val Asp
        275                 280                 285 agt ggc acc acc aac ctt cgt ttg ccc aag aaa gtg ttt gaa gct gca    2589
Ser Gly Thr Thr Asn Leu Arg Leu Pro Lys Lys Val Phe Glu Ala Ala
    290                 295                 300                 305 gtc aaa tcc atc aag gca gcc tcc tcc acg gag aag ttc cct gat ggt    2637
Val Lys Ser Ile Lys Ala Ala Ser Ser Thr Glu Lys Phe Pro Asp Gly
310                 315                 320
```

Figure 13F

```
ttc tgg cta gga gag cag ctg gtg tgc tgg caa gca ggc acc acc cct    2685
Phe Trp Leu Gly Glu Gln Leu Val Cys Trp Gln Ala Gly Thr Thr Pro
325                             330                     335 tgg aac att ttc cca gtc atc tca ctc tac cta atg ggt gag gtt acc    2733
Trp Asn Ile Phe Pro Val Ile Ser Leu Tyr Leu Met Gly Glu Val Thr
        340                     345                     350 aac cag tcc ttc cgc atc acc atc ctt ccg cag caa tac ctg cgg cca    2781
Asn Gln Ser Phe Arg Ile Thr Ile Leu Pro Gln Gln Tyr Leu Arg Pro
355                     360                     365 gtg gaa gat gtg gcc acg tcc caa gac gac tgt tac aag ttt gcc atc    2829
Val Glu Asp Val Ala Thr Ser Gln Asp Asp Cys Tyr Lys Phe Ala Ile
370                     375                     380             385 tca cag tca tcc acg ggc act gtt atg gga gct gtt atc atg gag ggc    2877
Ser Gln Ser Ser Thr Gly Thr Val Met Gly Ala Val Ile Met Glu Gly
            390                     395                     400 ttc tac gtt gtc ttt gat cgg gcc cga aaa cga att ggc ttt gct gtc    2925
Phe Tyr Val Val Phe Asp Arg Ala Arg Lys Arg Ile Gly Phe Ala Val
405                     410                     415 agc gct tgc cat gtg cac gat gag ttc agg acg gca gcg gtg gaa ggc    2973
Ser Ala Cys His Val His Asp Glu Phe Arg Thr Ala Ala Val Glu Gly
420                     425                     430
```

Figure 13G

```
cct ttt gtc acc ttg gac atg gaa gac tgt ggc tac aac att cca cag   3021
Pro Phe Val Thr Leu Asp Met Glu Asp Cys Gly Tyr Asn Ile Pro Gln
435                     440                     445 aca gat gag tca acc ctc atg acc ata gcc tat gtc atg gct gcc atc   3069
Thr Asp Glu Ser Thr Leu Met Thr Ile Ala Tyr Val Met Ala Ala Ile
450                     455                     460             465 tgc gcc ctc ttc atg ctg cca ctc tgc ctc atg gtg tgt cag tgg cgc   3117
Cys Ala Leu Phe Met Leu Pro Leu Cys Leu Met Val Cys Gln Trp Arg
                470                     475                     480 tgc ctc cgc tgc ctg cgc cag cag cat gat gac ttt gct gat gac atc   3165
Cys Leu Arg Cys Leu Arg Gln Gln His Asp Asp Phe Ala Asp Asp Ile
            485                     490                     495 tcc ctg ctg aag tga ggaggcccat gggcagaaga tagagattcc cctgaccac    3220
Ser Leu Leu Lys
500 acctccgtgg ttcactttgg tcacaagtag gagacacaga tggcacctgt ggccagagca  3280 cctcaggacc ctcccccacc accaaatgcc tctgccttga tggagaagga aaaggctggc  3340 aaggtgggtt ccagggactg tacctgtagg aaacagaaaa gagaagaaag aagcactctg  3400 ctgcgggaa tactcttgt cacctcaaat ttaagtcggg aaattctgct gcttgaaact   3460
```

Figure 13H

```
tcagccctga accttttgtcc accattcctt taaattctcc aacccaagt attctttctt  3520
tcttagtttc agaagtactg gcatcacacg caggttacct tggcgtgtgt ccctgtggta  3580
                     HindIII
ccctggcaga gaagagacca agcttgtttc cctgctgcc  aaagtcagta ggagaggatg  3640
cacagtttgc tatttgcttt agagacaggg actgtataaa caagcctaac attggtgcaa  3700
agattgcctc ttgaattaaa aaaaaaaact agattgacta tttatacaaa tgggggcggc  3760
tggaaagagg agaaggagag ggagtacaaa gacagggaat agtgggatca aagctaggaa  3820
aggcagaaac acaaccactc accagtccta gttttagacc tcatctccaa gatagcatcc  3880
catctcagaa gatgggtgtt gtttttcaatg tttttctttc tgtggttgca gcctgaccaa  3940
aagtgagatg ggaagggctt atctagccaa agagctcttt tttagctctc ttaaatgaag  4000
tgcccactaa gaagttccac ttaacacatg aatttctgcc atattaattt cattgtctct  4060
atctgaacca ccctttattc tacatatgat aggcagcact gaaatatcct aaccccctaa  4120
gctccaggtg ccctgtggga gagcaactgg actatagcag ggctgggctc tgtcttcctg  4180
gtcataggct cactctttcc cccaaatctt cctctggagc tttgcagcca aggtgctaaa  4240
aggaataggt aggagacctc ttctatctaa tccttaaaag cataatgttg aacattcatt  4300
```

Figure 13I

```
caacagctga tgccctataa ccctgcctg gattcttcc tattaggcta taagaagtag 4360
caagatcttt acataattca gagtggtttc attgccttcc taccctctct aatgcccct  4420
ccatttattt gactaaagca tcacacagtg gcactagcat tataccaaga gtatgagaaa 4480
tacagtgctt tatgctcta acattactgc cttcagtatc aaggctgcct ggagaaagga  4540
tggcagcctc agggcttcct tatgtcctcc accacaagag ctccttgatg aaggtcatct  4600
ttttcccta tcctgttctt cccctccccg ctcctaatgg tacgtgggta cccaggctgg  4660
ttcttgggct aggtagtggg gaccaagttc attacctccc tatcagttct agcatagtaa  4720
actacgtac cagtgttagt gggaagagct gggtttcct agtataccca ctgcatccta   4780
ctcctacctg gtcaaccgc tgcttccagg tatggacct gctaagtgtg gaattacctg    4840
ataaggaga gggaaataca aggagggcct ctggtgttcc tggcctcagc cagctgccca   4900
caagccataa accaataaaa caagaatact gagtcagttt tttatctggg ttctcttcat  4960
tcccactgca cttggtgctg ctttgctga ctgggaacac cccataacta cagagtctga   5020
caggaagact ggagactgtc cacttctagc tcggaactta ctgtgtaaat aaactttcag  5080
aactgctacc atgaagtgaa aatgccacat tttgctttat aatttctacc catgttggga  5140
```

Figure 13J

```
aaaactggct tttccagc cctttccagg gcataaaact caacccttc gatagcaagt 5200
cccatcagcc tattatttt ttaaagaaaa cttgcacttg ttttctttt tacagttact 5260
tccttcctgc cccaaaatta taaactctaa gtgtaaaaaa aagtcttaac aacagcttct 5320
tgcttgtaaa aatatgtatt atttttaaat tctgctcctg aaaaatgact 5380
gtccattct ccactcactg catttggggc ctttcccatt ggtctgcatg tcttttatca 5440
ttgcaggcca gtggacagag ggagaaggga gaacagggt cgccaacact tgtgttgctt 5500
tctgactgat cctgaacaag aaagagtaac actgaggcgc tcgctcccat gcacaactct 5560
ccaaaacact tatcctcctg caagagtggg ctttccgggt cttactggg aagcagttaa 5620
gccccctcct caccccttcc tttttctttt cttactcct ttggcttcaa aggattttgg 5680
aaaagaaaca atatgcttta cactcatttt caatttctaa atttgcaggg gatactgaaa 5740
aatacggcag gtggcctaag gctgctgtaa agttgagggg agaggaaatc ttaagattac 5800
aagataaaaa acgaatcccc taaacaaaaa gaacaataga actggtcttc catttgcca 5860
cctttcctgt tcatgacagc tactaacctg gagacagtaa catttcatta accaaagaaa 5920
gtgggtcacc tgacctctga agagctgagt actcaggcca ctccaatcac cctacaagat 5980
```

Figure 13K gccaaggagg tcccaggaag tccagctcct taaactgacg ctagtcaata aacctgggca 6040
agtgaggcaa gagaaatgag gaagaatcca tctgtgaggt gacaggcacg gatgaaagac 6100
aaagacggaa aagagtatca aaggcagaaa ggagatcatt tagttgggtc tgaaaggaaa 6160
agtntttgct atccgacatg tactgctagt wcctgtaagc atttaggtc ccagaatgga 6220 aaaaaaaatc aagctatngg ttatatataata atgnnnnnnn nntcgagcat 6280
gcatctagag ggccctattc tatagtgtca cctaaatgct agagctcgct gatcagcctc 6340
gactgtgcct tctagttgcc agccatctgt tgtttgcccc tccccgtgc cttccttgac 6400 cctgaaggt gccactccca ctgtcctttc ctaataaaat gaggaaattg catcgcattg 6460
tctgagtagg tgtcattcta ttctgggggg tggggtgggg caggacagca aggggagga 6520 ttgggaagac aatagcaggc atgctgggga tgcggtgggc tctatggctt ctgaggcgga 6580
aagaaccagc tggggtccta ggggtatcc ccacgcgccc tgtagcggcg cattaagcgc 6640
ggcgggtgtg gtggttacgc gcagcgtgac cgctacactt gccagcgccc tagcgcccgc 6700
tcctttcgct ttcttccctt cctttctcgc cacgttcgcc ggctttcccc gtcaagctct 6760 aaatcgggc atcccttttag ggttccgatt tagtgcttta cggcacctcg acccaaaaa 6820

Figure 13L

```
acttgattag ggtgatggtt cacgtagtgg gccatcgccc tgatagacgg tttttcgccc 6880
tttgacgttg gagtccacgt tctttaatag tggactcttg ttccaaactg aacaacact 6940
caaccctatc tcggtctatt cttttgattt ataagggatt ttggggattt cggcctattg 7000
gttaaaaaat gagctgattt aacaaaaatt taacgcgaat tctagagccc cgccgccgga 7060
cgaactaaac ctgactacgg catctctgcc ccttcttcgc ggggcagtgc atgtaatccc 7120
ttcagttggt tggtacaact tgccaactgg gccctgttcc acatgtgaca cggggggga 7180
ccaaacacaa aggggttctc tgactgtagt tgacatcctt ataaatggat gtgcacattt 7240
gccaacactg agtggctttc atcctggagc agactttgca gtctgtggac tgcaacacaa 7300
cattgccttt atgtgtaact cttggctgaa gctcttacac caatgctggg ggacatgtac 7360
ctcccagggg cccaggaaga ctacgggagg ctcaagagag gtcaatcaga gggcctgtg 7420
tagctaccga taagcggacc ctcaagaggg cattagcaat agtgtttata agcccctt 7480
HpaI
gttaaccta aacgggtagc atatgcttcc cgggtagtag tatatactat ccagactaac 7540
cctaattcaa tagcatatgt tacccaacgg gaagcatatg ctatcgaatt agggttagta 7600
EcoRV
aagggtcct aaggaacagc gatatctccc accccatgag ctgtcacggt tttatttaca 7660
```

Figure 13M

```
tggggtcagg attccacgag ggtagtgaac catttagtc acaagggcag tggctgaaga 7720
tcaaggagcg ggcagtgaac tctcctgaat cttcgcctgc ttcttcattc tccttcgttt 7780
agctaataga ataactgctg agttgtgaac agtaaggtgt atgtgaggtg ctcgaaaaca 7840
aggtttcagg tgacgccccc agaataaaat ttggacgggg ggttcagtgg tggcattgtg 7900
                                                        SpeI
ctatgacacc aatataaccc tcacaaaccc cttgggcaat aaatactagt gtaggaatga 7960
aacattctga atatctttaa caatagaaat ccatgggggtg gggcaacaca gtaaagactg 8020
gatgtccatc tcacacgaat ttatgctat gggcaacaca taatcctagt gcaatatgat 8080
actggggtta ttaagatgtg tcccaggcag ggaccaagac aggtgaacca tgttgttaca 8140
ctctatttgt aacaagggga agagagtgg acgccgacag cagcggactc cactggttgt 8200
ctctaacacc cccgaaaatt aaacggggct ccacgccaat gggcccata aacaaagaca 8260
agtggccact cttttttttg aaattgtgga gtgggggcac gcgtcagccc ccacacgccg 8320
ccctgcggtt ttgactgta aaataagggt gtaataactt ggctgattgt aaccccgcta 8380
accactgcgg tcaaaccact tgcccacaaa accactaatg gcacccccggg gaatacctgc 8440
ataagtaggt gggcgggcca agataggggc gcgattgctg cgatctggag gacaaattac 8500
```

Figure 13N
acacacttgc gcctgagcgc caagcacagg gttgttggtc ctcatattca cgaggtcgct 8560
gagagcacgg tgggctaatg ttgccatggg tagcatatac tacccaaata tctggatagc 8620
atatgctatc ctaatctata tctgggtagc ataggctatc ctaatctata tctgggtagc 8680
atatgctatc ctaatctata tctgggtagt atatgctatc ctaatttata tctgggtagc 8740
ataggctatc ctaatctata tctgggtagc atatgctatc ctaatctata tctgggtagt 8800
atatgctatc ctaatctgta tccgggtagc atatgctatc ctaatagaga ttagggtagt 8860
atatgctatc ctaatttata tctgggtagc atatactacc caaatatctg gatagcatat 8920
gctatcctaa tctatatctg ggtagcatat gctatcctaa tctatatctg ggtagcatag 8980
gctatcctaa tctatatctg ggtagcatat gctatcctaa tctatatctg ggtagtatat 9040
gctatcctaa tttatatctg ggtagcatag gctatcctaa tctatatctg ggtagcatat 9100
gctatcctaa tctatatctg ggtagtatat gctatcctaa tctgtatccg ggtagcatat 9160
gctatcctca tgcatataca gtcagcatat gataccagt agtagagtgg gagtgctatc 9220
ctttgcatat gccgccacct cccaaggggg cgtgaatttt cgctgcttgt cctttcctg 9280
    oriP
catgctggtt gctcccattc ttaggtgaat ttaaggaggc caggctaaag ccgtcgcatg 9340
              →

Figure 130

```
tcgattgct caccaggtaa atgtcgctaa tgttttccaa cgcgagaagg tgttgagcgc    9400
ggagctgagt gacgtgacaa catggtatg cccaattgcc ccatgttggg aggacgaaaa    9460
tggtgacaag acagatggcc agaaatacac caacagcacg catgatgtct actgggatt    9520
tattctttag tgcgggggaa tacacggctt ttaatacgat tgagggcgtc tcctaacaag   9580
ttacatcact cctgcccttc ctcaccctca tctccatcac ctccttcatc tccgtcatct   9640
ccgtcatcac cctccgcggc agcccttcc accataggtg gaaaccaggg aggcaaatct    9700
actccatcgt caaagctgca cacagtcacc ctgatatttgc aggtaggagc gggctttgtc  9760
ataacaaggt ccttaatcgc atccttcaaa acctcagcaa atatatgagt ttgtaaaaag   9820
accatgaaat aacagacaat ggactccctt agcgggccag gttgtgggcc gggtccaggg   9880
gccattccaa agggagacg actcaatggt gtaagacgac attgtggaat agcaagggca    9940
gttcctcgcc ttaggttgta aagggaggtc ttactacctc catatacgaa cacaccggcg   10000
accaagttc cttcgtcggt agtccttct acgtgactcc tagccaggag agctcttaaa     10060
ccttctgcaa tgttctcaaa tttcgggttg gaacctcctt gaccacgatg ctttccaaac  10120
caccctcctt ttttgcgcct gcctccatca ccctgacccc ggggtccagt gcttgggcct   10180
```

Figure 13P

```
tctcctgggt catctgcggg gccctgctct atcgctcccg gggcacgtc aggctcacca 10240
tctggccac cttcttggtg gtattcaaaa taatcggctt ccctacagg gtggaaaaat 10300
ggccttctac ctggaggggg cctgcgcggt ggagacccgg atgatgatga ctgactactg 10360
ggactcctgg gcctctttc tccacgtcca cgacctctcc cctgctct ttcacgactt 10420
cccccctgg ctctttcacg tcctctaccc cggcggcctc cactacctc tcgacccgg 10480
cctccactac ctcctcgacc ccggcctcca ctgcctcctc gaccccggcc tccacctcct 10540
gctcctgccc ctcctgctcc tgcccctcc cctgctcctg ccctcctgc cctcctgct 10600
cctgcccctc ctgcccctcc tgctcctgcc cctcctgctcc ctcctgccc tgccctcct 10660
gccctcctc ctgctcctgc cctcctgcc ctcctgccc ctcctgcccc tcctgcccct 10720
cctgcccctg ccctcctgcc cctcctgcc cctcctgctc ctgccccctc tgccctcct 10780
cctgctcctc ctgcccctcc tgctcctgcc cctcctgctc ctgccccctc tgccctcct 10840
gccctcctc ctgctcctgc cctcctgct ctgccccctc tgccccctc tgccctcct 10900
gccctcctc ctgctcctgc cctcctgct cctgccccct ctgccccctc tcctgctcct 10960
gccctcctg ccctcctctc ctgctcctg ctcctgcccc cctgccccct cctgccccct 11020
```

Figure 13Q

```
cctgccccts ctcctgctcc tgccctcct gccctcctc ctgctcctg cctcctcct   11080
gctcctgcc ctcctgccc tcctgccct cctcctgctc ctgccctcc tcctgctcct  11140
gccctcctg ccctcctgc ccctcctgc ctcctcctg ctcctgccc tcctcctgct   11200
cctgccctc ctgctcctg ccctcccgct cctgctcctg ctcctgttcc accgtgggtc 11260
cctttgcagc caatgcaact tgggtcttt tgggtctcc ggacaccatc tctatgtctt  11320
ggccctgatc ctgagccgcc cggggctcct gtcttccgc ctcctcgtcc tcgtcctctt  11380
cccgtcctc gtccatggtt atcacccct cttctttgag gtccactgcc gccggagcct  11440
tctggtccag atgtgtctcc cttctctcct aggccatttc caggtcctgt acctgccccc 11500
tcgtcagaca tgattcacac taaaagagat caatagacat ctttattaga cgacgctcag  11560
tgaatacagg gagtgcagac tcctgccccc tccaacagcc ccccaccct catcccttc   11620
atggtcgctg tcagacagat ccagtctga aaattcccca tcctccgaac catcctcgtc  11680
ctcatcacca attactcgca gcccggaaaa ctcccgctga acatcctcaa gatttgcgtc  11740
ctgagcctca agccaggcct caaattcctc gtcccccttt ttgctggacg gtaggatgg   11800
ggattctcgg gacccctcct cttcctcttc aaggtcacca gacagagatg ctactgggc  11860
```

Figure 13R

```
                                          ClaI
aacggaagaa aagctgggtg cggcctgtga ggatcagctt atcgatgata agctgtcaaa 11920
catgagaatt cttgaagacg aaagggcctc gtgatacgcc tattttata ggttaatgtc 11980 atgataataa tggttctta gacgtcaggt ggcactttc ggaaatgt gcgcggaacc 12040 cctatttgtt tatttca aatacattca aatatgtatc cgctcatgag acaataaccc 12100
tgataaatgc ttcaataata ttgaaaaagg aagagtatga gtattcaaca tttccgtgtc 12160
gcccttattc ccttttttgc ggcattttgc cttcctgttt ttgctcaccc agaaacgctg 12220
gtgaaagtaa aagatgctga agatcagttg ggtgcacgag tggttacat cgaactggat 12280 ctcaacagcg gtaagatcct tgagagtttt cgccccgaag aacgttttcc aatgatgagc 12340
acttttaaag ttctgctatg tggcgcggta ttatcccgta ttgacgccgg gcaagagcaa 12400
ctcggtcgcc gcatacacta ttctcagaat gacttggttg agtactcacc agtcacagaa 12460
aagcatctta cggatggcat gacagtaaga gaattatgca gtgctgccat aaccatgagt 12520
gataacactg cggccaactt acttctgaca acgatcggag gaccgaagga gctaaccgct 12580
tttttgcaca acatggggga tcatgtaact cgccttgatc gttgggaacc ggagctgaat 12640
gaagccatac caaacgacga gcgtgacacc acgatgcctg cagcaatggc aacaacgttg 12700
                                          PvuI
```

Figure 13S

| | | | | |
|---|---|---|---|---|
| cgcaaactat | taactggcga | actacttact | ctagcttccc | ggcaacaatt aatagactgg 12760 |
| atggaggcgg | ataaagttgc | aggaccactt | ctgcgctcgg | cccttccggc tggctggttt 12820 |
| attgctgata | aatctggagc | cggtgagcgt | gggtctcgcg | gtatcattgc agcactgggg 12880 |
| ccagatggta | agccctcccg | tatcgtagtt | atctacacga | cggggagtca ggcaactatg 12940 |
| gatgaacgaa | atagacagat | cgctgagata | ggtgcctcac | tgattaagca ttggtaactg 13000 |
| tcagaccaag | tttactcata | attgatttaa | aacttcattt | ttaatttaaa 13060 |
| aggatctagg | tgaagatcct | ttttgataat | ctcatgacca | aaatccctta acgtgagttt 13120 |
| tcgttccact | gagcgtcaga | ccccgtagaa | aagatcaaag | gatcttcttg agatcctttt 13180 |
| tttctgcgcg | taatctgctg | cttgcaaaca | aaaaaaccac | cgctaccagc ggtggtttgt 13240 |
| ttgccggatc | aagagctacc | aactctttt | ccgaaggtaa | ctggcttcag cagagcgcag 13300 |
| ataccaaata | ctgtccttct | agtgtagccg | tagttaggcc | accacttcaa gaactctgta 13360 |
| gcaccgccta | catacctcgc | tctgctaatc | ctgttaccag | tggctgctgc cagtggcgat 13420 |
| aagtcgtgtc | ttaccgggtt | ggactcaaga | cgatagttac | cggataaggc gcagcggtcg 13480 |
| ggctgaacgg | ggggttcgtg | cacacagccc | agcttggagc | gaacgaccta caccgaactg 13540 |

Figure 13T

```
agatacctac agcgtgagct atgagaaagc gccacgcttc ccgaagggag aaaggcggac 13600
aggtatccgg taagcggcag ggtcggaaca ggagagcgca cgagggagct tccaggggga 13660
aacgcctggt atctttatag tcctgtcggg tttcgccacc tctgacttga gcgtcgattt 13720
ttgtgatgct cgtcaggggg gcggagccta tggaaaaacg ccagcaacgc ggccttttta 13780
cggttcctgg ccttttgctg cgccgcgtgc ggctgctgga gatggcggac gcgatggata 13840
tgttctgcca agggttggtt tgcgcattca cagttctccg caagaattga ttggctccaa 13900
ttcttggagt ggtgaatccg ttagcgaggt gccgccggct tccattcagg tcgaggtggc 13960
ccggctccat gcaacgcgac gcaacgcggg gaggcagaca aggtataggg cggcgcctac 14020
aatccatgcc aacccgttcc atgtgctcgc cgaggcggca taaatcgccg tgacgatcag 14080
cggtccagtg atcgaagtta ggctggtaag agccgcgagc gatccttgaa gctgtccctg 14140
atggtcgtca tctacctgcc tggacagcat ggcctgcaac gcgggcatcc cgatgccgcc 14200
                                                      NruI
ggaagcgaga agaatcataa tggggaaggc catccagcct cgcgtcgcga acgccagcaa 14260
gacgtagccc agcgcgtcgg ccgccatgcc ctgcttcatc ccgtggcc gttgctcgcg 14320
tttgctggcg gtgtccccgg aagaaatata tttgcatgtc tttagttcta tgatgacaca 14380
```

Figure 13U

```
aaccccgccc agcgtcttgt cattggcgaa ttcgaacacg cagatgcagt cggggcggcg  14440
cggtcccagg tccacttcgc atattaaggt gacgcgtgtg gcctcgaaca ccgagcgacc  14500
ctgcagcgac ccgcttaaca gcgtcaacag cgtgccgcag atcccgggca atgagatatg  14560
aaaaagcctg aactcaccgc gacgtctgtc gagaagtttc tgatcgaaaa gttcgacagc  14620
gtctccgacc tgatgcagct ctcggagggc gaagaatctc gtgctttcag cttcgatgta  14680
ggagggcgtg gatatgtcct gcggtaaat agctgcgccg atggtttcta caaagatcgt  14740
tagtggatc ggcactttgc atcggccgcg ctccccgatt ccggaagtgc ttgacattgg  14800
ggaattcagc gagagcctga cctattgcat ctccgcgcgt gcacagggtg tcacgttgca  14860
agacctgcct gaaaccgaac tgcccgctgt tctgcagccg gtcgcggagg ccatgatgc  14920
PvuI
gatcgctgcg gccgatctta gccagacgag cgggttcggc ccattcggac cgcaaggaat  14980
cggtcaatac actacatggc gtgattcat atgcgcgatt gctgatcccc atgtgtatca  15040
ctggcaaact gtgatggacg acaccgtcag tgcgtccgtc gcgcaggctc tcgatgagct  15100
gatgctttgg gccgaggact gccccgaagt ccggcacctc gtgcacgcgg atttcggctc  15160
caacaatgtc ctgacggaca atggccgcat aacagcggtc attgactgga gcgaggcgat  15220
```

Figure 13V

```
gttcgggat tcccaatacg aggtcgccaa catcttcttc tggaggccgt ggttggcggg  15280
tatggagcag cagacggcgct acttcgagcg gaggcatccg gagcttgcag gatcgccgcg  15340
gctccgggcg tatatgctcc gcattggtct tgaccaactc tatcagagct tggtttgacgg  15400
caatttcgat gatgcagctt gggcgcaggg tcgatgcgac gcaatcgtcc gatccggagc  15460
cgggactgtc gggcgtacac aaatcgcccg cagaagcgcg gccgtctgga ccgatggctg  15520
tgtagaagta ctcgccgata gtgaaaacgg gagatggggg aggctaactg aaacacggaa  15580
ggagacaata ccgcgctat gacggcaata aaaagacaga ataaaacgca  15640
cgggtgttgg gtcgtttgtt cataaacgcg gggttcggtc ccaggctgg cactctgtcg  15700
ataccccacc gagacccat tgggccaat acgcccgcgt ttcttcctttt tccccacccc  15760
acccccaag ttcgggtgaa ggccaggc tcgcagccaa cgtcggggcg gcaggccctg  15820
ccatagccac tggccccgtg ggttagggac ggggtccccc atggggaatg gtttatgtt  15880
cgtgggggtt attattttgg gcgttgcgtg gggtctggtc cacgactgga ctgagcagac  15940
agacccatgg tttttggatg gcctgggcat ggaccgcatg tactggcgcg acacgaacac  16000
cggggcgtctg tggctgccaa acaccccga ccccaaaaa ccaccgcgcg gatttctggc  16060
```

Figure 13W    SalI
gtgccaagct agtcgaccaa              16080
▲

CTGTTGGGCTCGCGGTTGAGGACAAACTCTTCGCGGTCTTTCCAGTACTCTTGGATCGGAAAC
CCGTCGGCCTCCGAACGGTACTCCGCCACCGAGGGACCTGAGCGAGTCCGCATCGACCGGAT
CGGAAAACCTCTCGACTGTTGGGGTGAGTACTCCCTCTCAAAAGCGGGCATGACTTCTGCGCT
AAGATTGTCAGTTTCCAAAAACGAGGAGGATTTGATATTCACCTGGCCCGCGGTGATGCCTTT
GAGGGTGGCCGCGTCCATCTGGTCAGAAAAGACAATCTTTTTGTTGTCAAGCTTGAGGTGTGG
CAGGCTTGAGATCTGGCCATACACTTGAGTGACAATGACATCCACTTTGCCTTTCTCTCCACAG
GTGTCCACTCCCAGGTCCAACTGCAGGTCGACTCTAGACCC

FIG. 14A

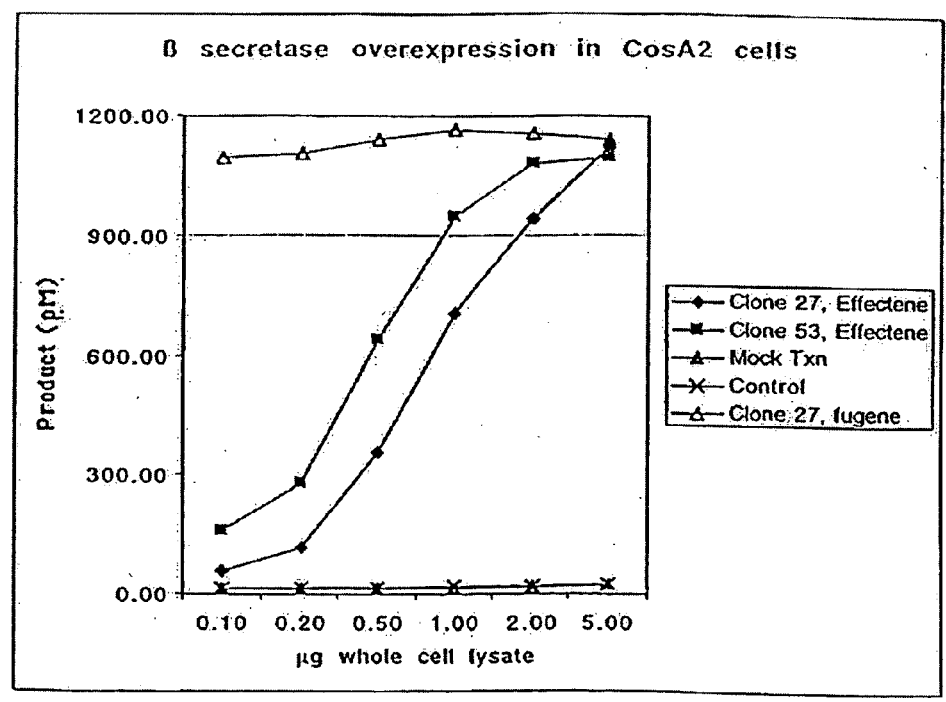

FIG. 14B

Wild-Type Sequence   ....Val-Lys-Met-Asp...
Swedish Sequence     ....Val-Asn-Leu-Asp...

β-SECRETASE ENZYME COMPOSITIONS AND METHODS

CROSS-REFERENCES TO RELATED APPLICATIONS

This application is a continuation of U.S. application Ser. No. 09/723,722, filed Nov. 28, 2000 now U.S. Pat. No. 7,115,410 (incorporated by reference), which is a continuation of U.S. application Ser. No. 09/501,708, filed Feb. 10, 2000 now abandoned (incorporated by reference), which is a continuation-in-part of U.S. application Ser. No. 09/47 1,669, filed Dec. 24, 1999, which claims the benefit under 35 U.S.C. 119(e) of U.S. Application No. 60/119,571 (incorporated by reference), filed Feb. 10, 1999, and which also claims the benefit under 35 U.S.C. 119(e) of U.S. Application No. 60/139,172 (incorporated by reference), filed Jun. 15, 1999. U.S. application Ser. No. 09/501,708 also claims the benefit under 35 U.S.C. 119(e) of U.S. Application No. 60/119,571 filed Feb. 10, 1999, and U.S. Application No. 60/139,172. The present application is also a continuation-in-part of U.S. application Ser. No. 09/471,669, filed Dec. 24, 1999, which also claims the benefit under 35 U.S.C. 119(e) of U.S. Application No. 60/119,571, filed Feb. 10, 1999, and claims the benefit under 35 U.S.C. 119(e) of U.S. Application No. 60/139,172, filed Jun. 15, 1999.

FIELD OF THE INVENTION

The invention relates to the discovery of various active forms of β-secretase, an enzyme that cleaves β-amyloid precursor protein (APP) at one of the two cleavage sites necessary to produce β-amyloid peptide (Aβ). The invention also relates to inhibitors of this enzyme, which are considered candidates for therapeutics in the treatment of amyloidogenic diseases such as Alzheimer's disease. Further aspects of the present invention include screening methods, assays, and kits for discovering such therapeutic inhibitors, as well as diagnostic methods for determining whether an individual carries a mutant form of the enzyme.

BACKGROUND OF THE INVENTION

Alzheimer's disease is characterized by the presence of numerous amyloid plaques and neurofibrillatory tangles present in the brain, particularly in those regions of the brain involved in memory and cognition. β-amyloid peptide (Aβ) is a 39–43 amino acid peptide that is major component of amyloid plaques and is produced by cleavage of a large protein known as the amyloid precursor protein (APP) at a specific site(s) within the N-terminal region of the protein. Normal processing of APP involves cleavage of the protein at point 16-17 amino acids C-terminal to the N-terminus of the β-AP region, releasing a secreted ectodomain, α-sAPP, thus precluding production of β-AP. Cleavage by β-secretase enzyme of APP between Met$^{671}$ and Asp$^{672}$ and subsequent processing at the C-terminal end of APP produces Aβ peptide, which is highly implicated in the etiology of Alzheimer's pathology (Seubert, et al., in Pharmacological Treatment of Alzheimer's disease, Wiley-Liss, Inc., pp. 345–366, 1997; Zhao, J., et al. J. Biol. Chem. 271: 31407–31411, 1996).

It is not clear whether β-secretase enzyme levels and/or activity is inherently higher than normal in Alzheimer's patients; however, it is clear that its cleavage product, Aβ peptide, is abnormally concentrated in amyloid plaques present in their brains. Therefore, it would be desirable to isolate, purify and characterize the enzyme responsible for the pathogenic cleavage of APP in order to help answer this and other questions surrounding the etiology of the disease. In particular, it is also desirable to utilize the isolated enzyme, or active fragments thereof, in methods for screening candidate drugs for ability to inhibit the activity of β-secretase. Drugs exhibiting inhibitory effects on β-secretase activity are expected to be useful therapeutics in the treatment of Alzheimer's disease and other amyloidogenic disorders characterized by deposition of Aβ peptide containing fibrils.

U.S. Pat. No. 5,744,346 (Chrysler, et al.) describes the initial isolation and partial purification of β-secretase enzyme characterized by its size (apparent molecular weight in the range of 260 to 300 kilodaltons when measured by gel exclusion chromatography) and enzymatic activity (ability to cleave the 695-amino acid isotype of β-amyloid precursor protein between amino acids 596 and 597). The present invention provides a significant improvement in the purity of β-secretase enzyme, by providing a purified β-secretase enzyme that is at least 200 fold purer than that previously described. Such a purified protein has utility in a number of applications, including crystallization for structure determination. The invention also provides methods for producing recombinant forms of β-secretase enzymes that have the same size and enzymatic profiles as the naturally occurring forms. It is a further discovery of the present invention that human β-secretase is a so-called "aspartyl" (or "aspartic") protease.

SUMMARY OF THE INVENTION

This invention is directed to a β-secretase protein that has now been purified to apparent homogeneity, and in particular to a purified protein characterized by a specific activity of at least about $0.2 \times 10^5$ and preferably at least $1.0 \times 10^5$ nM/h/μg protein in a representative β-secretase assay, the MBP-C125sw substrate assay. The resulting enzyme, which has a characteristic activity in cleaving the 695-amino acid isotype of β-amyloid precursor protein (β-APP) between amino acids 596 and 597 thereof, is at least 10,000-fold, preferably at least 20,000-fold and, more preferably in excess of 200,000-fold higher specific activiy than an activity exhibited by a solubilized but unenriched membrane fraction from human 293 cells, such as have been earlier characterized.

In one embodiment, the purified enzyme is fewer than 450 amino acids in length, comprising a polypeptide having the amino acid sequence SEQ ID NO: 70 [63–452]. In preferred embodiments, the purified protein exists in a variety of "truncated forms" relative to the proenzyme referred to herein as SEQ ID NO:2 [1–501], such as forms having amino acid sequences SEQ ID NO:70 [63–452], SEQ ID NO:69 [63–501], SEQ ID NO:67 [58–501], SEQ ID NO:68 [58–452], SEQ ID NO:58 [46–452], SEQ ID NO:74 [22–452]. More generally, it has been found that particularly useful forms of the enzyme, particularly with regard to the crystallization studies described herein, are characterized by an N-terminus at position 46 with respect to SEQ ID NO: 2 and a C-terminus between positions 452 and 470 with respect to SEQ ID NO: 2, and more particularly, by an N-terminus at position 22 with respect to SEQ ID NO: 2 and a C-terminus between positions 452 and 470 with respect to SEQ ID NO: 2. These forms are considered to be cleaved in the transmembrane "anchor" domain. Other particularly useful purified forms of the enzyme include: SEQ ID NO: 43 [46–501], SEQ ID NO: 66 [22–501], and SEQ ID NO: 2 [1–501]. More generally, it is appreciated that useful forms of the enzyme have an N-terminal residue corresponding to a residue selected from the group consisting of residues 22, 46, 58 and 63 with respect to SEQ ID NO: 2 and a C-terminus selected from a residue between positions 452 and 501 with respect to SEQ ID NO: 2 or a C-terminus between residue positions 452 and 470 with respect to SEQ ID NO: 2. Also described herein are forms of enzyme isolated from a mouse, exemplified by SEQ ID NO: 65.

This invention is further directed to a crystalline protein composition formed from a purified β-secretase protein, such as the various protein compositions described above. According to one embodiment, the purified protein is characterized by an ability to bind to the β-secretase inhibitor substrate P10-P4'staD→V which is at least equal to an ability exhibited by a protein having the amino acid sequence SEQ ID NO:71 [46–419], when the proteins are tested for binding to said substrate under the same conditions. According to another embodiment, the purified protein forming the crystallization composition is characterized by a binding affinity for the β-secretase inhibitor substrate SEQ ID NO: 72 (P10-P4'sta D→V) which is at least 1/100 of an affinity exhibited by a protein having the amino acid sequence SEQ ID NO: 43 [46–501], when said proteins are tested for binding to said substrate under the same conditions. Proteins forming the crystalline composition may be glycosylated or deglycosylated.

The invention also includes a crystalline protein composition containing a β-secretase substrate or inhibitor molecule, examples of which are provided herein, particularly exemplified by peptide-derived inhibitors such as SEQ ID NO: 78, SEQ ID NO: 72, SEQ ID NO: 81, and derivatives thereof. Generally useful inhibitors in this regard will have a $K_i$ of no more than about 50 μM to 0.5 mM.

Another aspect of the invention is directed to an isolated protein, comprising a polypeptide that (i) is fewer than about 450 amino acid residues in length, (ii) includes an amino acid sequence that is at least 90% identical to SEQ ID NO: 75 [63–423] including conservative substitutions thereof, and (iii) exhibits β-secretase activity, as evidenced by an ability to cleave a substrate selected from the group consisting of the 695 amino acid isotype of beta amyloid precursor protein (βAPP) between amino acids 596 and 597 thereof, MBP-C125wt and MBP-C125sw. Peptides which fit these criteria include, but are not limited to polypeptides which include the sequence SEQ ID NO: 75 [63–423], such as SEQ ID NO: 58 [46–452], SEQ ID NO: 58 [46–452], SEQ ID NO: 58 [46–452], SEQ ID NO: 74 [22–452], and may also include conservative substitutions within such sequences.

According to a further embodiment, the invention includes isolated protein compositions, such as those described above, in combination with a β-secretase substrate or inhibitor molecule, such as MBP-C125wt, MBP-C125sw, APP, APPsw, and β-secretase-cleavable fragments thereof. Additional β-secretase-cleavable fragments useful in this regard are described in the specification hereof. Particularly useful inhibitors include peptides derived from or including SEQ ID NO: 78, SEQ ID NO: 81 and SEQ ID NO: 72. Generally, such inhibitors will have $K_i$s of less than about 1 μM. Such inhibitors may be labeled with a detectable reporter molecule. Such labeled molecules are particularly useful, for example, in ligand binding assays.

In accordance with a further aspect, the invention includes protein compositions, such as those described above, expressed by a heterologous cell. In accordance with a further embodiment, such cells may also co-express a β-secretase substrate or inhibitor protein or peptide. One or both of the expressed molecules may be heterologous to the cell.

In a related embodiment, the invention includes antibodies that bind specifically to a β-secretase protein comprising a polypeptide that includes an amino acid sequence that is at least 90% identical to SEQ ID NO: 75 [63–423] including conservative substitutions thereof, but which lacks significant immunoreactivity with a protein a sequence selected from the group consisting of SEQ ID NO: 2 [1–501] and SEQ ID NO: 43 [46–501].

In a further related embodiment, the invention includes isolated nucleic acids comprising a sequence of nucleotides that encodes a β-secretase protein that is at least 95% identical to a protein selected from the group consisting of SEQ ID NO: 66 [22–501], SEQ ID NO: 43[46–501], SEQ ID NO: 57 [1–419], SEQ ID NO: 74 [22–452], SEQ ID NO: 58 [46–452], SEQ ID NO: 59 [1–452], SEQ ID NO: 60 [1–420], SEQ ID NO: 67 [58–501], SEQ ID NO:68 [58–452], SEQ ID NO: 69 [63–501], SEQ ID NO: 70 [63–452], SEQ ID NO: 75 [63–423], and SEQ ID NO: 71 [46–419], or a complementary sequence of any of such nucleotides. Specifically excluded from this nucleotide is a nucleic acid encoding a protein having the sequence SEQ ID NO: 2 [1–501].

Additionally, the invention includes an expression vector comprising such isolated nucleic acids operably linked to the nucleic acid with regulatory sequences effective for expression of the nucleic acid in a selected host cell, for heterologous expression. The host cells can be a eukaryotic cell, a bacterial cell, an insect cell or a yeast cell. Such cells can be used, for example, in a method of producing a recombinant β-secretase enzyme, where the method further includes subjecting an extract or cultured medium from said cell to an affinity matrix, such as a matrix formed from a β-secretase inhibitor molecule or antibody, as detailed herein.

The invention is also directed to a method of screening for compounds that inhibit Aβ production, comprising contacting a β-secretase polypeptide, such as those full-length or truncated forms described above, with (i) a test compound and (ii) a β-secretase substrate, and selecting the test compound as capable of inhibiting Aβ production if the β-secretase polypeptide exhibits less β-secretase activity in the presence of than in the absence of the test compound. Such an assay may be cell-based, with one or both of the enzyme and the substrate produced by the cell, such as the co-expression cell referred to above. Kits embodying such screening methods also form a part of the invention.

The screening method may further include administering a test compound to a mammalian subject having Alzheimer's disease or Alzheimer's disease like pathology, and selecting the compound as a therapeutic agent candidate if, following such administration, the subject maintains or improves cognitive ability or the subject shows reduced plaque burden. Preferably, such a subject is a comprising a transgene for human β-amyloid precursor protein (β-APP), such as a mouse bearing a transgene which encodes a human β-APP, including a mutant variants thereof, as exemplified in the specification.

In a related embodiment, the invention includes β-secretase inhibitor compound selected according to the methods described above. Such compounds may be is selected, for example, from a phage display selection system ("library"), such as are known in the art. According to another aspect, such libraries may be "biased" for the sequence peptide SEQ ID NO: 97 [P10-P4'D→V]. Other inhibitors include, or may be derived from peptide inhibitors herein identified, such as inhibitors SEQ ID NO: 78, SEQ ID NO: 72, SEQ ID NO: 78 and SEQ ID NO: 81.

Also forming part of the invention are knock-out mice, characterized by inactivation or deletion of an endogenous β-secretase gene, such as genes encodes a protein having at least 90% sequence identity to the sequence SEQ ID NO: 65. The deletion or inactivation may be inducible, such as by insertion of a Cre-lox expression system into the mouse genome.

According to a further related aspect, the invention includes a method of screening for drugs effective in the treatment of Alzheimer's disease or other cerebrovascular amyloidosis, characterized by Aβ deposition. According to this aspect of the invention, a mammalian subject characterized by overexpression of β-APP and/or deposition of Aβ is given a test compound selected for its ability to inhibit β-secretase activity a β-secretase protein according to claim 37. The compound is selected as a potential therapeutic drug compound, if it reduces the amount of Aβ deposition in said subject or if it maintains or improves cognitive ability in the subject. According to one preferred embodiment, the mammalian subject is a transgenic mouse bearing a transgene encoding a human β-APP or a mutant thereof.

The invention also includes a method of treating a patient afflicted with or having a predilection for Alzheimer's disease or other cerebrovascular amyloidosis. According to this aspect, the enzymatic hydrolysis of APP to Aβ is blocked by administering to the patient a pharmaceutically effective dose of a compound effective to inhibit one or more of the various forms of the enzyme described herein. According to another feature, the therapeutic compound is derived from a peptide selected from the group consisting of SEQ ID NO: 72, SEQ ID NO: 78, SEQ ID NO: 81 and SEQ ID NO: 97. Such derivation may be effected by the various phage selection systems described herein, in conjunction with the screening methods of the invention, or other such methods. Alternatively, or in addition, derivation may be achieved via rational chemistry approaches, including molecular modeling, known in the medicinal chemistry art. Such compounds will preferably be rather potent inhibitors of β-secretase enzymatic activity, evidenced by a $K_i$ of less than about 1–50 μM in a MBP-C125sw assay. Such compounds also form the basis for therapeutic drug compositions in accordance with the present invention, which may also include a pharmaceutically effective excipient.

According to yet another related aspect, the invention includes a method of diagnosing the presence of or a predilection for Alzheimer's disease in a patient. This method includes detecting the expression level of a gene comprising a nucleic acid encoding β-secretase in a cell sample from said patient, and diagnosing the patient as having or having a predilection for Alzheimer's disease, if said expression level is significantly greater than a predetermined control expression level. Detectable nucleic acids, and primers useful in such detection, are described in detail herein. Such nucleic acids may exclude a nucleic acid encoding the preproenzyme [1–501]. The invention is further directed to method of diagnosing the presence of or a predilection for Alzheimer's disease in a patient, comprising measuring β-secretase enzymatic activity in a cell sample from said patient, and diagnosing the patient as having or having a predilection for Alzheimer's disease, if said level enzymatic activity level is significantly greater than a predetermined control activity level.

The diagnostic methods may be carried out in a whole cell assay and/or on a nucleic acid derived from a cell sample of said patient.

The invention also includes a method of purifying a β-secretase protein enzyme molecule. According to this aspect, an impure sample containing β-secretase enzyme activity with an affinity matrix which includes a β-secretase inhibitor, such as the various inhibitor molecules described herein.

These and other objects and features of the invention will become more fully apparent when the following detailed description of the invention is read in conjunction with the accompanying drawings.

BRIEF DESCRIPTION OF THE FIGURES

FIG. 1A shows the sequence of a polynucleotide (SEQ ID NO: 1) which encodes human β-secretase translation product shown in FIG. 2A.

FIG. 1B shows the polynucleotide of FIG. 1A, including putative 5'- and 3'-untranslated regions (SEQ ID NO: 44).

FIG. 2A shows the amino acid sequence (SEQ ID NO: 2) of the predicted translation product of the open reading frame of the polynucleotide sequence shown in FIGS. 1A and 1B.

FIG. 2B shows the amino acid sequence of an active fragment of human β-secretase (SEQ ID NO: 43).

FIG. 3A shows the translation product that encodes an active fragment of human β-secretase, 452stop, (amino acids 1–452 with reference to SEQ ID NO: 2; SEQ ID NO: 59) including a FLAG-epitope tag (underlined; SEQ ID NO: 45) at the C-terminus.

FIG. 3B shows the amino acid sequence of a fragment of human β-secretase (amino acids 46–452 (SEQ ID NO: 58) with reference to SEQ ID NO: 2; including a FLAG-epitope tag (underlined; SEQ ID NO: 45) at the C-terminus.

FIGS. 5A-5E show the full length amino acid sequence of β-secretase 1–501 (SEQ ID NO: 2), including the ORF which encodes it (SEQ ID NO: 1), with certain features indicated, such as "active-D" sites indicating the aspartic acid active catalytic sites, a transmembrane region commencing at position 453, as well as leader ("Signal") sequence (residues 1–21; SEQ ID NO: 46) and putative pro region (residues 22–45; SEQ ID NO: 47) and where the polynucleotide region corresponding the proenzyme region corresponding to amino acids 46–501 (SEQ ID NO: 43)(nt 135–1503) is shown as SEQ ID NO: 44 and contains an internal peptide region (SEQ ID NO:56) and a transmembrane region (SEQ ID NO:62).

FIGS. 6A and 6B show images of silver-stained SDS-PAGE gels on which purified β-secretase-containing fractions were run under reducing (6A) and non-reducing (6B) conditions.

FIG. 9 shows a scheme in which primers derived from the polynucleotide (SEQ ID NO. 76 encoding N-terminus of purified naturally occurring β-secretase (SEQ ID NO. 77) were used to PCR-clone additional portions of the molecule, such as fragment SEQ ID NO. 79 encoding by nucleic acid SEQ ID NO. 98, as illustrated.

FIG. 10 shows an alignment of the amino acid sequence of human β-secretase ("Human Imapain.seq," 1–501, SEQ ID NO: 2) compared to ("pBS/mImpain H#3 cons") consensus mouse sequence: SEQ ID NO: 65.

FIG. 11A shows the nucleotide sequence (SEQ ID NO: 80) of an insert used in preparing vector pCF.

FIG. 11B shows a linear schematic of pCEK.

FIG. 14A shows a nucleotide sequence inserted into parent vector pCDNA3 (SEQ ID NO: 80).

FIG. 14B shows a plot of β-secretase activity in cell lysates from COS cells transfected with vectors derived from clones encoding β-secretase.

BRIEF DESCRIPTION OF THE SEQUENCES

This section briefly identifies the sequence identification numbers referred to herein. Number ranges shown in brackets here and throughout the specification are referenced to the amino acid sequence SEQ ID NO: 2, using conventional N→C-terminus order.

SEQ ID NO: 1 is a nucleic acid sequence that encodes human β-secretase, including an active fragment, as exemplified herein.

SEQ ID NO: 2 is the predicted translation product of SEQ ID NO: 1 [1–501].

SEQ ID NOS: 3–21 are degenerate oligonucleotide primers described in Example 1 (Table 4), designed from regions of SEQ ID NO: 2.

SEQ ID NOS: 22–41 are additional oligonucleotide primers used in PCR cloning methods described herein, shown in Table 5.

SEQ ID NO: 42 is a polynucleotide sequence that encodes the active enzyme β-secretase shown as SEQ ID NO: 43.

SEQ ID NO: 43 is the sequence of an active enzyme portion of human β-secretase, the N-terminus of which corresponds to the N-terminus of the predominant form of the protein isolated from natural sources [46–501].

SEQ ID NO: 44 is a polynucleotide which encodes SEQ ID NO: 2, including 5' and 3' untranslated regions.

SEQ ID NO: 45 is the FLAG sequence used in conjunction with certain polynucleotides.

SEQ ID NO: 46 is the putative leader region of β-secretase [1–22].

SEQ ID NO: 47 is the putative pre-pro region of β-secretase [23–45].

SEQ ID NO: 48 is the sequence of the clone pCEK C1.27 (FIGS. 13A–E).

SEQ ID NO: 49 is a nucleotide sequence of a fragment of the gene which encodes human β-secretase.

SEQ ID NO: 50 is the predicted translation product of SEQ ID NO: 49.

SEQ ID NO: 51 is a peptide sequence cleavage site of APP (Swedish mutation).

SEQ ID NOS: 52 and 53 are peptide substrates suitable for use in β-secretase assays used in the present invention.

SEQ ID NO: 54 is a peptide sequence cleavage site of APP (wild type) recognized by human β-secretase.

SEQ ID NO: 55 is amino acids 46–69 of SEQ ID NO: 2.

SEQ ID NO: 56 is an internal peptide just N-terminal to the transmembrane domain of β-secretase.

SEQ ID NO: 57 is β-secretase [1–419].

SEQ ID NO: 58 is β-secretase [46–452].

SEQ ID NO: 59 is β-secretase [1–452].

SEQ ID NO: 60 is β-secretase [1–420].

SEQ ID NO: 61 is EVM[hydroxyethylene]AEF.

Figure 5A:
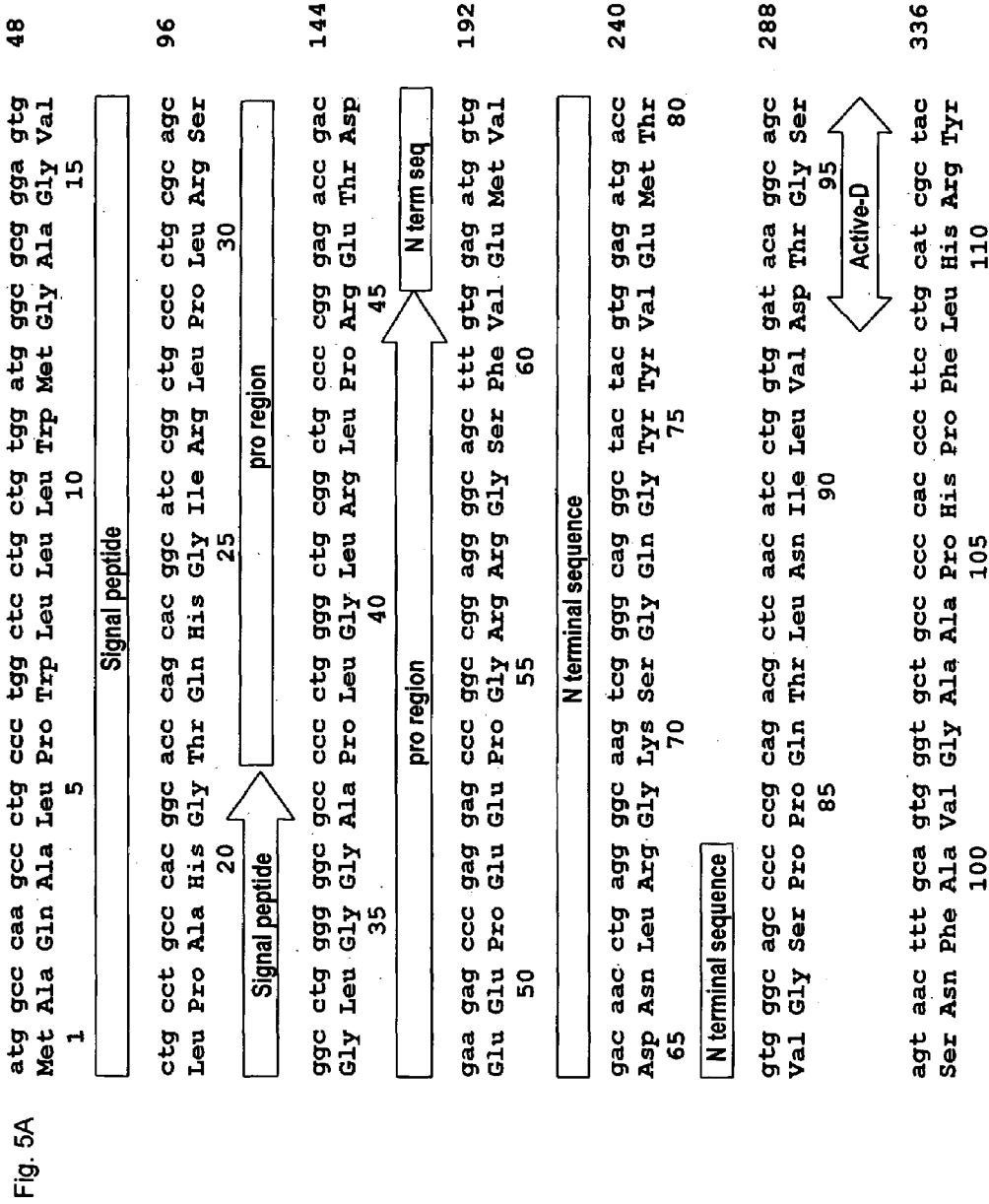

SEQ ID NO: 62 is the amino acid sequence of the transmembrane domain of β-secretase shown in (FIG. 5).

SEQ ID NO: 63 is P26-P4' of APPwt.

SEQ ID NO: 64 is P26-P1' of APPwt.

SEQ ID NO: 65 is mouse β-secretase (FIG. 10, lower sequence).

SEQ ID NO: 66 is β-secretase [22–501].

SEQ ID NO: 67 is β-secretase [58–501].

SEQ ID NO: 68 is β-secretase [58–452].

SEQ ID NO: 69 is β-secretase [63–501].

SEQ ID NO: 70 is β-secretase [63–452].

SEQ ID NO: 71 is β-secretase [46–419].

SEQ ID NO: 72 is P10-P4'staD→V.

SEQ ID NO: 73 is P4-P4'staD→V.

SEQ ID NO: 74 is β-secretase [22–452].

SEQ ID NO: 75 is β-secretase [63–423].

SEQ ID NO: 76 is nucleic acid encoding the N-terminus of naturally occuring β-secretase.

SEQ ID NO: 77 is a peptide fragment at the N-terminus of naturally occuring β-secretase.

SEQ ID NO: 78 is a P3-P4'XD→V (VMXVAEF, where X is hydroxyethlene or statine).

SEQ ID NO: 79 is a peptide fragment of naturally occuing occuring β-secretase.

SEQ ID NO: 80 is a nucleotide insert in vector pCF used herein. SEQ ID NO: 81 is P4-P4'XD→V (EVMXVAEF, where X is hydroxyethylene or statine).

SEQ ID NO: 82 is APP fragment SEVKMDAEF (P5-P4'wt).

SEQ ID NO: 83 is APP fragment SEVNLDAEF (P5-P4'sw).
SEQ ID NO: 84 is APP fragment SEVKLDAEF.
SEQ ID NO: 85 is APP fragment SEVKFDAEF.
SEQ ID NO: 86 is APP fragment SEVNFDAEF.
SEQ ID NO: 87 is APP fragment SEVKMAAEF.
SEQ ID NO: 88 is APP fragment SEVNLAAEF.
SEQ ID NO: 89 is APP fragment SEVKLAAEF.
SEQ ID NO: 90 is APP fragment SEVKMLAEF.
SEQ ID NO: 91 is APP fragment SEVNLLAEF.
SEQ ID NO: 92 is APP fragment SEVKLLAEF.
SEQ ID NO: 93 is APP fragment SEVKFAAEF.
SEQ ID NO: 94 is APP fragment SEVNFAAEF.
SEQ ID NO: 95 is APP fragment SEVKFLAEF.
SEQ ID NO: 96 is APP fragment SEVNFLAEF.
SEQ ID NO: 97 is APP-derived fragment P10-P4'(D→V): KTEEISEVNLVAEF.
SEQ ID NO: 98 is a nucleic acid fragment (FIG. 9).
SEQ ID NO: 99 is the N terminal peptide sequence of β-secretase isolated from human brain, recombinant 293T cells and recombinant Cos A2 cells (Table 3).
SEQ ID NO: 100 is the N terminal peptide sequence of a form of β-secretase isolated from recombinant 293T cells.
SEQ ID NO: 101 is the N terminal peptide sequence of a form of β-secretase isolated from recombinant 293T cells.
SEQ ID NO: 102 is the N terminal peptide sequence of a form of β-secretase isolated from recombinant CosA2 cells.
SEQ ID NO: 103 is the β-secretase cleavage sites in the wild-type APP sequence.
SEQ ID NO: 104 is the β-secretase cleavage sites in the Swedish APP sequence.

DETAILED DESCRIPTION OF THE INVENTION

I. Definitions

Unless otherwise indicated, all terms used herein have the same meaning as they would to one skilled in the art of the present invention. Practitioners are particularly directed to Sambrook, et al. (1989) Molecular Cloning: A Laboratory Manual (Second Edition), Cold Spring Harbor Press, Plainview, N.Y., and Ausubel, F. M., et al. (1998) Current Protocols in Molecular Biology, John Wiley & Sons, New York, N.Y., for definitions, terms of art and standard methods known in the art of molecular biology, particularly as it relates to the cloning protocols described herein. It is understood that this invention is not limited to the particular methodology, protocols, and reagents described, as these may be varied to produce the same result.

The terms "polynucleotide" and "nucleic acid" are used interchangeably herein and refer to a polymeric molecule having a backbone that supports bases capable of hydrogen bonding to typical polynucleotides, where the polymer backbone presents the bases in a manner to permit such hydrogen bonding in a sequence specific fashion between the polymeric molecule and a typical polynucleotide (e.g., single-stranded DNA). Such bases are typically inosine, adenosine, guanosine, cytosine, uracil and thymidine. Polymeric molecules include double and single stranded RNA and DNA, and backbone modifications thereof, for example, methylphosphonate linkages.

The term "vector" refers to a polynucleotide having a nucleotide sequence that can assimilate new nucleic acids, and propagate those new sequences in an appropriate host. Vectors include, but are not limited to recombinant plasmids and viruses. The vector (e.g., plasmid or recombinant virus) comprising the nucleic acid of the invention can be in a carrier, for example, a plasmid complexed to protein, a plasmid complexed with lipid-based nucleic acid transduction systems, or other non-viral carrier systems.

The term "polypeptide" as used herein refers to a compound made up of a single chain of amino acid residues linked by peptide bonds. The term "protein" may be synonymous with the term "polypeptide" or may refer to a complex of two or more polypeptides.

The term "modified", when referring to a polypeptide of the invention, means a polypeptide which is modified either by natural processes, such as processing or other post-translational modifications, or by chemical modification techniques which are well known in the art. Among the numerous known modifications which may be present include, but are not limited to, acetylation, acylation, amidation, ADP-ribosylation, glycosylation, GPI anchor formation, covalent attachment of a lipid or lipid derivative, methylation, myristlyation, pegylation, prenylation, phosphorylation, ubiqutination, or any similar process.

The term "β-secretase" is defined in Section III, herein.

The term "biologically active" used in conjunction with the term β-secretase refers to possession of a β-secretase enzyme activity, such as the ability to cleave β-amyloid precursor protein (APP) to produce β-amyloid peptide (Aβ).

The term "fragment," when referring to β-secretase of the invention, means a polypeptide which has an amino acid sequence which is the same as part of but not all of the amino acid sequence of full-length β-secretase polypeptide. In the context of the present invention, the full length β-secretase is generally identified as SEQ ID NO: 2, the ORF of the full-length nucleotide; however, according to a discovery of the invention, the naturally occurring active form is probably one or more N-terminal truncated versions, such as amino acids 46–501 (SEQ ID NO:43), 22–501 (SEQ ID NO:66), 58–501 (SEQ ID NO:67) or 63–501 (SEQ ID NO:69); other active forms are C-terminal truncated forms ending between about amino acids 450 and 452. The numbering system used throughout is based on the numbering of the sequence SEQ ID NO: 2.

An "active fragment" is a β-secretase fragment that retains at least one of the functions or activities of β-secretase, including but not limited to the β-secretase enzyme activity discussed above and/or ability to bind to the inhibitor substrate described herein as P10-P4'staD->V (SEQ ID NO:72). Fragments contemplated include, but are not limited to, a β-secretase fragment which retains the ability to cleave β-amyloid precursor protein to produce β-amyloid peptide. Such a fragment preferably includes at least 350, and more preferably at least 400, contiguous amino acids or conservative substitutions thereof of β-secretase, as described herein. More preferably, the fragment includes active aspartyl acid residues in the structural proximities identified and defined by the primary polypeptide structure shown as SEQ ID NO: 2 and also denoted as "Active-D" sites herein.

A "conservative substitution" refers to the substitution of an amino acid in one class by an amino acid in the same class, where a class is defined by common physicochemical amino acid sidechain properties and high substitution frequencies in homologous proteins found in nature (as determined, e.g., by a standard Dayhoff frequency exchange matrix or BLOSUM matrix). Six general classes of amino acid sidechains, categorized as described above, include: Class I (Cys); Class II (Ser, Thr, Pro, Ala, Gly); Class III (Asn, Asp, Gln, Glu); Class IV (His, Arg, Lys); Class V (Ile, Leu, Val, Met); and Class VI (Phe, Tyr, Trp). For example, substitution of an Asp for another class III residue such as Asn, Gln, or Glu, is considered to be a conservative substitution.

"Optimal alignment" is defined as an alignment giving the highest percent identity score. Such alignment can be performed using a variety of commercially available sequence analysis programs, such as the local alignment program LALIGN using a ktup of 1, default parameters and the default PAM. A preferred alignment is the pairwise alignment using the CLUSTAL-W program in MacVector, operated with default parameters, including an open gap penalty of 10.0, an extended gap penalty of 0.1, and a BLOSUM30 similarity matrix.

"Percent sequence identity," with respect to two amino acid or polynucleotide sequences, refers to the percentage of residues that are identical in the two sequences when the sequences are optimally aligned. Thus, 80% amino acid sequence identity means that 80% of the amino acids in two or more optimally aligned polypeptide sequences are identical. If a gap needs to be inserted into a first sequence to optimally align it with a second sequence, the percent identity is calculated using only the residues that are paired with a corresponding amino acid residue (i.e., the calculation does not consider residues in the second sequences that are in the "gap" of the first sequence.

A first polypeptide region is said to "correspond" to a second polypeptide region when the regions are essentially co-extensive when the sequences containing the regions are aligned using a sequence alignment program, as above. Corresponding polypeptide regions typically contain a similar, if not identical, number of residues. It will be understood, however, that corresponding regions may contain insertions or deletions of residues with respect to one another, as well as some differences in their sequences.

A first polynucleotide region is said to "correspond" to a second polynucleotide region when the regions are essentially co-extensive when the sequences containing the regions are aligned using a sequence alignment program, as above. Corresponding polynucleotide regions typically contain a similar, if not identical, number of residues. It will be understood, however, that corresponding regions may contain insertions or deletions of bases with respect to one another, as well as some differences in their sequences.

The term "sequence identity" means nucleic acid or amino acid sequence identity in two or more aligned sequences, aligned as defined above.

"Sequence similarity" between two polypeptides is determined by comparing the amino acid sequence and its conserved amino acid substitutes of one polypeptide to the sequence of a second polypeptide. Thus, 80% protein sequence similarity means that 80% of the amino acid residues in two or more aligned protein sequences are conserved amino acid residues, i.e., are conservative substitutions.

"Hybridization" includes any process by which a strand of a nucleic acid joins with a complementary nucleic acid strand through base pairing. Thus, strictly speaking, the term refers to the ability of the complement of the target sequence to bind to the test sequence, or vice-versa.

"Hybridization conditions" are based in part on the melting temperature (Tm) of the nucleic acid binding complex or probe and are typically classified by degree of "stringency" of the conditions under which hybridization is measured. The specific conditions that define various degrees of stringency (i.e., high, medium, low) depend on the nature of the polynucleotide to which hybridization is desired, particularly its percent GC content, and can be determined empirically according to methods known in the art. Functionally, maximum stringency conditions may be used to identify nucleic acid sequences having strict identity or near-strict identity with the hybridization probe; while high stringency conditions are used to identify nucleic acid sequences having about 80% or more sequence identity with the probe.

The term "gene" as used herein means the segment of DNA involved in producing a polypeptide chain; it may include regions preceding and following the coding region, e.g., 5' untranslated (5' UTR) or "leader" sequences and 3' UTR or "trailer" sequences, as well as intervening sequences (introns) between individual coding segments (exons).

The term "isolated" means that the material is removed from its original environment (e.g., the natural environment if it is naturally occurring). For example, a naturally occurring polynucleotide or polypeptide present in a living animal is not isolated, but the same polynucleotide or polypeptide, separated from some or all of the coexisting materials in the natural system, is isolated. Such isolated polynucleotides may be part of a vector and/or such polynucleotides or polypeptides may be part of a composition, such as a recombinantly produced cell (heterologous cell) expressing the polypeptide, and still be isolated in that such vector or composition is not part of its natural environment.

An "isolated polynucleotide having a sequence which encodes β-secretase" is a polynucleotide that contains the coding sequence of β-secretase, or an active fragment thereof, (i) alone, (ii) in combination with additional coding sequences, such as fusion protein or signal peptide, in which the β-secretase coding sequence is the dominant coding sequence, (iii) in combination with non-coding sequences, such as introns and control elements, such as promoter and terminator elements or 5' and/or 3' untranslated regions, effective for expression of the coding sequence in a suitable host, and/or (iv) in a vector or host environment in which the β-secretase coding sequence is a heterologous gene.

The terms "heterologous DNA," "heterologous RNA," "heterologous nucleic acid," "heterologous gene," and "heterologous polynucleotide" refer to nucleotides that are not endogenous to the cell or part of the genome in which they are present; generally such nucleotides have been added to the cell, by transfection, microinjection, electroporation, or the like. Such nucleotides generally include at least one coding sequence, but this coding sequence need not be expressed.

The term "heterologous cell" refers to a recombinantly produced cell that contains at least one heterologous DNA molecule.

A "recombinant protein" is a protein isolated, purified, or identified by virtue of expression in a heterologous cell, said cell having been transduced or transfected, either transiently or stably, with a recombinant expression vector engineered to drive expression of the protein in the host cell.

The term "expression" means that a protein is produced by a cell, usually as a result of transfection of the cell with a heterologous nucleic acid.

"Co-expression" is a process by which two or more proteins or RNA species of interest are expressed in a single cell. Co-expression of the two or more proteins is typically achieved by transfection of the cell with one or more recombinant expression vectors(s) that carry coding sequences for the proteins. In the context of the present invention, for example, a cell can be said to "co-express" two proteins, if one or both of the proteins is heterologous to the cell.

The term "expression vector" refers to vectors that have the ability to incorporate and express heterologous DNA fragments in a foreign cell. Many prokaryotic and eukaryotic expression vectors are commercially available. Selection of appropriate expression vectors is within the knowledge of those having skill in the art.

The terms "purified" or "substantially purified" refer to molecules, either polynucleotides or polypeptides, that are removed from their natural environment, isolated or separated, and are at least 90% and more preferably at least 95–99% free from other components with which they are naturally associated. The foregoing notwithstanding, such a descriptor does not preclude the presence in the same sample of splice- or other protein variants (glycosylation variants) in the same, otherwise homogeneous, sample.

A protein or polypeptide is generally considered to be "purified to apparent homogeneity" if a sample containing it shows a single protein band on a silver-stained polyacrylamide electrophoretic gel.

The term "crystallized protein" means a protein that has co-precipitated out of solution in pure crystals consisting only of the crystal, but possibly including other components that are tightly bound to the protein.

A "variant" polynucleotide sequence may encode a "variant" amino acid sequence that is altered by one or more amino acids from the reference polypeptide sequence. The variant polynucleotide sequence may encode a variant amino acid sequence, which contains "conservative" substitutions, wherein the substituted amino acid has structural or chemical properties similar to the amino acid which it replaces. In addition, or alternatively, the variant polynucleotide sequence may encode a variant amino acid sequence, which contains "non-conservative" substitutions, wherein the substituted amino acid has dissimilar structural or chemical properties to the amino acid which it replaces. Variant polynucleotides may also encode variant amino acid sequences, which contain amino acid insertions or deletions, or both. Furthermore, a variant polynucleotide may encode the same polypeptide as the reference polynucleotide sequence but, due to the degeneracy of the genetic code, has a polynucleotide sequence that is altered by one or more bases from the reference polynucleotide sequence.

An "allelic variant" is an alternate form of a polynucleotide sequence, which may have a substitution, deletion or addition of one or more nucleotides that does not substantially alter the function of the encoded polypeptide.

"Alternative splicing" is a process whereby multiple polypeptide isoforms are generated from a single gene, and involves the splicing together of nonconsecutive exons during the processing of some, but not all, transcripts of the gene. Thus, a particular exon may be connected to any one of several alternative exons to form messenger RNAs. The alternatively-spliced mRNAs produce polypeptides ("splice variants") in which some parts are common while other parts are different.

"Splice variants" of β-secretase, when referred to in the context of an mRNA transcript, are mRNAs produced by alternative splicing of coding regions, i.e., exons, from the β-secretase gene.

"Splice variants" of β-secretase, when referred to in the context of the protein itself, are β-secretase translation products that are encoded by alternatively-spliced β-secretase mRNA transcripts.

A "mutant" amino acid or polynucleotide sequence is a variant amino acid sequence, or a variant polynucleotide sequence, which encodes a variant amino acid sequence that has significantly altered biological activity or function from that of the naturally occurring protein.

A "substitution" results from the replacement of one or more nucleotides or amino acids by different nucleotides or amino acids, respectively.

The term "modulate" as used herein refers to the change in activity of the polypeptide of the invention. Modulation may relate to an increase or a decrease in biological activity, binding characteristics, or any other biological, functional, or immunological property of the molecule.

The terms "antagonist" and "inhibitor" are used interchangeably herein and refer to a molecule which, when bound to the polypeptide of the present invention, modulates the activity of enzyme by blocking, decreasing, or shortening the duration of the biological activity. An antagonist as used herein may also be referred to as a "β-secretase inhibitor" or "β-secretase blocker." Antagonists may themselves be polypeptides, nucleic acids, carbohydrates, lipids, small molecules (usually less than 1000 kD), or derivatives thereof, or any other ligand which binds to and modulates the activity of the enzyme.

β-Secretase Compositions

The present invention provides an isolated, active human β-secretase enzyme, which is further characterized as an aspartyl (aspartic) protease or proteinase, optionally, in purified form. As defined more fully in the sections that follow, β-secretase exhibits a proteolytic activity that is involved in the generation of β-amyloid peptide from β-amyloid precursor protein (APP), such as is described in U.S. Pat. No. 5,744,346, incorporated herein by reference. Alternatevely, or in addition, the β-secretase is characterized by its ability to bind, with moderately high affinity, to an inhibitor substrate described herein as P10-P4' staD→V (SEQ ID NO.: 72). According to an important feature of the present invention, a human form of β-secretase has been isolated, and its naturally occurring form has been characterized, purified and sequenced.

According to another aspect of the invention, nucleotide sequences encoding the enzyme have been identified. In addition, the enzyme has been further modified for expression in altered forms, such as truncated forms, which have similar protease activity to the naturally occurring or full length recombinant enzyme. Using the information provided herein, practitioners can isolate DNA encoding various active forms of the protein from available sources and can express the protein recombinantly in a convenient expression system. Alternatively and in addition, practitioners can purify the enzyme from natural or recombinant sources and use it in purified form to further characterize its structure and function. According to a further feature of the invention, polynucleotides and proteins of the invention are particularly useful in a variety of screening assay formats, including cell-based screening for drugs that inhibit the enzyme. Examples of uses of such assays, as well as additional utilities for the compositions are provided in Section IV, below.

β-secretase is of particular interest due to its activity and involvement in generating fibril peptide components that are the major components of amyloid plaques in the central nervous system (CNS), such as are seen in Alzheimer's disease, Down's syndrome and other CNS disorders. Accordingly, a useful feature of the present invention includes an isolated form of the enzyme that can be used, for example, to screen for inhibitory substances which are candidates for therapeutics for such disorders.

A. Isolation of Polynucleotides Encoding Human β-secretase

Polynucleotides encoding human β-secretase were obtained by PCR cloning and hybridization techniques as detailed in Examples 1–3 and described below. FIG. 1A shows the sequence of a polynucleotide (SEQ ID NO: 1) which encodes a form of human β-secretase (SEQ ID NO.: 2 [1–501]. Polynucleotides encoding human β-secretase are conveniently isolated from any of a number of human tissues, preferably tissues of neuronal origin, including but not limited to neuronal cell lines such as the commercially available human neuroblastoma cell line IMR-32 available from the American Type Culture Collection (Manassas, Va.; ATTC CCL 127) and human fetal brain, such as a human fetal brain cDNA library available from OriGene Technologies, Inc. (Rockville, Md.).

Briefly, human β-secretase coding regions were isolated by methods well known in the art, using hybridization probes derived from the coding sequence provided as SEQ ID NO: 1. Such probes can be designed and made by methods well known in the art. Exemplary probes, including degenerate probes, are described in Example 1. Alternatively, a cDNA library is screened by PCR, using, for example, the primers and conditions described in Example 2 herein. Such methods are discussed in more detail in Part B, below.

cDNA libraries were also screened using a 3'-RACE (Rapid Amplification of cDNA Ends) protocol according to methods well known in the art (White, B. A., ed., PCR Cloning Protocols; Humana Press, Totowa, N.J., 1997; shown schematically in FIG. 9). Here primers derived from the 5' portion of SEQ ID NO: 1 are added to partial cDNA substrate clone found by screening a fetal brain cDNA library as described above. A representative 3'RACE reaction used in determining the longer sequence is detailed in Example 3 and is described in more detail in Part B, below.

Human β-secretase, as well as additional members of the neuronal aspartyl protease family described herein may be identified by the use of random degenerate primers designed in accordance with any portion of the polypeptide sequence shown as SEQ ID NO: 2. For example, in experiments carried out in support of the present invention, and detailed in Example 1 herein, eight degenerate primer pools, each 8-fold degenerate, were designed based on a unique 22 amino acid peptide region selected from SEQ ID: 2. Such techniques can be used to identify further similar sequences from other species and/or representing other members of this protease family.

Preparation of Polynucleotides

The polynucleotides described herein may be obtained by screening cDNA libraries using oligonucleotide probes, which can hybridize to and/or PCR-amplify polynucleotides that encode human β-secretase, as disclosed above. cDNA libraries prepared from a variety of tissues are commercially available, and procedures for screening and isolating cDNA clones are well known to those of skill in the art. Genomic libraries can likewise be screened to obtain genomic sequences including regulatory regions and introns. Such techniques are described in, for example, Sambrook et al. (1989) Molecular Cloning: A Laboratory Manual (2nd Edition), Cold Spring Harbor Press, Plainview, N.Y. and Ausubel, F M et al. (1998) Current Protocols in Molecular Biology, John Wiley & Sons, New York, N.Y.

The polynucleotides may be extended to obtain upstream and downstream sequences such as promoters, regulatory elements, and 5' and 3' untranslated regions (UTRs). Extension of the available transcript sequence may be performed by numerous methods known to those of skill in the art, such as PCR or primer extension (Sambrook et al., supra), or by the RACE method using, for example, the MARATHON RACE kit (Cat. # K1802-1; Clontech, Palo Alto, Calif.).

Alternatively, the technique of "restriction-site" PCR (Gobinda et al. (1993) PCR Methods Applic. 2:318–22), which uses universal primers to retrieve flanking sequence adjacent a known locus, may be employed to generate additional coding regions. First, genomic DNA is amplified in the presence of primer to a linker sequence and a primer specific to the known region. The amplified sequences are subjected to a second round of PCR with the same linker primer and another specific primer internal to the first one. Products of each round of PCR are transcribed with an appropriate RNA polymerase and sequenced using reverse transcriptase.

Inverse PCR can be used to amplify or extend sequences using divergent primers based on a known region (Triglia T et al. (1988) Nucleic Acids Res 16:8186). The primers may be designed using OLIGO(R) 4.06 Primer Analysis Software (1992; National Biosciences Inc, Plymouth, Minn.), or another appropriate program, to be 22–30 nucleotides in length, to have a GC content of 50% or more, and to anneal to the target sequence at temperatures about 68–72° C. The method uses several restriction enzymes to generate a suitable fragment in the known region of a gene. The fragment is then circularized by intramolecular ligation and used as a PCR template.

Capture PCR (Lagerstrom M et al. (1991) PCR Methods Applic 1:111–19) is a method for PCR amplification of DNA fragments adjacent to a known sequence in human and yeast artificial chromosome DNA. Capture PCR also requires multiple restriction enzyme digestions and ligations to place an engineered double-stranded sequence into a flanking part of the DNA molecule before PCR.

Another method which may be used to retrieve flanking sequences is that of Parker, J D et al. (1991; Nucleic Acids Res 19:3055–60). Additionally, one can use PCR, nested primers and PromoterFinder(™) libraries to "walk in" genomic DNA (Clontech, Palo Alto, Calif.). This process avoids the need to screen libraries and is useful in finding intron/exon junctions. Preferred libraries for screening for full length cDNAs are ones that have been size-selected to include larger cDNAs. Also, random primed libraries are preferred in that they will contain more sequences which contain the 5' and upstream regions of genes. A randomly primed library may be particularly useful if an oligo d(T) library does not yield a full-length cDNA. Genomic libraries are useful for extension into the 5' nontranslated regulatory region.

The polynucleotides and oligonucleotides of the invention can also be prepared by solid-phase methods, according to known synthetic methods. Typically, fragments of up to about 100 bases are individually synthesized, then joined to form continuous sequences up to several hundred bases.

B. Isolation of β-Secretase

The amino acid sequence for a full-length human β-secretase translation product is shown as SEQ ID NO: 2 in FIG. 2A. According to the discovery of the present invention, this sequence represents a "pre pro" form of the enzyme that was deduced from the nucleotide sequence information described in the previous section in conjunction with the methods described below. Comparison of this sequence with sequences determined from the biologically active form of the enzyme purified from natural sources, as described in Part 4, below, indicate that it is likely that an active and predominant form of the enzyme is represented by sequence shown in FIG. 2B (SEQ ID NO: 43), in which the first 45 amino acids of the open-reading frame deduced sequence have been removed. This suggests that the enzyme may be post-translationally modified by proteolytic activity, which may be autocatalytic in nature. Further analysis, illustrated by the schematics shown in FIG. 5 herein, indicates that the enzyme contains a hydrophobic, putative transmembrane region near its C-terminus. As described below, a further discovery of the present invention is that the enzyme can be truncated prior to this transmembrane region and still retain β-secretase activity.

1. Purification of β-secretase from Natural and Recombinant Sources

According to an important feature of the present invention, β-secretase has now been purified from natural and recombinant sources. U.S. Pat. No. 5,744,346, incorporated herein by reference, describes isolation of β-secretase in a single peak having an apparent molecular weight of 260–300,000 (Daltons) by gel exclusion chromatography. It is a discovery of the present invention that the native enzyme can be purified to apparent homogeneity by affinity column chromatography. The methods revealed herein have been used on preparations from brain tissue as well as on preparations from 293T and recombinant cells; accordingly, these methods are believed to be generally applicable over a variety of tissue sources. The practitioner will realize that certain of the preparation steps, particularly the initial steps, may require modification to accommodate a particular tissue source and will adapt such procedures according to methods known in the art. Methods for purifying β-secretase from human brain as well as from cells are detailed in Example 5. Briefly, cell membranes or brain tissue are homogenized, fractionated, and subjected to various types of column chromatographic matrices, including wheat germ agglutinin-agarose (WGA), anion exchange chromatography and size exclusion. Activity of fractions can be measured using any appropriate assay for β-secretase activity, such as the MBP-C125 cleavage assay detailed in Example 4. Fractions containing β-secretase activity elute from this column in a peak elution volume corresponding to a size of about 260–300 kilodaltons.

Figures 6A, 6B:
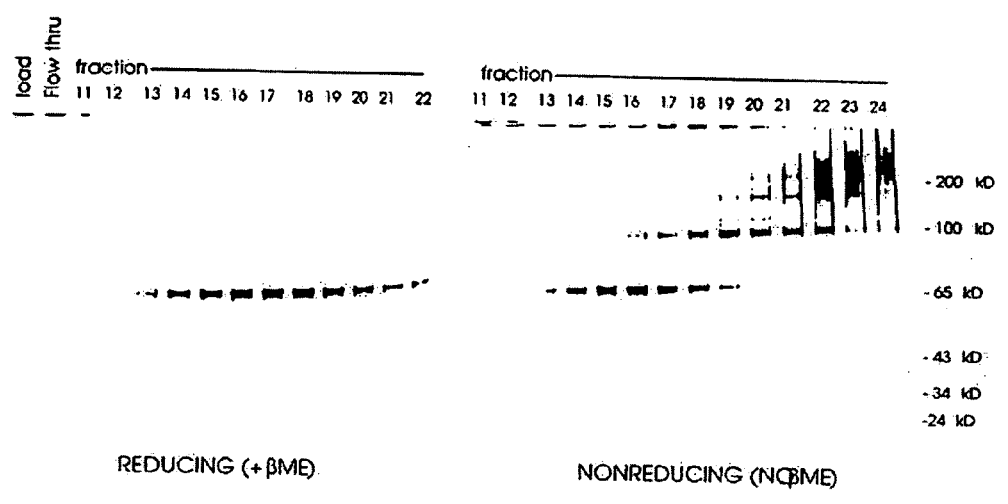

The foregoing purification scheme, which yields approximately 1,500-fold purification, is similar to that described in detail in U.S. Pat. No. 5,744,346, incorporated herein by reference. In accordance with the present invention, further purification can be achieved by applying the cation exchange flow-through material to an affinity column that employs as its affinity matrix a specific inhibitor of β-secretase, termed "P10-P4'staD->V" (NH$_2$-KTEEISEVN[sta] VAEF- CO$_2$H; SEQ ID NO.: 72). This inhibitor, and methods for making a Sepharose affinity column which incorporates it, are described in Example 7. After washing the column, β-secretase and a limited number of contaminating proteins were eluted with pH 9.5 borate buffer. The eluate was then fractionated by anion exchange HPLC, using a Mini-Q column. Fractions containing the activity peak were pooled to give the final β-secretase preparation. Results of an exemplary run using this purification scheme are summarized in Table 1. FIG. 6A shows a picture of a silver-stained SDS PAGE gel run under reducing conditions, in which β-secretase runs as a 70 kilodalton band. The same fractions run under non-reducing conditions (FIG. 6B) provide evidence for disulfide cross-linked oligomers. When the anion exchange pool fractions 18–21 (see FIG. 6B) were treated with dithiothreitol (DTT) and re-chromatographed on a Mini Q column, then subjected to SDS-PAGE under non-reducing conditions, a single band running at about 70 kilodaltons was observed. Surprisingly, the purity of this preparation is at least about 200 fold higher than the previously purified material, described in U.S. Pat. No. 5,744, 346. By way of comparison, the most pure fraction described therein exhibited a specific activity of about 253 nM/h/μg protein, taking into consideration the MW of substrate MBP-C26sw (45 kilodaltons). The present method therefore provides a preparation that is at least about 1000-fold higher purity (affinity eluate) and as high as about 6000-fold higher purity than that preparation, which represented at least 5 to 100-fold higher purity than the enzyme present in a solubilized but unenriched membrane fraction from human 293 cells.

TABLE 1

Preparation of β-secretase from Human Brain

|  | Total Activity[a] nM/h | Specific Activity[b] nM/h/μg prot. | % Yield | Purification (fold) |
|---|---|---|---|---|
| Brain Extract | 19,311,150 | 4.7 | 100 | 1 |
| WGA Eluate | 21,189,600 | 81.4 | 110 | 17 |
| Affinity Eluate | 11,175,000 | 257,500 | 53 | 54,837 |
| Anion Exchange Pool | 3,267,685 | 1,485,312 | 17 | 316,309 |

[a]Activity in MBP-C125sw assay

[b]Specific Activity = $\dfrac{\text{(Product conc. nM)(Dilution factor)}}{\text{(Enzyme sol. vol)(Incub. time h)}}$ (Enzyme conc. μg/vol)

Figure 4:
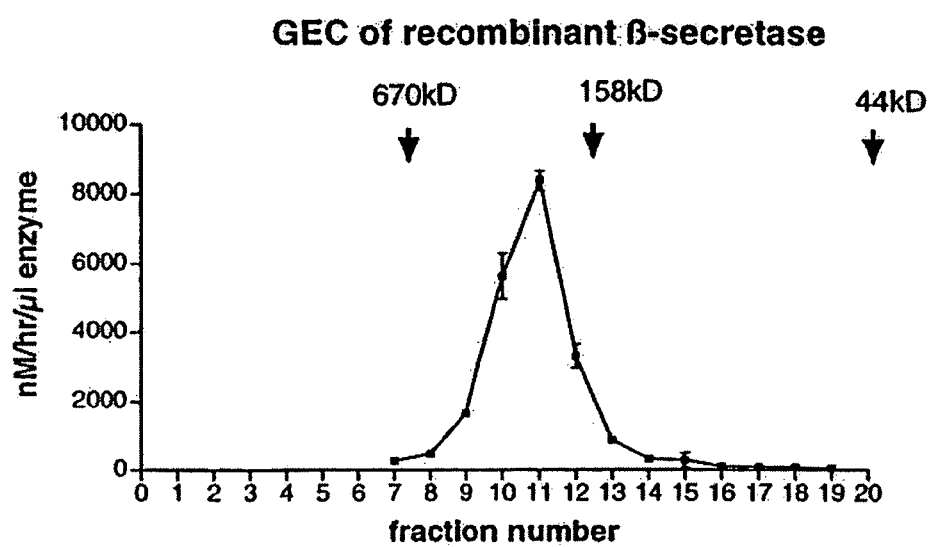
FIG. 4 shows an elution profile of recombinant β-secretase eluted from a gel filtration column.
Figure 7:
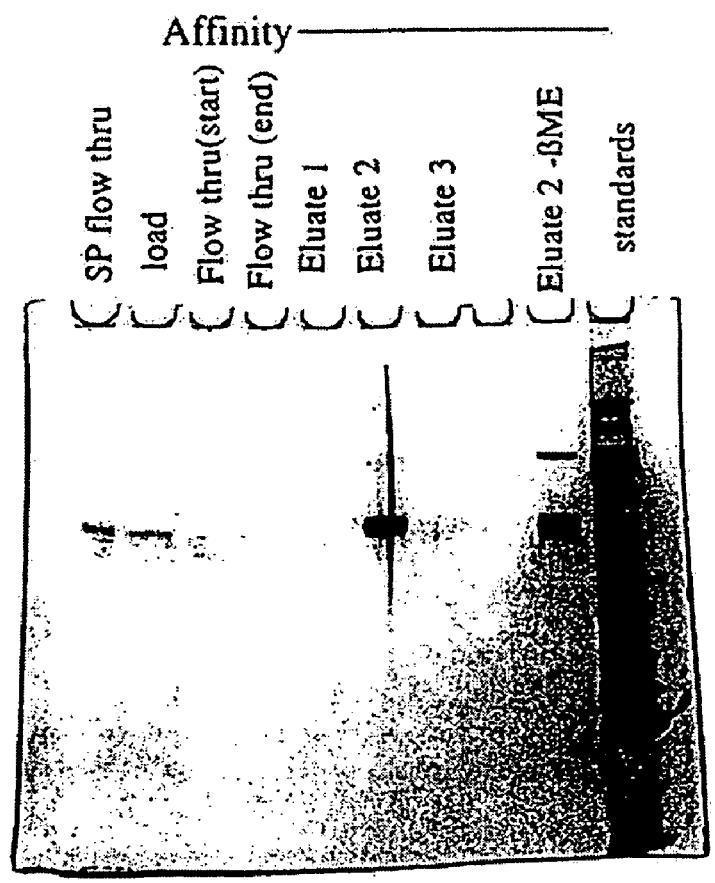
FIG. 7 shows a silver-stained SDS-PAGE of β-secretase purified from heterologous 293T cells expressing the recombinant enzyme.
Figure 8:
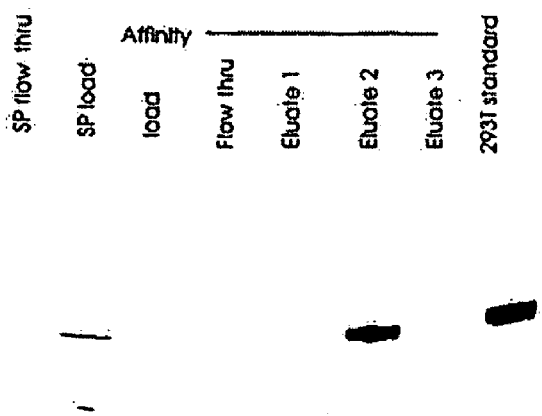
FIG. 8 shows a silver-stained SDS-PAGE of β-secretase purified from heterologous Cos A2 cells expressing the recombinant enzyme.

Example 5 also describes purification schemes used for purifying recombinant materials from heterologous cells transfected with the β-secretase coding sequence. Results from these purifications are illustrated in FIGS. 7 and 8. Further experiments carried out in support of the present invention, showed that the recombinant material has an apparent molecular weight in the range from 260,000 to 300,000 Daltons when measured by gel exclusion chromatography. FIG. 4 shows an activity profile of this preparation run on a gel exclusion chromatography column, such as a Superdex 200 (26/60) column, according to the methods described in U.S. Pat. No. 5,744,346, incorporated herein by reference.

1. Sequencing of β-secretase Protein

A schematic overview summarizing methods and results for determining the cDNA sequence encoding the N-terminal peptide sequence determined from purified β-secretase is shown in FIG. 9. N-terminal sequencing of purified β-secretase protein isolated from natural sources yielded a 21-residue peptide sequence, SEQ ID NO. 77, as described above. This peptide sequence, and its reverse translated fully degenerate nucleotide sequence, SEQ ID NO. 76, is shown in the top portion of FIG. 4. Two partially degenerate primer sets used for RT-PCR amplification of a cDNA fragment encoding this peptide are also summarized in FIG. 4. Primer set 1 consisted of DNA nucleotide primers #3427–3434, shown in Table 3 (Example 3). Matrix RT-PCR using combinations of primers from this set with cDNA reverse transcribed from primary human neuronal cultures as template yielded the predicted 54 bp cDNA product with primers #3428–3433, also described in Table 3.

In further experiments carried out in support of the present invention, it was found that oligonucleotides from primer sets 1 and 2 could also be used to amplify cDNA fragments of the predicted size from mouse brain mRNA. DNA sequence demonstrated that such primers could also be used to clone the murine homolog(s) and other species homologs of human β-secretase and/or additional members of the aspartyl protease family described herein by standard RACE-PCR technology. The sequence of a murine homolog is presented in FIG. 10 (lower sequence; "pBS/MuImPain H#3 cons"); SEQ ID NO. 65. The murine polypeptide sequence is about 95% identical to the human polypeptide sequence.

2. 5' and 3' RACE-PCR for Additional Sequence, Cloning, and mRNA Analysis

The unambiguous internal nucleotide sequence from the amplified fragment provided information which facilitated the design of internal primers matching the upper (coding) strand for 3' RACE, and lower (non-coding) strand for 5' RACE (Frohman, M. A., M. K. Dush and G. R. Martin (1988). "Rapid production of full-length cDNAs from rare transcripts amplification using a single gene specific oligo-nucleotide primer." Proc. Natl. Acad. Sci. U.S.A. 85(23): 8998–9002.) The DNA primers used for this experiment (#3459 & #3460) are illustrated schematically in FIG. 9, and the exact sequence of these primers is presented in Table 4 of Example 3.

Primers #3459 and #3476 (Table 5) were used for initial 3' RACE amplification of downstream sequences from the IMR-32 cDNA library in the vector pLPCXlox. The library had previously been sub-divided into 100 pools of 5,000 clones per pool, and plasmid DNA was isolated from each pool. A survey of the 100 pools with the primers described in Part 2, above, identified individual pools containing β-secretase clones from the library. Such clones can be used for RACE-PCR analysis.

An approximately 1.8 Kb PCR fragment was observed by agarose gel fractionation of the reaction products. The PCR product was purified from the gel and subjected to DNA sequence analysis using primer #3459 (Table 5). The resulting clone sequence, designated 23A, was determined. Six of the first seven deduced amino-acids from one of the reading frames of 23A were an exact match with the last 7 amino-acids of the N-terminal sequence (SEQ ID NO. 77) determined from the purified protein isolated from natural sources in other experiments carried out in support of this invention. This observation provided internal validation of the sequences, and defined the proper reading frame downstream. Furthermore, this DNA sequence facilitated design of additional primers for extending the sequence further downstream, verifying the sequence by sequencing the opposite strand in the upstream direction, and further facilitated isolating the cDNA clone.

A DNA sequence of human β-secretase is illustrated as SEQ ID NO: 42 corresponding to SEQ ID NO: 1 including 5'- and 3'-untranslated regions. This sequence was determined from a partial cDNA clone (9C7e.35) isolated from a commercially available human fetal brain cDNA library purchased from OriGene™, the 3' RACE product 23A, and additional clones—a total of 12 independent cDNA clones were used to determine the composite sequence. The composite sequence was assembled by sequencing overlapping stretches of DNA from both strands of the clone or PCR fragment. The predicted full length translation product is shown as SEQ ID NO: 2 in FIG. 1B.

3. Tissue Distribution of β-secretase and Related Transcripts

Oligonucleotide primer #3460 (SEQ ID NO. 39, Table 5) was employed as an end-labeled probe on Northern blots to determine the size of the transcript encoding β-secretase and to examine its expression in IMR-32 cells. Additional primers were used to isolate the mouse cDNA and to characterize mouse tissues, using Marathon RACE ready cDNA preparations (Clontech, Palo Alto, Calif.). TABLE 2 summarizes the results of experiments in which various human and murine tissues were tested for the presence of β-secretase-encoding transcripts by PCR or Northern blotting.

For example, the oligo-nucleotide probe 3460 (SEQ ID NO: 39) hybridized to a 2 Kb transcript in IMR-32 cells, indicating that the mRNA encoding the β-secretase enzyme is 2 Kb in size in this tissue. Northern blot analysis of total RNA isolated from the human T-cell line Jurkat, and human myelomonocyte line Thp1 with the 3460 oligo-nucleotide probe 3460 also revealed the presence of a 2 kb transcript in these cells.

The oligonucleotide probe #3460 also hybridizes to a ~2 kb transcript in Northern blots containing RNA from all human organs examined to date, from both adult and fetal tissue. The organs surveyed include heart, brain, liver, pancreas, placenta, lung, muscle, uterus, bladder, kidney, spleen, skin, and small intestine. In addition, certain tissues, e.g., pancreas, liver, brain, muscle, uterus, bladder, kidney, spleen and lung, show expression of larger transcripts of ~4.5 kb, 5 kb, and 6.5 kb which hybridize with oligonucleotide probe #3460.

In further experiments carried out in support of the present invention, Northern blot results were obtained with oligonucleotide probe #3460 by employing a riboprobe derived from SEQ ID NO: 1, encompassing nucleotides #155–1014. This clone provides an 860 bp riboprobe, encompassing the catalytic domain-encoding portion of β-secretase, for high stringency hybridization. This probe hybridized with high specificity to the exact match mRNA expressed in the samples being examined. Northern blots of mRNA isolated from IMR-32 and 1° HNC probed with this riboprobe revealed the presence of the 2 kb transcript previously detected with oligonucleotide #3460, as well as a novel, higher MW transcript of ~5 kb. Hybridization of RNA from adult and fetal human tissues with this 860 nt riboprobe also confirmed the result obtained with the oligonucleotide probe #3460. The mRNA encoding β-secretase is expressed in all tissues examined, predominantly as an ~5 kb transcript. In adult, its expression appeared lowest in brain, placenta, and lung, intermediate in uterus, and bladder, and highest in heart, liver, pancreas, muscle, kidney, spleen, and lung. In fetal tissue, the message is expressed uniformly in all tissues examined.

TABLE 2

Tissue distribution of human and murine β-secretase transcripts

| Tissue/Organ | Size Messages Found (Kb): Human | Mouse | Clontech Human Brain region Tissue/Organ | Human |
|---|---|---|---|---|
| Heart | 2[a] | 3.5, 3.8, 5 & 7 | Cerebellum | 2 Kb, 4 Kb, 6 Kb |
| Brain | 2, 3, 4, and 7 | 3.5, 3.8, 5 & 7 | Cerebral Cx | 2 Kb, 4 Kb, 6 Kb |
| Liver | 2, 3, 4, and 7 | 3.5, 3.8, 5 & 7 | Medulla | 2 Kb, 4 Kb, 6 Kb |
| Pancreas | 2, 3, 4, and 7 | nd[d] | Spinal Cord | 2 Kb, 4 Kb, 6 Kb |
| Placenta | 2[a], 4 and 7[b] | nd | Occipital Pole | 2 Kb, 4 Kb, 6 Kb |
| Lung | 2[a], 4 and 7[b] | 3.5, 3.8, 5 & 7 | Frontal Lobe | 2 Kb, 4 Kb, 6 Kb |
| Muscle | 2[a] and 7[b] | 3.5, 3.8, 5 & 7 | Amygdala | 2 Kb, 4 Kb, 6 Kb |
| Uterus | 2[a], 4, and 7 | nd | Caudate N. | 2 Kb, 4 Kb, 6 Kb |
| Bladder | 2[a], 3, 4, and 7 | nd | Corpus Callosum | 2 Kb, 4 Kb, 6 Kb |
| Kidney | 2[a], 3, 4, and 7 | 3.5, 3.8, 5 & 7 | Hippocampus | 2 Kb, 4 Kb, 6 Kb |
| Spleen | 2[a], 3, 4, and 7 | nd | | |
| Testis | nd | 4.5 Kb, 2 Kb | Substantia Nigra | 2 Kb, 4 Kb, 6 Kb |
| Stomach | nd | 5[a] | Thalamus | 2 Kb, 4 Kb, 6 Kb |
| Sm. Intestine | nd | 3.5, 3.8, 5 & 7 | | |
| f Brain[c] | 2[a], 3, 4, and 7 | nd | | |
| f Liver | 2[a], 3, 4, and 7 | nd | | |
| f Lung | 2[a], 3, 4, and 7 | nd | | |
| f Muscle | 2[a], 3, 4, and 7 | nd | | |
| f Heart | 2[a], 3, 4, and 7 | nd | | |
| f Kidney | 2[a], 3, 4, and 7 | nd | | |
| f Skin | 2[a], 3, 4, and 7 | nd | | |
| f Sm. Intestine | 2[a], 3, 4, and 7 | nd | | |

| Cell Line | Human | Mouse |
|---|---|---|
| IMR32 | 2[a], 5 & 7 | |
| U937 | 2[a] | |
| THP1 | 2[a] | |
| Jurkat | 2[a] | |
| HL60 | none | |
| A293 | 5 & 7 | |
| NALM6 | 5 & 7 | |
| A549 | 5 & 7 | |
| Hela | 2, 4, 5, & 7 | |
| PC12 | | 2 & 5 |
| J774 | | 5 Kb, 2 Kb |
| P388D1 ccl46 | | 5 Kb (very little), 2 Kb |
| P19 | | 5 Kb, 2 Kb |
| RBL | | 5 Kb, 2 Kb |
| EL4 | | 5 Kb, 2 Kb |

[a] by oligo 3460 probe only
[b] faint
[c] f = fetal
[d] nd = not determined

4. Active Forms of β-secretase a. N-Terminus

The full-length open reading frame (ORF) of human β-secretase is described above, and its sequence is shown in FIG. 2A as SEQ ID NO: 2. However, as mentioned above, a further discovery of the present invention indicates that the predominant form of the active, naturally occurring molecule is truncated at the N-terminus by about 45 amino acids. That is, the protein purified from natural sources was N-terminal sequenced according to methods known in the art (Argo Bioanalytica, Morris Plains, N.J.). The N-terminus yielded the following sequence: EGDEEPEEPGRRGS-FVEMVDNLRG . . . (SEQ ID NO: 55). This corresponds to amino acids 46–69 of the ORF-derived putative sequence. Based on this observation and others described below, the N-terminus of an active, naturally occurring, predominant human brain form of the enzyme is amino acid 46, with respect to SEQ ID NO: 2. Further processing of the purified protein provided the sequence of an internal peptide: IGFAVSACHVHDEFR (SEQ ID NO: 56), which is amino terminal to the putative transmembrane domain, as defined by the ORF. These peptides were used to validate and provide reading frame information for the isolated clones described elsewhere in this application.

In additional studies carried out in support of the present invention, N-terminal sequencing of β-secretase isolated from additional cell types revealed that the N-terminus may be amino acid numbers 46, 22, 58, or 63 with respect to the ORF sequence shown in FIG. 2A, depending on the tissue from which the protein is isolated, with the form having as its N-terminus amino acid 46 predominating in the tissues tested. That is, in experiments carried out in support of the present invention, the full-length β-secretase construct (i.e., encoding SEQ ID NO: 2) was transfected into 293T cells and COS A2 cells, using the Fugene technique described in Example 6. β-secretase was isolated from the cells by preparing a crude particulate fraction from the cell pellet, as described in Example 5, followed by extraction with buffer containing 0.2% Triton X-100. The Triton extract was diluted with pH 5.0 buffer and passed through a SP Sepharose column, essentially according to the methods described in Example 5A. This step removed the majority of contaminating proteins. After adjusting the pH to 4.5, β-secretase was further purified and concentrated on P10-P4'staD→V Sepharose, as described in Examples 5 and 7. Fractions were analyzed for N-terminal sequence, according to standard methods known in the art. Results are summarized in Table 3, below.

The primary N-terminal sequence of the 293T cell-derived protein was the same as that obtained from brain. In addition, minor amounts of protein starting just after the signal sequence (at Thr-22) and at the start of the aspartyl protease homology domain (Met-63) were also observed. An additional major form found in Cos A2 cells resulted from a Gly-58 cleavage.

TABLE 3

N-terminal Sequences and Amounts of β-secretase Forms in Various Cell Types

| Source | Est. Amount (pmoles) | N-terminus (Ref.: SEQ ID NO: 2) | Sequence |
|---|---|---|---|
| Human brain | 1–2 | 46 | ETDEEPEEPGR . . . (SEQ ID NO: 99) |
| Recombinant, 293T | ~35 | 46 | ETDEEPEEPGR . . . (SEQ ID NO: 99) |
|  | ~7 | 22 | TQHGIRL(P)LR . . . (SEQ ID NO: 100) |
|  | ~5 | 63 | MVDNLRGKS . . . (SEQ ID NO: 101) |
| Recombinant, CosA2 | ~4 | 46 | ETDEEPEEPGR . . . (SEQ ID NO: 99) |
|  | ~3 | 58 | GSFVEMVDNL . . . (SEQ ID NO: 102) | b. C-Terminus

Further experiments carried out in support of the present invention revealed that the C-terminus of the full-length amino acid sequence presented as SEQ ID NO: 2 can also be truncated, while still retaining β-secretase activity of the molecule. More specifically, as described in more detail in Part D below, C-terminal truncated forms of the enzyme ending just before the putative transmembrane region, i.e., at or about 10 amino acids C terminal to amino acid 452 with respect to SEQ ID NO: 2, exhibit β-secretase activity, as evidenced by an ability to cleave APP at the appropriate cleavage site and/or ability to bind SEQ ID NO. 72.

Thus, using the reference amino acid positions provided by SEQ ID NO: 2, one form of β-secretase extends from position 46 to position 501 (β-secretase 46–501; SEQ ID NO: 43). Another form extends from position 46 to any position including and beyond position 452, (β-secretase 4–452+), with a preferred form being β-secretase 46–452 (SEQ ID NO: 58). More generally, another preferred form extends from position 1 to any position including and beyond position 452, but not including position 501. Other active forms of the β-secretase protein begin at amino acid 22, 58, or 63 and may extend to any point including and beyond the cysteine at position 420, and more preferably, including and beyond position 452, while still retaining enzymatic activity (i.e., β-secretase 22–452+; β-secretase 58–452+; β-secretase 63–452+). As described in Part D, below, those forms which are truncated at a C-terminal position at or before about position 452, or even several amino acids thereafter, are particularly useful in crystallization studies, since they lack all or a significant portion of the transmembrane region, which may interfere with protein crystallization. The recombinant protein extending from position 1 to 452 has been affinity purified using the procedures described herein.

c. Crystallization of β-secretase

According to a further aspect, the present invention also includes purified β-secretase in crystallized form, in the absence or presence of binding substrates, such as peptide, modified peptide, or small molecule inhibitors. This section describes methods and utilities of such compositions.

1. Crystallization of the Protein

β-secretase purified as described above can be used as starting material to determine a crystallographic structure and coordinates for the enzyme. Such structural determinations are particularly useful in defining the conformation and size of the substrate binding site. This information can be used in the design and modeling of substrate inhibitors of the enzyme. As discussed herein, such inhibitors are candidate molecules for therapeutics for treatment of Alzheimer's disease and other amyloid diseases characterized by Aβ peptide amyloid deposits.

The crystallographic structure of β-secretase is determined by first crystallizing the purified protein. Methods for crystallizing proteins, and particularly proteases, are now well known in the art. The practitioner is referred to *Principles of Protein X-ray Crystallography* (J. Drenth, Springer Verlag, N.Y., 1999) for general principles of crystallography. Additionally, kits for generating protein crystals are generally available from commercial providers, such as Hampton Research (Laguna Niguel, Calif.). Additional guidance can be obtained from numerous research articles that have been written in the area of crystallography of protease inhibitors, especially with respect to HIV-1 and HIV-2 proteases, which are aspartic acid proteases.

Although any of the various forms of β-secretase described herein can be used for crystallization studies, particularly preferred forms lack the first 45 amino acids of the full length sequence shown as SEQ ID NO: 2, since this appears to be the predominant form which occurs naturally in human brain. It is thought that some form of post-translational modification, possibly autocatalysis, serves to remove the first 45 amino acids in fairly rapid order, since, to date, virtually no naturally occurring enzyme has been isolated with all of the first 45 amino acids intact. In addition, it is considered preferable to remove the putative transmembrane region from the molecule prior to crystallization, since this region is not necessary for catalysis and potentially could render the molecule more difficult to crystallize.

Thus, a good candidate for crystallization is β-secretase 46–452 (SEQ ID NO: 58), since this is a form of the enzyme that (a) provides the predominant naturally occurring N-terminus, and (b) lacks the "sticky" transmembrane region, while (c) retaining β-secretase activity. Alternatively, forms of the enzyme having extensions that extend part of the way (approximately 10–15 amino acids) into the transmembrane domain may also be used. In general, for determining X-ray crystallographic coordinates of the ligand binding site, any form of the enzyme can be used that either (i) exhibits β-secretase activity, and/or (ii) binds to a known inhibitor, such as the inhibitor ligand P10-P4'staD→V, with a binding affinity that is at least 1/100 the binding affinity of β-secretase

[46–501](SEQ ID NO:43) to P10-P4'staD→V (SEQ ID NO:72). Therefore, a number of additional truncated forms of the enzyme can be used in these studies. Suitability of any particular form can be assessed by contacting it with the P10-P4'staD->V affinity matrix described above. Truncated forms of the enzyme that bind to the matrix are suitable for such further analysis. Thus, in addition to 46–452, discussed above, experiments in support of the present invention have revealed that a truncated form ending in residue 419, most likely 46–419 (SEQ ID NO:71), also binds to the affinity matrix and is therefore an alternative candidate protein composition for X-ray crystallographic analysis of β-secretase. More generally, any form of the enzyme that ends before the transmembrane domain, particularly those ending between about residue 419 and 452 are suitable in this regard.

At the N-terminus, as described above, generally the first 45 amino acids will be removed during cellular processing. Other suitable naturally occurring or expressed forms are listed in Table 3 above. These include, for example, a protein commencing at residue 22, one commencing at residue 58 and one commencing at residue 63. However, analysis of the entire enzyme, starting at residue 1, can also provide information about the enzyme. Other forms, such as 1–420 (SEQ ID NO 60) to 1–452 (SEQ ID NO: 59), including intermediate forms, for example 1–440, can be useful in this regard. In general, it will also be useful to obtain structure on any subdomain of the active enzyme.

Methods for purifying the protein, including active forms, are described above. In addition, since the protein is apparently glycosylated in its naturally occurring (and mammalian-expressed recombinant) forms, it may be desirable to express the protein and purify it from bacterial sources, which do not glycosylate mammalian proteins, or express it in sources, such as insect cells, that provide uniform glycosylation patterns, in order to obtain a homogeneous composition. Appropriate vectors and codon optimization procedures for accomplishing this are known in the art.

Following expression and purification, the protein is adjusted to a concentration of about 1–20 mg/ml. In accordance with methods that have worked for other crystallized proteins, the buffer and salt concentrations present in the initial protein solution are reduced to as low a level as possible. This can be accomplished by dialyzing the sample against the starting buffer, using microdialysis techniques known in the art. Buffers and crystallization conditions will vary from protein to protein, and possibly from fragment to fragment of the active β-secretase molecule, but can be determined empirically using, for example, matrix methods for determining optimal crystallization conditions. (Drentz, J., supra; Ducruix, A., et al., eds. *Crystallization of Nucleic Acids and Proteins: A Practical Approach,* Oxford University Press, New York, 1992.)

Following dialysis, conditions are optimized for crystallization of the protein. Generally, methods for optimization may include making a "grid" of 1 μl drops of the protein solution, mixed with 1 μl well solution, which is a buffer of varying pH and ionic strength. These drops are placed in individual sealed wells, typically in a "hanging drop" configuration, for example in commercially available containers (Hampton Research, Laguna Niguel, Calif.). Precipitation/crystallization typically occurs between 2 days and 2 weeks. Wells are checked for evidence of precipitation or crystallization, and conditions are optimized to form crystals. Optimized crystals are not judged by size or morphology, but rather by the diffraction quality of crystals, which should provide better than 3 Å resolution. Typical precipitating agents include ammonium sulfate ($NH_4SO_4$), polyethylene glycol (PEG) and methyl pentane diol (MPD). All chemicals used should be the highest grade possible (e.g., ACS) and may also be re-purified by standard methods known in the art, prior to use.

Exemplary buffers and precipitants forming an empirical grid for determining crystallization conditions are commercially available. For example, the "Crystal Screen" kit (Hampton Research) provides a sparse matrix method of trial conditions that is biased and selected from known crystallization conditions for macromolecules. This provides a "grid" for quickly testing wide ranges of pH, salts, and precipitants using a very small sample (50 to 100 microliters) of macromolecule. In such studies, 1 μl of buffer/precipitant(s) solution is added to an equal volume of dialyzed protein solution, and the mixtures are allowed to sit for at least two days to two weeks, with careful monitoring of crystallization. Chemicals can be obtained from common commercial suppliers; however, it is preferable to use purity grades suitable for crystallization studies, such as are supplied by Hampton Research (Laguna Niguel, Calif.). Common buffers include Citrate, TEA, CHES, Acetate, ADA and the like (to provide a range of pH optima), typically at a concentration of about 100 mM. Typical precipitants include $(NH_4)_2SO_4$, $MgSO_4$, NaCl, MPD, Ethanol, polyethylene glycol of various sizes, isopropanol, KCl; and the like (Ducruix).

Various additives can be used to aid in improving the character of the crystals, including substrate analogs, ligands, or inhibitors, as discussed in Part 2, below, as well as certain additives, including, but not limited to:

5% Jeffamine
  5% Polypropyleneglycol P400
  5% Polyethyleneglycol 400
  5% ethyleneglycol
  5% 2-methyl-2,4-pentanediol
  5% Glycerol
  5% Dioxane
  5% dimethyl sulfoxide
  5% n-Octanol
  100 mM (NH4)2SO4
  100 mM CsCl
  100 mM CoSO4
  100 mM MnCl2
  100 mM KCl
  100 mM ZnSO4
  100 mM LiCl2
  100 mM MgCl2
  100 mM Glucose
  100 mM 1,6-Hexanediol 100 mM Dextran sulfate
  100 mM 6-amino caproic acid
  100 mM 1,6 hexane diamine
  100 mM 1,8 diamino octane
  100 mM Spermidine
  100 mM Spermine
  0.17 mM n-dodecyl-β-D-maltoside NP 40
  20 mM n-octyl-β-D-glucopyranoside According to one discovery of the present invention, the full-length β-secretase enzyme contains at least one transmembrane domain, and its purification is aided by the use of a detergent (Triton X-100). Membrane proteins can be crystallized intact, but may require specialized conditions, such as the addition of a non-ionic detergent, such as $C_8G$ (8-alkyl-β-glucoside) or an n-alkyl-maltoside ($C_nM$). Selection of such a detergent is somewhat empirical, but certain detergents are commonly employed. A number of membrane proteins have been successfully "salted out" by addition of high salt concentrations to the mixture. PEG has also been used successfully to precipitate a number of membrane proteins (Ducruix, et al., supra). Alternatively, as discussed above, a C-terminal truncated form of the protein that binds inhibitor but which lacks the transmembrane domain, such as β-secretase 46–452 (SEQ ID NO:58), is crystallized.

After crystallization conditions are determined, crystallization of a larger amount of the protein can be achieved by methods known in the art, such as vapor diffusion or equilibrium dialysis. In vapor diffusion, a drop of protein solution is equilibrated against a larger reservoir of solution containing precipitant or another dehydrating agent. After sealing, the solution equilibrates to achieve supersaturating concentrations of proteins and thereby induce crystallization in the drop.

Equilibrium dialysis can be used for crystallization of proteins at low ionic strength. Under these conditions, a phenomenon known as "salting in" occurs, whereby the protein molecules achieve balance of electrostatic charges through interactions with other protein molecules. This method is particularly effective when the solubility of the protein is low at the lower ionic strength. Various apparatuses and methods are used, including microdiffusion cells in which a dialysis membrane is attached to the bottom of a capillary tube, which may be bent at its lower portion. The final crystallization condition is achieved by slowly changing the composition of the outer solution. A variation of these methods utilizes a concentration gradient equilibrium dialysis set up. Microdiffusion cells are available from commercial suppliers such as Hampton Research (Laguna Niguel, Calif.).

Once crystallization is achieved, crystals characterized for purity (e.g., SDS-PAGE) and biological activity. Larger crystals (>0.2 mm) are preferred to increase the resolution of the X-ray diffraction, which is preferably on the order of 10–1.5 Angstroms. The selected crystals are subjected to X-ray diffraction, using a strong, monochromatic X-ray source, such as a Synchrotron source or rotating anode generator, and the resulting X-ray diffraction patterns are analyzed, using methods known in the art.

In one application, β-secretase amino acid sequence and/or X-ray diffraction data is recorded on computer readable medium, by which is meant any medium that can be read and directly acccessed by a computer. These data may be used to model the enzyme, a subdomain thereof, or a ligand thereof. Computer algorithms useful for this application are publicly and commercially available.

2. Crystallization of Protein plus Inhibitor

As mentioned above, it is advantageous to co-crystallize the protein in the presence of a binding ligand, such as inhibitor. Generally, the process for optimizing crystallization of the protein is followed, with addition of greater than 1 mM concentration of the inhibitor ligand during the precipitation phase. These crystals are also compared to crystals formed in the absence of ligand, so that measurements of the ligand binding site can be made. Alternatively, 1–2 μl of 0.1–25 mM inhibitor compound is added to the drop containing crystals grown in the absence of inhibitor in a process known as "soaking." Based on the coordinates of the binding site, further inhibitor optimization is achieved. Such methods have been used advantageously in finding new, more potent inhibitors for HIV proteases (See, e.g., Viswanadhan, V. N., et al. J. Med. Chem. 39: 705–712, 1996; Muegge, I., et al. J. Med. Chem. 42: 791–804, 1999).

One inhibitor ligand which is used in these co-crystallization and soaking experiments is P10-P4'staD->V (SEQ ID NO: 72), a statin peptide inhibitor described above. Methods for making the molecule are described herein. The inhibitor is mixed with β-secretase, and the mixture is subjected to the same optimization tests described above, concentrating on those conditions worked out for the enzyme alone. Coordinates are determined and comparisons are made between the free and ligand bound enzyme, according to methods well known in the art. Further comparisons can be made by comparing the inhibitory concentrations of the enzyme to such coordinates, such as described by Viswanadhan, et al, supra. Analysis of such comparisons provides guidance for design of further inhibitors, using this method.

D. Biological Activity of β-secretase

1. Naturally Occurring β-secretase

In studies carried out in support of the present invention, isolated, purified forms of β-secretase were tested for enzymatic activity using one or more native or synthetic substrates. For example, as discussed above, when β-secretase was prepared from human brain and purified to homogeneity using the methods described in Example 5A, a single band was observed by silver stain after electrophoresis of sample fractions from the anion exchange chromatography (last step) on an SDS-polyacrylamide gel under reducing (+β-mercaptoethanol) conditions. As summarized in Table 1, above, this fraction yielded a specific activity of approximately $1.5 \times 10^9$ nM/h/mg protein, where activity was measured by hydrolysis of MBP-C125SW.

2. Isolated Recombinant β-secretase

Various recombinant forms of the enzyme were produced and purified from transfected cells. Since these cells were made to overproduce the enzyme, it was found that the purification scheme described with respect naturally occurring forms of the enzyme (e.g., Example 5A) could be shortened, with positive results. For example, as detailed in Example 6, 293T cells were transfected with pCEKclone 27 (FIG. 12 and FIGS. 13A–E)(SEQ ID NO:48) and Cos A2 cells were transfected with pCFβA2 using "FUGENE" 6 Transfection Reagent (Roche Molecular Biochemicals Research, Indianapolis, Ind.). The vector pCF was constructed from the parent vector pCDNA3, commercially available from Invitrogen, by inserting SEQ ID NO: 80 (FIG. 11A) between the HindIII and EcoRI sites. This sequence encompasses the adenovirus major late promoter tripartite leader sequence, and a hybrid splice created from adenovirus major late region first exon and intron and a synthetically generated IgG variable region splice acceptor.

pCDNA3 was cut with restriction endonucleases HindIII and EcoRI, then blunted by filling in the ends with Klenow fragment of DNA polymerase I. The cut and blunted vector was gel purified, and ligated with isolated fragment from pED.GI. The pED fragment was prepared by digesting with PvuII and SmaI, followed by gel purification of the resulting 419 base-pair fragment, which was further screened for orientation, and confirmed by sequencing.

To create the pCEK expression vector, the expression cassette from pCF was transferred into the EBV expression vector pCEP4 (Invitrogen, Carlsbad, Calif.). pCEP 4 was cut with BglII and XbaI, filled in, and the large 9.15 kb fragment containing pBR, hygromycin, and EBV sequences) ligated to the 1.9 kb NruI to XmnI fragment of pCF containing the expression cassette (CMV, TPL/MLP/IGg splice, Sp6, SVpolyA, M13 flanking region). pCFβA2 (clone A2) contains full length β-secretase in the vector pCF. pCF vector replicates in COS and 293T cells. In each case, cells were pelleted and a crude particulate fraction was prepared from the pellet. This fraction was extracted with buffer containing 0.2% Triton X-100. The Triton extract was diluted with pH 5.0 buffer and passed through a SP Sepharose column. After the pH was adjusted to 4.5, β-secretase activity containing fractions were concentrated, with some additional purification on P10-P4'(statine)D->V Sepharose, as described for the brain enzyme. Silver staining of fractions revealed co-purified bands on the gel. Fractions corresponding to these bands were subjected to N-terminal amino acid determination. Results from these experiments revealed some heterogeneity of β-secretase species within the fractions. These species represent various forms of the enzyme; for example, from the 293T cells, the primary N-terminus is the same as that found in the brain, where (with respect to SEQ ID NO: 2) amino acid 46 is at the N-terminus. Minor amounts of protein starting just after the signal sequence (at residue 23) and at the start of the aspartyl protease homology domain (Met-63) were also observed. An additional major form of protein was found in Cos A2 cells, resulting from cleavage at Gly-58. These results are summarized in Table 3, above.

2. Comparison of Isolated, Naturally Occurring β-secretase with Recombinant β-secretase As described above, naturally occurring β-secretase derived from human brain as well as recombinant forms of the enzyme exhibit activity in cleaving APP, particularly as evidenced by activity in the MBP-C125 assay. Further, key peptide sequences from the naturally occurring form of the enzyme match portions of the deduced sequence derived from cloning the enzyme. Further confirmation that the two enzymes act identically can be taken from additional experiments in which various inhibitors were found to have very similar affinities for each enzyme, as estimated by a comparison of $IC_{50}$ values measured for each enzyme under similar assay conditions. These inhibitors were discovered in accordance with a further aspect of the invention, which is described below. Significantly, the inhibitors produce near identical $IC_{50}$ values and rank orders of potency in brain-derived and recombinant enzyme preparations, when compared in the same assay.

In further studies, comparisons were made between the full length recombinant enzyme having a C-terminal flag sequence "FLp501" (SEQ ID NO: 2, +SEQ ID NO: 45) and a recombinant enzyme truncated at position 452 "452Stop" (SEQ ID NO: 58 or SEQ ID NO: 59). Both enzymes exhibited activity in cleaving β-secretase substrates such as MBP-C125, as described above. The C-terminal truncated form of the enzyme exhibited activity in cleaving the MBP-C125sw substrate as well as the P26-P4' substrate, with similar rank order of potency for the various inhibitor drugs tested. In addition, the absolute $IC_{50}$s were comparable for the two enzymes tested with the same inhibitor. All $IC_{50}$s were less than 10 μM.

1. Cellular β-secretase

Further experiments carried out in support of the present invention have revealed that the isolated β-secretase polynucleotide sequences described herein encode β-secretase or β-secretase fragments that are active in cells. This section describes experiments carried out in support of the present invention, cells were transfected with DNA encoding β-secretase alone, or were co-transfected with DNA encoding-secretase and DNA encoding wild-type APP as detailed in Example 8.

a. Transfection with β-secretase

In experiments carried out in support of the present invention, clones containing genes expressing the full-length polypeptide (SEQ ID NO: 2) were transfected into COS cells (Fugene and Effectene methods). Whole cell lysates were prepared and various amounts of lysate were tested for β-secretase activity according to standard methods known in the art or described in Example 4 herein. FIG. 14B shows the results of these experiments. As shown, lysates prepared from transfected cells, but not from mock- or control cells, exhibited considerable enzymatic activity in the MPB-C125sw assay, indicating "overexpression" of β-secretase by these cells.

b. Co-Transfection of Cells with β-secretase and APP

Figure 12:
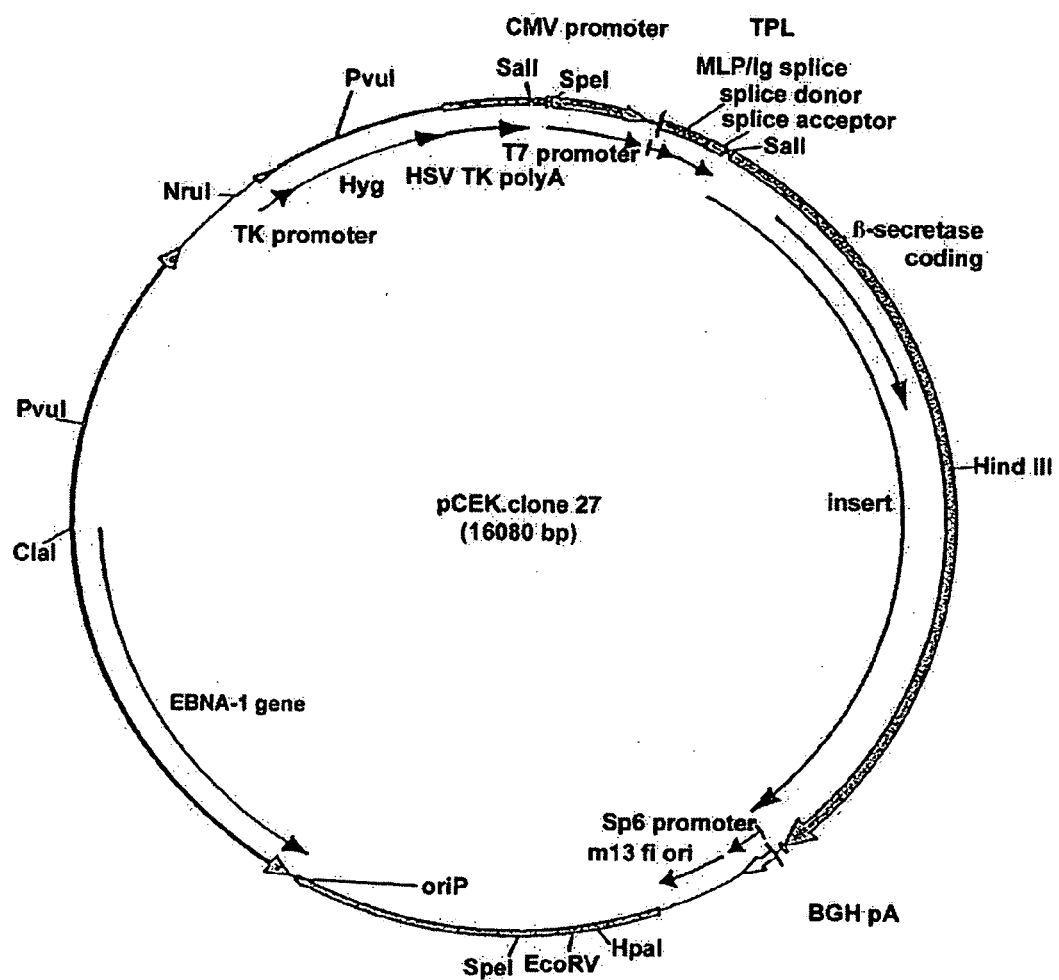
FIG. 12 shows a schematic of pCEK.clone 27 used to transfect mammalian cells with β-secretase.
Figure 13A:
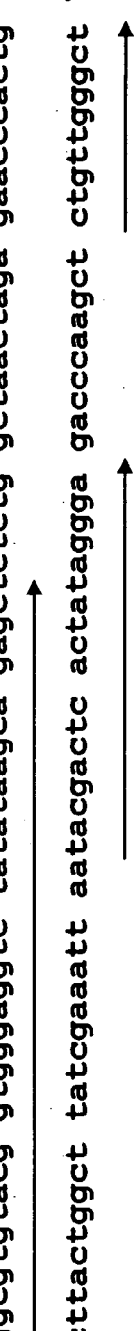
FIG. 13(A-W) show the nucleotide sequence of pCEK clone 27 (SEQ ID NO: 48), with the ORF indicated by the amino acid sequence SEQ ID NO: 2.

In further experiments, 293T cells were co-transfected with pCEK clone 27, FIGS. 12 and 13 or poCK vector containing the full length β-secretase molecule (1–501; SEQ ID NO: 2) and with a plasmid containing either the wild-type or Swedish APP construct pohCK751, as described in Example 8. β-specific cleavage was analyzed by ELISA and Western analyses to confirm that the correct site of cleavage occurs.

Figure 21:
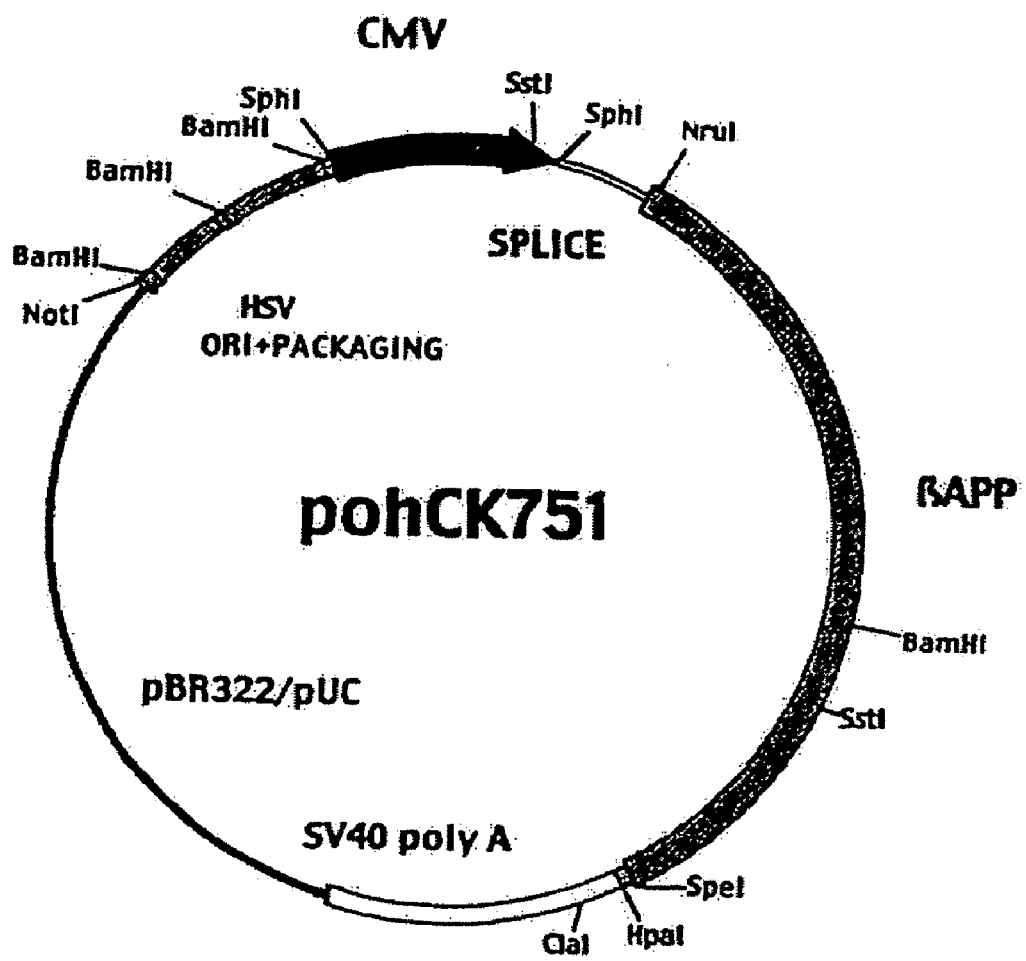
FIG. 21 shows a schematic of pohCK751 vector.

Briefly, 293T cells were co-transfected with equivalent amounts of plasmids encoding βAPPsw or wt and β-secretase or control β-galactosidase (β-gal) cDNA according to standard methods. βAPP and β-secretase cDNAs were delivered via vectors, pohCK or pCEK, which do not replicate in 293T cells (pCEK-clone 27, FIGS. 12 and 13; pohCK751 expressing βAPP 751, FIG. 21). Conditioned media and cell lysates were collected 48 hours after transfection. Western assays were carried out on conditioned media and cell lysates. ELISAs for detection of Aβ peptide were carried out on the conditioned media to analyze various APP cleavage products.

Western Blot Results

It is known that β-secretase specifically cleaves at the Met-Asp in APPwt and the Leu-Asp in APPsw to produce the Aβ peptide, starting at position 1 and releasing soluble APP (sAPPβ). Immunological reagents, specifically antibody 92 and 92sw (or 192sw), respectively, have been developed that specifically detect cleavage at this position in the APPwt and APPsw substrates, as described in U.S. Pat. No. 5,721,130, incorporated herein by reference. Western blot assays were carried out on gels on which cell lysates were separated. These assays were performed using methods well known in the art, using as primary antibody reagents Ab 92 or Ab92S, which are specific for the C terminus of the N-terminal fragment of APP derived from APPwt and APPsw, respectively. In addition, ELISA format assays were performed using antibodies specific to the N terminal amino acid of the C terminal fragment.

Figure 15A:
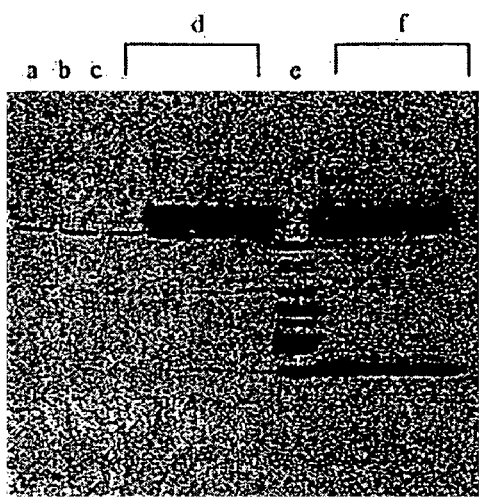
FIGS. 15A shows an image of an SDS PAGE gel loaded with triplicate samples of the lysates made from heterologous cells transfected with mutant APP (751 wt) and β-galactosidase as control (lanes d) and from cells transfected with mutant APP (751 wt) and β-secretase (lanes f) where lanes a, b, and c show lysates from untreated cells, cells transfected with β-galactosidase alone and cells transfected with β-secretase alone, respectively, and lane e indicates markers.
Figure 15B:
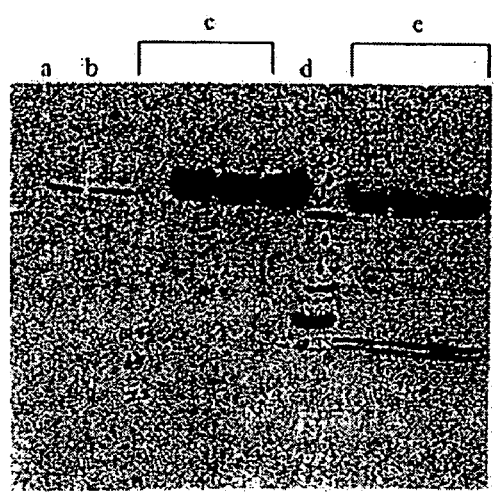
FIG. 15B shows an image an image of an SDS PAGE gel loaded with triplicate samples of the lysates made from heterologous cells transfected with mutant APP (Swedish mutation) and β-galactosidase as control (lanes c) and from cells transfected with mutant APP (Swedish mutation) and β-secretase (lanes e) where lanes a and b show lysates from cells transfected with β-galactosidase alone and cells transfected with β-secretase alone, and lane d indicates markers.

Monoclonal antibody 13G8 (specific for C-terminus of APP—epitope at positions 675–695 of APP695) was used in a Western blot format to determine whether the transfected cells express APP. FIG. 15A shows that reproducible transfection was obtained with expression levels of APP in vast excess over endogenous levels (triplicate wells are indicated as 1, 2, 3 in FIG. 15A). Three forms of APP—mature, immature and endogenous—can be seen in cells transfected with APPwt or APPsw. When β-secretase was co-transfected with APP, smaller C-terminal fragments appeared in triplicate well lanes from co-transfected cells (Western blot FIG. 15A, right-most set of lanes). In parallel experiments, where cells were co-transfected with β-secretase and APPsw substrate, literally all of the mature APP was cleaved (right-most set of lanes labeled "1,2,3" of FIG. 15B). This suggests that there is extensive cleavage by β-secretase of the mature APP (upper band), which results in C-terminal fragments of expected size in the lysate for cleavage at the β-secretase site. Co-transfection with Swedish substrate also resulted in an increase in two different sized CTF fragments (indicated by star). In conjuction with the additional Western and ELISA results described below, these results are consistent with a second cleavage occurring on the APPsw substrate after the initial cleavage at the β-secretase site.

Figure 16A:
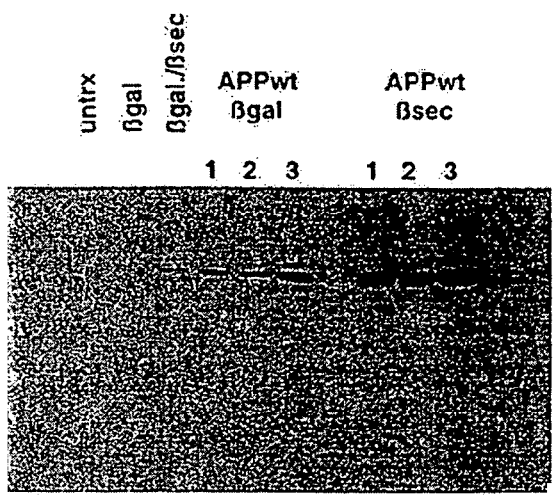
FIGS. 16A and 16B show Western blots of cell supernatants tested for presence or increase in soluble APP (sAPP).
Figure 16B:
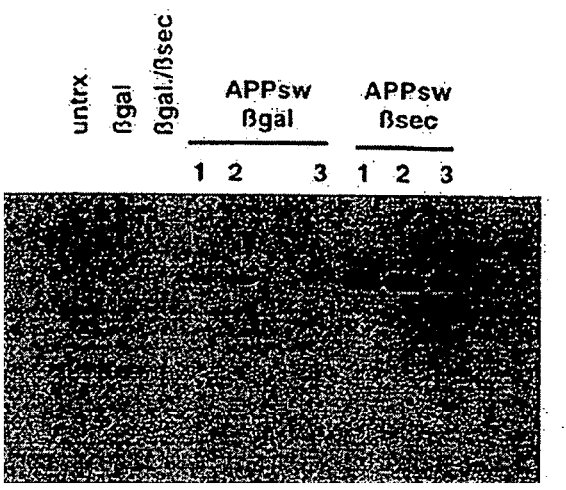

Conditioned medium from the cells was analyzed for reactivity with the 192sw antibody, which is specific for β-s-APPsw. Analysis using this antibody indicated a dramatic increase in β-secretase cleaved soluble APP. This is observed in the gel illustrated in FIG. 16B by comparing the dark bands present in the "APPsw βsec" samples to the bands present in the "APPsw βgal" samples. Antibody specific for β-s-APPwt also indicates an increase in β-secretase cleaved material, as illustrated in FIG. 16A.

Since the antibodies used in these experiments are specific for the β-secretase cleavage site, the foregoing results show that p501 β-secretase cleaves APP at this site, and the overexpression of this recombinant clone leads to a dramatic enhancement of β-secretase processing at the correct β-secretase site in whole cells. This processing works on the wildtype APP substrate and is enhanced substantially on the Swedish APP substrate. Since approximately 20% of secreted APP in 293T cells is β-sAPP, with the increase observed below for APPsw, it is probable that almost all of the sAPP is β-sAPP. This observation was further confirmed by independent Western assays in which alpha and total sAPP were measured.

Figure 17A:
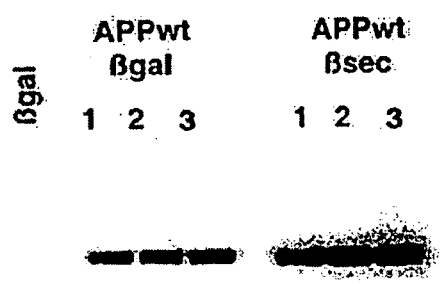
FIGS. 17A and 17B show Western blots of β-cleaved APP substrate in co-expression cells.
Figure 17B:
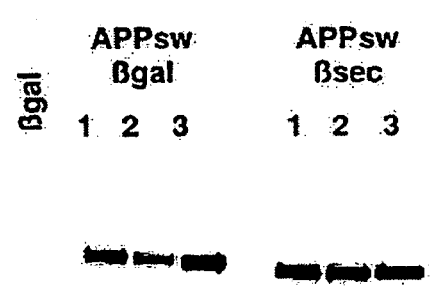

Monoclonal antibody 1736 is specific for the exposed α-secretase cleaved β-APP (Selkoe, et al.). When Western blots were performed using this antibody as primary antibody, a slight but reproducible decrease in α-cleaved APPwt was observed (FIG. 17A), and a dramatic decrease in α-cleaved APPsw material was also observed (note near absence of reactivity in FIG. 17B in the lanes labeled "APPsw βsec"). These results suggest that the overexpressed recombinant p501 β-secretase cleaves APPsw so efficiently or extensively that there is little or no substrate remaining for α-secretase to cleave. This further indicates that all the sAPP in APPsw βsec samples (illustrated in FIG. 16B) is β-sAPP.

Aβ ELISA Results

Figure 18:
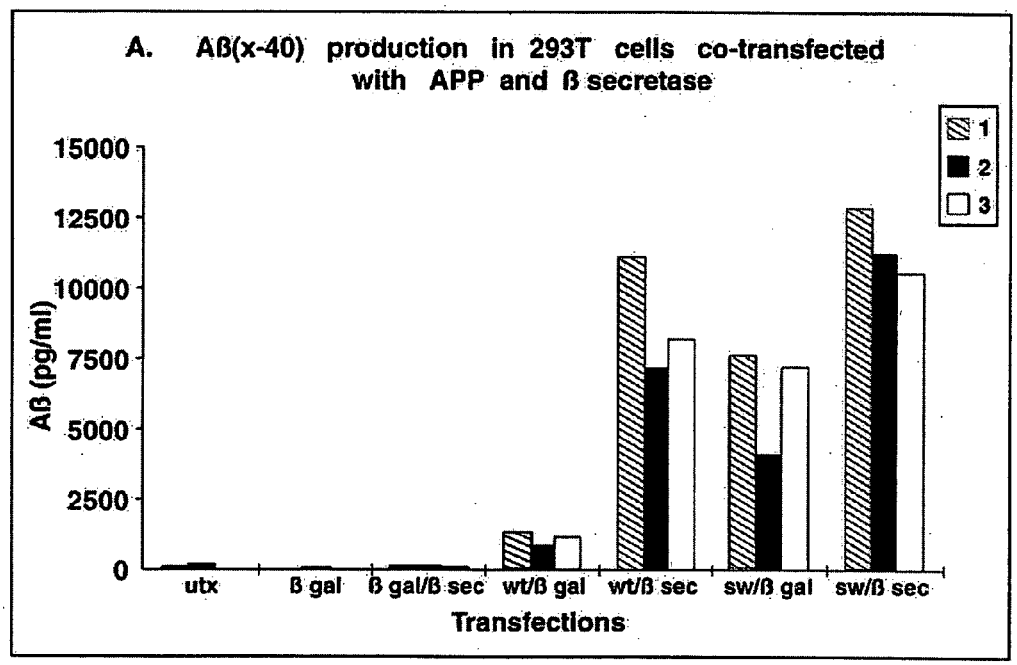
FIG. 18 shows Aβ (x-40) production in 293T cells cotransfected with APP and β-secretase.

Conditioned media from the recombinant cells was collected, diluted as necessary and tested for Aβ peptide production by ELISA on microtiter plates coated with monoclonal antibody 2G3, which is specific for recognizing the C-terminus of Aβ(1–40), with the detector reagent biotinylated mAb 3D6, which measures Aβ(x-40) (i.e., all N-terminus-truncated forms of the Aβ peptide). Overexpression of β-secretase with APPwt resulted in an approximately 8-fold increase in Aβ(x-40) production, with 1–40 representing a small percentage of the total. There was also a substantial increase in the production of Aβ1-40 (FIG. 18). With APPsw there was an approximate 2-fold increase in Aβ(x-40). Without adhering to any particular underlying theory, it is thought that the less dramatic increase of Aβ(x-40) β-sec/APPsw cells in comparison to the β-sec/APPwt cells is due in part to the fact that processing of the APPsw substrate is much more efficient than that of the APPwt substrate. That is, a significant amount of APPsw is processed by endogenous β-secretase, so further increases upon transfection of β-secretase are therefore limited. These data indicate that the expression of recombinant β-secretase increases Aβ production and that β-secretase is rate limiting for production of Aβ in cells. This means that β-secretase enzymatic activity is rate limiting for production of Aβ in cells, and therefore provides a good therapeutic target.

IV. Utility

A. Expression Vectors and Cells Expressing β-secretase

The invention includes further cloning and expression of members of the aspartyl protease family described above, for example, by inserting polynucleotides encoding the proteins into standard expression vectors and transfecting appropriate host cells according to standard methods discussed below. Such expression vectors and cells expressing, for example, the human β-secretase enzyme described herein, have utility, for example, in producing components (purified enzyme or transfected cells) for the screening assays discussed in Part B, below. Such purified enzyme also has utility in providing starting materials for crystallization of the enzyme, as described in Section III, above. In particular, truncated form(s) of the enzyme, such as 1–452 (SEQ ID NO: 59) and 46–452 (SEQ ID NO:58), and the deglycosylated forms of the enzyme described herein are considered to have utility in this regard, as are other forms truncated partway into the transmembrane region, for example amino acid residues 1–460 or 46–458 respectively in reference to SEQ ID NO:2.

In accordance with the present invention, polynucleotide sequences which encode human β-secretase, splice variants, fragments of the protein, fusion proteins, or functional equivalents thereof, collectively referred to herein as "β-secretase," may be used in recombinant DNA molecules that direct the expression of β-secretase in appropriate host cells. Due to the inherent degeneracy of the genetic code, other nucleic acid sequences that encode substantially the same or a functionally equivalent amino acid sequence may be used to clone and express β-secretase. Such variations will be readily ascertainable to persons skilled in the art.

The polynucleotide sequences of the present invention can be engineered in order to alter a β-secretase coding sequence for a variety of reasons, including but not limited to, alterations that modify the cloning, processing and/or expression of the gene product. For example, alterations may be introduced using techniques which are well known in the art, e.g., site-directed mutagenesis, to insert new restriction sites, to alter glycosylation patterns, to change codon preference, to produce splice variants, etc. For example, it may be advantageous to produce β-secretase-encoding nucleotide sequences possessing non-naturally occurring codons. Codons preferred by a particular prokaryotic or eukaryotic host (Murray, E. et al. (1989) Nuc Acids Res 17:477–508) can be selected, for example, to increase the rate of β-secretase polypeptide expression or to produce recombinant RNA transcripts having desirable properties, such as a longer half-life, than transcripts produced from naturally occurring sequence. This may be particularly useful in producing recombinant enzyme in non-mammalian cells, such as bacterial, yeast, or insect cells. The present invention also includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available. Appropriate cloning and expression vectors for use with prokaryotic and eukaryotic hosts are also described in Sambrook, et al., (supra).

The present invention also relates to host cells that are genetically engineered with vectors of the invention, and the production of proteins and polypeptides of the invention by recombinant techniques. Host cells are genetically engineered (i.e., transduced, transformed or transfected) with the vectors of this invention which may be, for example, a cloning vector or an expression vector. The vector may be, for example, in the form of a plasmid, a viral particle, a phage, etc. The engineered host cells can be cultured in conventional nutrient media modified as appropriate for activating promoters, selecting transformants or amplifying the β-secretase gene. The culture conditions, such as temperature, pH and the like, are those previously used with the host cell selected for expression, and will be apparent to those skilled in the art. Exemplary methods for transfection of various types of cells are provided in Example 6, herein.

As described above, according to a preferred embodiment of the invention, host cells can be co-transfected with an enzyme substrate, such as with APP (such as wild type or Swedish mutation form), in order to measure activity in a cell environment. Such host cells are of particular utility in the screening assays of the present invention, particularly for screening for therapeutic agents that are able to traverse cell membranes.

The polynucleotides of the present invention may be included in any of a variety of expression vectors suitable for expressing a polypeptide. Such vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, and pseudorabies. However, any other vector may be used as long as it is replicable and viable in the host. The appropriate DNA sequence may be inserted into the vector by a variety of procedures. In general, the DNA sequence is inserted into an appropriate restriction endonuclease site(s) by procedures known in the art. Such procedures and related sub-cloning procedures are deemed to be within the scope of those skilled in the art.

The DNA sequence in the expression vector is operatively linked to an appropriate transcription control sequence (promoter) to direct mRNA synthesis. Examples of such promoters include: CMV, LTR or SV40 promoter, the *E. coli* lac or trp promoter, the phage lambda PL promoter, and other promoters known to control expression of genes in prokaryotic or eukaryotic cells or their viruses. The expression vector also contains a ribosome binding site for translation initiation, and a transcription terminator. The vector may also include appropriate sequences for amplifying expression. In addition, the expression vectors preferably contain one or more selectable marker genes to provide a phenotypic trait for selection of transformed host cells such as dihydrofolate reductase or neomycin resistance for eukaryotic cell culture, or such as tetracycline or ampicillin resistance in *E. coli*.

The vector containing the appropriate DNA sequence as described above, as well as an appropriate promoter or control sequence, may be employed to transform an appropriate host to permit the host to express the protein. Examples of appropriate expression hosts include: bacterial cells, such as *E. coli, Streptomyces,* and *Salmonella typhimurium;* fungal cells, such as yeast; insect cells such as *Drosophila* and *Spodoptera* Sf9; mammalian cells such as CHO, COS, BHK, HEK 293 or Bowes melanoma; adenoviruses; plant cells, etc. It is understood that not all cells or cell lines will be capable of producing fully functional β-secretase; for example, it is probable that human β-secretase is highly glycosylated in native form, and such glycosylation may be necessary for activity. In this event, eukaryotic host cells may be preferred. The selection of an appropriate host is deemed to be within the scope of those skilled in the art from the teachings herein. The invention is not limited by the host cells employed.

In bacterial systems, a number of expression vectors may be selected depending upon the use intended for β-secretase. For example, when large quantities of β-secretase or fragments thereof are needed for the induction of antibodies, vectors, which direct high level expression of fusion proteins that are readily purified, may be desirable. Such vectors include, but are not limited to, multifunctional *E. coli* cloning and expression vectors such as Bluescript® (Stratagene, La Jolla, Calif.), in which the β-secretase coding sequence may be ligated into the vector in-frame with sequences for the amino-terminal Met and the subsequent 7 residues of beta-galactosidase so that a hybrid protein is produced; pIN vectors (Van Heeke & Schuster (1989) J Biol Chem 264:5503–5509); pET vectors (Novagen, Madison Wis.); and the like.

In the yeast *Saccharomyces cerevisiae* a number of vectors containing constitutive or inducible promoters such as alpha factor, alcohol oxidase and PGH may be used. For reviews, see Ausubel et al. (supra) and Grant et al. (1987; Methods in Enzymology 153:516–544).

In cases where plant expression vectors are used, the expression of a sequence encoding β-secretase may be driven by any of a number of promoters. For example, viral promoters such as the 35S and 19S promoters of CaMV (Brisson et al. (1984) Nature 310:511–514) may be used alone or in combination with the omega leader sequence from TMV (Takamatsu et al. (1987) EMBO J 6:307–311). Alternatively, plant promoters such as the small subunit of RUBISCO (Coruzzi et al (1984) EMBO J 3:1671–1680; Broglie et al. (1984) Science 224:838–843); or heat shock promoters (Winter J and Sinibaldi R M (1991) Results. Probl. Cell Differ. 17:85–105) may be used. These constructs can be introduced into plant cells by direct DNA transformation or pathogen-mediated transfection. For reviews of such techniques, see Hobbs S or Murry L E (1992) in McGraw Hill Yearbook of Science and Technology, McGraw Hill, New York, N.Y., pp 191–196; or Weissbach and Weissbach (1988) Methods for Plant Molecular Biology, Academic Press, New York, N.Y., pp 421–463.

β-secretase may also be expressed in an insect system. In one such system, *Autographa californica* nuclear polyhedrosis virus (AcNPV) is used as a vector to express foreign genes in *Spodoptera frugiperda* Sf9 cells or in *Trichoplusia* larvae. The β-secretase coding sequence is cloned into a nonessential region of the virus, such as the polyhedrin gene, and placed under control of the polyhedrin promoter. Successful insertion of Kv-SL coding sequence will render the polyhedrin gene inactive and produce recombinant virus lacking coat protein coat. The recombinant viruses are then used to infect *S. frugiperda* cells or *Trichoplusia* larvae in which β-secretase is expressed (Smith et al. (1983) J Virol 46:584; Engelhard E K et al. (1994) Proc Nat Acad Sci 91:3224–3227).

In mammalian host cells, a number of viral-based expression systems may be utilized. In cases where an adenovirus is used as an expression vector, a β-secretase coding sequence may be ligated into an adenovirus transcription/translation complex consisting of the late promoter and tripartite leader sequence. Insertion in a nonessential E1 or E3 region of the viral genome will result in a viable virus capable of expressing the enzyme in infected host cells (Logan and Shenk (1984) Proc Natl Acad Sci 81:3655–3659). In addition, transcription enhancers, such as the rous sarcoma virus (RSV) enhancer, may be used to increase expression in mammalian host cells.

Specific initiation signals may also be required for efficient translation of a β-secretase coding sequence. These signals include the ATG initiation codon and adjacent sequences. In cases where β-secretase coding sequence, its initiation codon and upstream sequences are inserted into the appropriate expression vector, no additional translational control signals may be needed. However, in cases where only coding sequence, or a portion thereof, is inserted, exogenous transcriptional control signals including the ATG initiation codon must be provided. Furthermore, the initiation codon must be in the correct reading frame to ensure transcription of the entire insert. Exogenous transcriptional elements and initiation codons can be of various origins, both natural and synthetic. The efficiency of expression may be enhanced by the inclusion of enhancers appropriate to the cell system in use (Scharf D et al. (1994) Results Probl Cell Differ 20:125–62; Bittner et al. (1987) Methods in Enzymol 153:516–544).

In a further embodiment, the present invention relates to host cells containing the above-described constructs. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfection, or electroporation (Davis, L., Dibner, M., and Battey, I. (1986) Basic Methods in Molecular Biology) or newer methods, including lipid transfection with "FUGENE" (Roche Molecular Biochemicals, Indianapolis, Ind.) or "EFFECTENE" (Quiagen, Valencia, Calif.), or other DNA carrier molecules. Cell-free translation systems can also be employed to produce polypeptides using RNAs derived from the DNA constructs of the present invention.

A host cell strain may be chosen for its ability to modulate the expression of the inserted sequences or to process the expressed protein in the desired fashion. Such modifications of the protein include, but are not limited to, acetylation, carboxylation, glycosylation, phosphorylation, lipidation and acylation. Post-translational processing which cleaves a "prepro" form of the protein may also be important for correct insertion, folding and/or function. For example, in the case of β-secretase, it is likely that the N-terminus of SEQ ID NO: 2 is truncated, so that the protein begins at amino acid 22, 46 or 57–58 of SEQ ID NO: 2. Different host cells such as CHO, HeLa, BHK, MDCK, 293, WI38, etc. have specific cellular machinery and characteristic mechanisms for such post-translational activities and may be chosen to ensure the correct modification and processing of the introduced, foreign protein.

For long-term, high-yield production of recombinant proteins, stable expression may be preferred. For example, cell lines that stably express β-secretase may be transformed using expression vectors which contain viral origins of replication or endogenous expression elements and a selectable marker gene. Following the introduction of the vector, cells may be allowed to grow for 1–2 days in an enriched media before they are switched to selective media. The purpose of the selectable marker is to confer resistance to selection, and its presence allows growth and recovery of cells that successfully express the introduced sequences. Resistant clumps of stably transformed cells can be proliferated using tissue culture techniques appropriate to the cell type. For example, in experiments carried out in support of the present invention, overexpression of the "452stop" form of the enzyme has been achieved.

Host cells transformed with a nucleotide sequence encoding β-secretase may be cultured under conditions suitable for the expression and recovery of the encoded protein from cell culture. The protein or fragment thereof produced by a recombinant cell may be secreted, membrane-bound, or contained intracellularly, depending on the sequence and/or the vector used. As will be understood by those of skill in the art, expression vectors containing polynucleotides encoding β-secretase can be designed with signal sequences which direct secretion of β-secretase polypeptide through a prokaryotic or eukaryotic cell membrane.

β-secretase may also be expressed as a recombinant protein with one or more additional polypeptide domains added to facilitate protein purification. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp, Seattle, Wash.). The inclusion of a protease-cleavable polypeptide linker sequence between the purification domain and β-secretase is useful to facilitate purification. One such expression vector provides for expression of a fusion protein comprising β-secretase (e.g., a soluble β-secretase fragment) fused to a polyhistidine region separated by an enterokinase cleavage site. The histidine residues facilitate purification on IMIAC (immobilized metal ion affinity chromatography, as described in Porath et al. (1992) Protein Expression and Purification 3:263–281) while the enterokinase cleavage site provides a means for isolating β-secretase from the fusion protein. pGEX vectors (Promega, Madison, Wis.) may also be used to express foreign polypeptides as fusion proteins with glutathione S-transferase (GST). In general, such fusion proteins are soluble and can easily be purified from lysed cells by adsorption to ligand-agarose beads (e.g., glutathione-agarose in the case of GST-fusions) followed by elution in the presence of free ligand.

Following transformation of a suitable host strain and growth of the host strain to an appropriate cell density, the selected promoter is induced by appropriate means (e.g., temperature shift or chemical induction) and cells are cultured for an additional period. Cells are typically harvested by centrifugation, disrupted by physical or chemical means, and the resulting crude extract retained for further purification. Microbial cells employed in expression of proteins can be disrupted by any convenient method, including freeze-thaw cycling, sonication, mechanical disruption, or use of cell lysing agents, or other methods, which are well know to those skilled in the art.

β-secretase can be recovered and purified from recombinant cell cultures by any of a number of methods well known in the art, or, preferably, by the purification scheme described herein. Protein refolding steps can be used, as necessary, in completing configuration of the mature protein. Details of methods for purifying naturally occurring as well as purified forms of β-secretase are provided in the Examples.

B. Methods of Selecting β-secretase Inhibitors

The present invention also includes methods for identifying molecules, such as synthetic drugs, antibodies, peptides, or other molecules, which have an inhibitory effect on the activity of β-secretase described herein, generally referred to as inhibitors, antagonists or blockers of the enzyme. Such an assay includes the steps of providing a human β-secretase, such as the β-secretase which comprises SEQ ID NO: 2, SEQ ID NO: 43, or more particularly in reference to the present invention, an isolated protein, about 450 amino acid residues in length, which includes an amino acid sequence that is at least 90% identical to SEQ ID NO: 75 [63–423] including conservative substitutions thereof, which exhibits β-secretase activity, as described herein. The β-secretase enzyme is contacted with a test compound to determine whether it has a modulating effect on the activity of the enzyme, as discussed below, and selecting from test compounds capable of modulating β-secretase activity. In particular, inhibitory compounds (antagonists) are useful in the treatment of disease conditions associated with amyloid deposition, particularly Alzheimer's disease. Persons skilled in the art will understand that such assays may be conveniently transformed into kits.

Particularly useful screening assays employ cells which express both β-secretase and APP. Such cells can be made recombinantly by co-transfection of the cells with polynucleotides encoding the proteins, as described in Section III, above, or can be made by transfecting a cell which naturally contains one of the proteins with the second protein. In a particular embodiment, such cells are grown up in multi-well culture dishes and are exposed to varying concentrations of a test compound or compounds for a pre-determined period of time, which can be determined empirically. Whole cell lysates, cultured media or cell membranes are assayed for β-secretase activity. Test compounds which significantly inhibit activity compared to control (as discussed below) are considered therapeutic candidates.

Isolated β-secretase, its ligand-binding, catalytic, or immunogenic fragments, or oligopeptides thereof, can be used for screening therapeutic compounds in any of a variety of drug screening techniques. The protein employed in such a test may be membrane-bound, free in solution, affixed to a solid support, borne on a cell surface, or located intracellularly. The formation of binding complexes between β-secretase and the agent being tested can be measured. Compounds that inhibit binding between β-secretase and its substrates, such as APP or APP fragments, may be detected in such an assay. Preferably, enzymatic activity will be monitored, and candidate compounds will be selected on the basis of ability to inhibit such activity. More specifically, a test compound will be considered as an inhibitor of β-secretase if the measured β-secretase activity is significantly lower than β-secretase activity measured in the absence of test compound. In this context, the term "significantly lower" means that in the presence of the test compound the enzyme displays an enzymatic activity which, when compared to enzymatic activity measured in the absence of test compound, is measurably lower, within the confidence limits of the assay method. Such measurements can be assessed by a change in $K_m$ and/or $V_{max}$, single assay endpoint analysis, or any other method standard in the art. Exemplary methods for assaying β-secretase are provided in Example 4 herein.

For example, in studies carried out in support of the present invention, compounds were selected based on their ability to inhibit β-secretase activity in the MBP-C125 assay. Compounds that inhibited the enzyme activity at a concentration lower than about 50 μM were selected for further screening.

The groups of compounds that are most likely candidates for inhibitor activity comprise a further aspect of the present invention. Based on studies carried out in support of the invention, it has been determined that the peptide compound described herein as P10-P4'staD->V (SEQ ID NO: 72) is a reasonably potent inhibitor of the enzyme. Further studies based on this sequence and peptidomimetics of portions of this sequence have revealed a number of small molecule inhibitors.

Random libraries of peptides or other compounds can also be screened for suitability as β-secretase inhibitors. Combinatorial libraries can be produced for many types of compounds that can be synthesized in a step-by-step fashion. Such compounds include polypeptides, beta-turn mimetics, polysaccharides, phospholipids, hormones, prostaglandins, steroids, aromatic compounds, heterocyclic compounds, benzodiazepines, oligomeric N-substituted glycines and oligocarbamates. Large combinatorial libraries of the compounds can be constructed by the encoded synthetic libraries (ESL) method described in Affymax, WO 95/12608, Affymax, WO 93/06121, Columbia University, WO 94/08051, Pharmacopeia, WO 95/35503 and Scripps, WO 95/30642 (each of which is incorporated by reference for all purposes).

A preferred source of test compounds for use in screening for therapeutics or therapeutic leads is a phage display library. See, e.g., Devlin, WO 91/18980; Key, B. K., et al., eds., Phage Display of Peptides and Proteins, A Laboratory Manual, Academic Press, San Diego, Calif., 1996. Phage display is a powerful technology that allows one to use phage genetics to select and amplify peptides or proteins of desired characteristics from libraries containing $10^8$-$10^9$ different sequences. Libraries can be designed for selected variegation of an amino acid sequence at desired positions, allowing bias of the library toward desired characteristics. Libraries are designed so that peptides are expressed fused to proteins that are displayed on the surface of the bacteriophage. The phage displaying peptides of the desired characteristics are selected and can be regrown for expansion. Since the peptides are amplified by propagation of the phage, the DNA from the selected phage can be readily sequenced facilitating rapid analyses of the selected peptides.

Phage encoding peptide inhibitors can be selected by selecting for phage that bind specifically to β-secretase protein. Libraries are generated fused to proteins such as gene II that are expressed on the surface of the phage. The libraries can be composed of peptides of various lengths, linear or constrained by the inclusion of two Cys amino acids, fused to the phage protein or may also be fused to additional proteins as a scaffold. One may start with libraries composed of random amino acids or with libraries that are biased to sequences in the βAPP substrate surrounding the β-secretase cleavage site or preferably, to the D→V substituted site exemplified in SEQ ID NO: 72. One may also design libraries biased toward the peptidic inhibitors and substrates described herein or biased toward peptide sequences obtained from the selection of binding phage from the initial libraries provide additional test inhibitor compound.

The β-secretase is immobilized and phage specifically binding to the β-secretase selected for. Limitations, such as a requirement that the phage not bind in the presence of a known active site inhibitor of β-secretase (e.g. the inhibitors described herein), serve to further direct phage selection active site specific compounds. This can be complicated by a differential selection format. Highly purified β-secretase, derived from brain or preferably from recombinant cells can be immobilized to 96 well plastic dishes using standard techniques (reference phage book). Recombinant β-secretase, designed to be fused to a peptide that can bind (e.g.

strepaviden binding motifs, His, FLAG or myc tags) to another protein immobilized (such as streptavidin or appropriate antibodies) on the plastic petri dishes can also be used. Phage are incubated with the bound β-secretase and unbound phage removed by washing. The phage are eluted and this selection is repeated until a population of phage binding to β-secretase is recovered. Binding and elution are carried out using standard techniques.

Alternatively β-secretase can be "bound" by expressing it in Cos or other mammalian cells growing on a petri dish. In this case one would select for phage binding to the β-secretase expressing cells, and select against phage that bind to the control cells, that are not expressing β-secretase.

One can also use phage display technology to select for preferred substrates of β-secretase, and incorporate the identified features of the preferred substrate peptides obtained by phage display into inhibitors.

In the case of β-secretase, knowledge of the amino acid sequence surrounding the cleavage site of APP and of the cleavage site of APPsw has provided information for purposes of setting up the phage display screening library to identify preferred substrates of β-secretase. As mentioned above, knowledge of the sequence of a particularly good peptide inhibitor, P10-P4staD→V (SEQ ID NO:72), as described herein, provides information for setting up a "biased" library toward this sequence.

For example, the peptide substrate library containing $10^8$ different sequences is fused to a protein (such as a gene III protein) expressed on the surface of the phage and a sequence that can be used for binding to streptavidin, or another protein, such as His tag and antibody to His. The phage are digested with protease, and undigested phage are removed by binding to appropriate immobilized binding protein, such as streptavidin. This selection is repeated until a population of phage encoding substrate peptide sequences is recovered. The DNA in the phage is sequenced to yield the substrate sequences. These substrates are then used for further development of peptidomimetics, particularly peptidomimetics having inhibitory properties.

Combinatorial libraries and other compounds are initially screened for suitability by determining their capacity to bind to, or preferably, to inhibit β-secretase activity in any of the assays described herein or otherwise known in the art. Compounds identified by such screens are then further analyzed for potency in such assays. Inhibitor compounds can then be tested for prophylactic and therapeutic efficacy in transgenic animals predisposed to an amyloidogenic disease, such as various rodents bearing a human APP-containing transgene, e.g., mice bearing a 717 mutation of APP described by Games et al., Nature 373: 523–527, 1995 and Wadsworth et al. (U.S. Pat. Nos. 5,811,633, 5,604,131, 5,720,936), and mice bearing a Swedish mutation of APP such as described by McConlogue et al. (U.S. Pat. No. 5,612,486) and Hsiao et al. (U.S. Pat. No. 5,877,399); Staufenbiel et al., Proc. Natl. Acad. Sci. USA 94, 13287–13292 (1997); Sturchler-Pierrat et al., Proc. Natl. Acad. Sci. USA 94, 13287–13292 (1997); Borchelt et al., Neuron 19, 939–945 (1997), all of which are incorporated herein by reference. Compounds or agents found to be efficacious and safe in such animal models will be further tested in standard toxicological assays. Compounds showing appropriate toxicological and pharmacokinetic profiles will be moved into human clinical trials for treatment of Alzheimer's disease and related diseases. The same screening approach can be used on other potential agents such as peptidomimetics described above.

In general, in selecting therapeutic compounds based on the foregoing assays, it is useful to determine whether the test compound has an acceptable toxicity profile, e.g., in a variety of in vitro cells and animal model(s). It may also be useful to search the tested and identified compound(s) against existing compound databases to determine whether the compound or analogs thereof have been previously employed for pharmaceutical purposes, and if so, optimal routes of administration and dose ranges. Alternatively, routes of administration and dosage ranges can be determined empirically, using methods well known in the art (see, e.g., Benet, L. Z., et al. Pharmacokinetics in *Goodman & Gilman's The Pharmacological Basis of Therapeutics*, Ninth Edition, Hardman, J. G., et al., Eds., McGraw-Hill, New York, 1966) applied to standard animal models, such as a transgenic PDAPP animal model (e.g., Games, D., et al. Nature 373: 523–527, 1995; Johnson-Wood, K., et al., Proc. Natl. Acad. Sci. USA 94: 1550–1555, 1997). To optimize compound activity and/or specificity, it may be desirable to construct a library of near-neighbor analogs to search for analogs with greater specificity and/or activity. Methods for synthesizing near-neighbor and/or targeted compound libraries are well-known in the combinatorial library field.

C. Inhibitors and Therapeutics

Part B, above, describes method of screening for compounds having β-secretase inhibitory activity. To summarize, guidance is provided for specific methods of screening for potent and selective inhibitors of β-secretase enzyme. Significantly, the practitioner is directed to specific peptide substrate/inhibitor sequences, such as P10-P4'staD→V (SEQ ID NO:72), on which drug design can be based and additional sources, such as biased phage display libraries, that should provide additional lead compounds.

The practitioner is also provided ample guidance for further refinement of the binding site of the enzyme, for example, by crystallizing the purified enzyme in accord with the methods provide herein. Noting the success in this area that has been enjoyed in the area of HIV protease inhibitor development, it is contemplated that such efforts will lead to further optimization of the test compounds described herein. With optimized compounds in hand, it is possible to define a compound pharmacophore, and further search existing pharmacophore databases, e.g., as provided by Tripos, to identify other compounds that may differ in 2-D structural formulae with the originally discovered compounds, but which share a common pharmacophore structure and activity. Test compounds are assayed in any of the inhibitor assays described herein, at various stages in development. Therefore, the present invention includes β-secretase inhibitory agents discovered by any of the methods described herein, particularly the inhibitor assays and the crystallization/optimization protocols. Such inhibitory agents are therapeutic candidates for treatment of Alzheimer's disease, as well as other amyloidoses characterized by Aβ peptide deposition. The considerations concerning therapeutic index (toxicology), bioavailability and dosage discussed in Part B above are also important to consider with respect to these therapeutic candidates.

D. Methods of Diagnosis

The present invention also provides methods of diagnosing individuals who carry mutations that provide enhanced β-secretase activity. For example, there are forms of familial Alzheimer's disease in which the underlying genetic disorder has yet to be recognized. Members of families possessing this genetic predisposition can be monitored for alterations in the nucleotide sequence that encodes β-secretase and/or promoter regions thereof, since it is apparent, in view of the teachings herein, that individuals who overexpress of the enzyme or possess catalytically more efficient forms of the enzyme would be likely to produce relatively more Aβ peptide. Support for this supposition is provided by the observation, reported herein, that the amount of β-secretase enzyme is rate limiting for production of Aβ in cells.

More specifically, persons suspected to have a predilection for developing for developing or who already have the disease, as well as members of the general population, may be screened by obtaining a sample of their cells, which may be blood cells or fibroblasts, for example, and testing the samples for the presence of genetic mutations in the β-secretase gene, in comparison to SEQ ID NO: 1 described herein, for example. Alternatively or in addition, cells from such individuals can be tested for β-secretase activity. According to this embodiment, a particular enzyme preparation might be tested for increased affinity and/or Vmax with respect to a β-secretase substrate such as MBP-C125, as described herein, with comparisons made to the normal range of values measured in the general population. Individuals whose β-secretase activity is increased compared to normal values are susceptible to developing Alzheimer's disease or other amyloidogenic diseases involving deposition of Aβ peptide.

E. Therapeutic Animal Models

A further utility of the present invention is in creation of certain transgenic and/or knockout animals that are also useful in the screening assays described herein. Of particular use is a transgenic animal that overexpresses the β-secretase enzyme, such as by adding an additional copy of the mouse enzyme or by adding the human enzyme. Such an animal can be made according to methods well known in the art (e.g., Cordell, U.S. Pat. No. 5,387,742; Wadsworth et al., U.S. Pat. Nos. 5,811,633, 5,604,131, 5,720,936; McConlogue et al., U.S. Pat. No. 5,612,486; Hsiao et al., U.S. Pat. No. 5,877,399; and "Manipulating the Mouse Embryo, A Laboratory Manual," B. Hogan, F. Costantini and E. Lacy, Cold Spring Harbor Press, 1986)), substituting the one or more of the constructs described with respect to β-secretase, herein, for the APP constructs described in the foregoing references, all of which are incorporated by reference.

An overexpressing β-secretase transgenic mouse will make higher levels of Aβ and sβAPP from APP substrates than a mouse expressing endogenous β-secretase. This would facilitate analysis of APP processing and inhibition of that processing by candidate therapeutic agents. The enhanced production of Aβ peptide in mice transgenic for β-secretase would allow acceleration of AD-like pathology seen in APP transgenic mice. This result can be achieved by either crossing the β-secretase expressing mouse onto a mouse displaying AD-like pathology (such as the PDAPP or Hsiao mouse) or by creating a transgenic mouse expressing both the β-secretase and APP transgene.

Such transgenic animals are used to screen for β-secretase inhibitors, with the advantage that they will test the ability of such inhibitors to gain entrance to the brain and to effect inhibition in vivo.

Another animal model contemplated by the present invention is a so-called "knock-out mouse" in which the endogenous enzyme is either permanently (as described in U.S. Pat. Nos. 5,464,764, 5,627,059 and 5,631,153, which are incorporated by reference in their entity) or inducibly deleted (as described in U.S. Pat. No. 4,959,317, which is incorporated by reference in its entity), or which is inactivated, as described in further detail below. Such mice serve as controls for β-secretase activity and/or can be crossed with APP mutant mice, to provide validation of the pathological sequelae. Such mice can also provide a screen for other drug targets, such as drugs specifically directed at Aβ deposition events.

β-secretase knockout mice provide a model of the potential effects of β-secretase inhibitors in vivo. Comparison of the effects of β-secretase test inhibitors in vivo to the phenotype of the β-secretase knockout can help guide drug development. For example, the phenotype may or may not include pathologies seen during drug testing of β-secretase inhibitors. If the knockout does not show pathologies seen in the drug-treated mice, one could infer that the drug is interacting non-specifically with another target in addition to the β-secretase target. Tissues from the knockout can be used to set up drug binding assays or to carry out expression cloning to find the targets that are responsible for these toxic effects. Such information can be used to design further drugs that do not interact with these undesirable targets. The knockout mice will facilitate analyses of potential toxicities that are inherent to β-secretase inhibition. Knowledge of potential toxicities will help guide the design of design drugs or drug-delivery systems to reduce such toxicities. Inducible knockout mice are particularly useful in distinguishing toxicity in an adult animal from embryonic effects seen in the standard knockout. If the knockout confers fetal-lethal effects, the inducible knockout will be advantageous.

Methods and technology for developing knock-out mice have matured to the point that a number of commercial enterprises generate such mice on a contract basis (e.g., Lexicon Genetics, Woodland Tex.; Cell & Molecular Technologies, Lavallette, N.J.; Crysalis, DNX Transgenic Sciences, Princeton, N.J.). Methodologies are also available in the art. (See Galli-Taliadoros, L. A., et al., J. Immunol. Meth. 181: 1–15, 1995). Briefly, a genomic clone of the enzyme of interest is required. Where, as in the present invention, the exons encoding the regions of the protein have been defined, it is possible to achieve inactivation of the gene without further knowledge of the regulatory sequences controlling transcription. Specifically, a mouse strain 129 genomic library can be screened by hybridization or PCR, using the sequence information provided herein, according to methods well known in the art. (Ausubel; Sambrook) The genomic clone so selected is then subjected to restriction mapping and partial exonic sequencing for confirmation of mouse homologue and to obtain information for knock-out vector construction. Appropriate regions are then sub-cloned into a "knock-out" vector carrying a selectable marker, such as a vector carrying a neo$^r$ cassette, which renders cells resistant to aminoglycoside antibiotics such as gentamycin. The construct is further engineered for disruption of the gene of interest, such as by insertion of a sequence replacement vector, in which a selectable marker is inserted into an exon of the gene, where it serves as a mutagen, disrupting the coordinated transcription of the gene. Vectors are then engineered for transfection into embryonic stem (ES) cells, and appropriate colonies are isolated. Positive ES cell clones are micro-injected into isolated host blastocysts to generate chimeric animals, which are then bred and screened for germline transmission of the mutant allele.

According to a further preferred embodiment, β-secretase knock-out mice can be generated such that the mutation is inducible, such as by inserting in the knock-out mice a lox region flanking the β-secretase gene region. Such mice are then crossed with mice bearing a "Cre" gene under an inducible promoter, resulting in at least some off-spring bearing both the "Cre" and the lox constructs. When expression of "Cre" is induced, it serves to disrupt the gene flanked by the lox constructs. Such a "Cre-lox" mouse is particularly useful, when it is suspected that the knock-out mutation may be lethal. In addition, it provides the opportunity for knocking out the gene in selected tissues, such as the brain. Methods for generating Cre-lox constructs are provided by U.S. Pat. No. 4,959,317, incorporated herein by reference, and are made on a contractual basis by Lexicon Genetics, Woodlands, Tex., among others.

The following examples illustrate, but in no way are intended to limit the present invention.

EXAMPLE 1

Isolation of Coding Sequences for Human β-secretase

A. PCR Cloning

Poly A+ RNA from IMR human neuroblastoma cells was reverse transcribed using the Perkin-Elmer kit. Eight degenerate primer pools, each 8 fold degenerate, encoding the N and C terminal portions of the amino acid sequence obtained from the purified protein were designed (shown in Table 4; oligos 3407 through 3422)(SEQ ID NOS:3–21). PCR reactions were composed of cDNA from 10 ng of RNA, 1.5 mM $MgCl_2$, 0.125 µl AmpliTaq® Gold, 160 µM each dNTP (plus 20 µM additional from the reverse transcriptase reaction), Perkin-Elmer TAQ buffer (from AmpliTaq® Gold kit, Perkin-Elmer, Foster City, Calif.), in a 25 µl reaction volume. Each of oligonucleotide primers 3407 through 3414 was used in combination with each of oligos 3415 through 3422 for a total for 64 reactions. Reactions were run on the Perkin-Elmer 7700 Sequence Detection machine under the following conditions: 10 min at 95° C., 4 cycles of, 45° C. annealing for 15 second, 72° C. extension for 45 second and 95° C. denaturation for 15 seconds followed by 35 cycles under the same conditions with the exception that the annealing temperature was raised to 55° C. (The foregoing conditions are referred to herein as "Reaction 1 conditions.") PCR products were visualized on 4% agarose gel (Northern blots) and a prominent band of the expected size (68 bp) was seen in reactions, particularly with the primers 3515–3518. The 68 kb band was sequenced and the internal region coded for the expected amino acid sequence. This gave the exact DNA sequence for 22 bp of the internal region of this fragment.

Additional sequence was deduced from the efficiency of various primer pools of discrete sequence in generating this PCR product. Primer pools 3419 to 3422 (SEQ ID NOS: 15–18) gave very poor or no product, whereas pools 3415 to 3418 (SEQ ID NOS:11–14 respectively) gave robust signal. The difference between these pools is a CTC (3415 to 3418) (SEQ ID NOS:11–14) vs TTC (3419 to 3422) (SEQ ID NOS:15–18) in the 3' most end of the pools. Since CTC primed more efficiently we can conclude that the reverse complement GAG is the correct codon. Since Met coding is unique it was concluded that the following codon is ATG. Thus the exact DNA sequence obtained is:

```
                                      (SEQ ID NO: 49)
CCC.GGC.CGG.AGG.GGC.AGC.TTT.GTG.GAG.ATG.GT
``` encoding the amino acid sequence P G R R G S F V E M V (SEQ ID NO: 50). This sequence can be used to design exact oligonucleotides for 3 and 5' RACE PCR on either cDNA or libraries or to design specific hybridization probes to be used to screen libraries. Since the degenerate PCR product was found to be so robust, this reaction may also be used as a diagnostic for the presence of clones containing this sequence. Pools of libraries can be screened using this PCR product to indicate the presence of a clone in the pool. The pools can be broken out to identify individual clones. Screening pools of known complexity and or size can provide information on the abundance of this clone in a library or source and can approximate the size of the full length clone or message.

For generation of a probe, PCR reactions using oligonucleotides 3458 (SEQ ID NO:19) and 3469 (SEQ ID NO:21) or 3458 (SEQ ID NO: 19) and 3468 (SEQ ID NO: 20) (Table 4) can be carried out using the 23 RACE product, clone 9C7E.35 (30 ng, clone 9C7E.35 was isolated from origene library, see Example 2), or cDNA generated from brain, using the standard PCR conditions (Perkin-Elmer, rtPCR and AmpliTaq® Gold kits) with the following following: 25 µl reaction volume 1.5 mM MgCl2, 0.125 µl of AmpliTaq® Gold (Perkin-Elmer), initial 95° for 10 min to activate the AmpliTaq® Gold, 36 cycles of 65° 15 sec 72° 45 sec 95° for 15 sec, followed by 3 min at 72°. Product was purified on a Quiagen PCR purification kit and used as a substrate for randompriming to generate a radiolabelled probe (Sambrook, et al., supra; Amersham RediPrime® kit). This probe was used to isolate full length close pCEK clone 27 shown in FIGS. 12 and 13(A–E) (SEQ ID NO:48).

Derivation of Full Length Clone pCEK Clone 27

A human primary neuronal cell library in the mammalian expression vector pCEK2 vector was generated using size selected cDNA, and pools of clones generated from different sized inserts. The cDNA library for β-secretase screening was made with poly(A)+ RNA isolated from primary human neuronal cells. The cloning vector was pCEK2 (FIG. 12).

pCEK2

Double-stranded cDNA inserts were synthesized using the cDNA Synthesis Kit from Stratagene with some modifications. The inserts were then fractionated according to their sizes. A total of five fractions were individually ligated with double-cut (NotI and XhoI) pCEK2 and subsequently transformed into the E. Coli strain XL-10 Gold which is designed to accept very large plasmids.

The fractions of transformed E. coli were plated on Terrific Broth agar plates containing ampicilin and let grown for 18 hours. Each fraction yielded about 200,000 colonies to give a total of one million colonies. The colonies were then scraped from the plates and plasmids isolated from them in pools of approximately 70,000 clones/pool. 70,000 clones from each pool of the library was screened for the presence of the putative β-secretase gene using the diagnostic PCR reaction (degenerate primers 3411 (SEQ ID NO:7) and 3417 (SEQ ID NO:13) shown above).

70,000 clones from each pool of the library was screened for the presence of the putative β-secretase gene using the diagnostic PCR reaction (degenerate primers 3411 and 3417 shown above).

Clones from the 1.5 kb pool were screened using a radiolabeled probe generated from a 390 b.p. PCR product generated from clone 9C7E.35. For generation of a probe, PCR product was generated using 3458(SEQ ID NO:19) and 3468(SEQ ID NO:20) as primers and clone 9C7E.35 (30 ng) as substrate.

PCR product was used as a substrate for random priming to generate a radiolabeled probe. 180,000 clones from the 1.5 kb pool (70,000 original clones in this pool), were screened by hybridization with the PCR probe and 9 positive clones identified. Four of these clones were isolated and by restriction mapping these appear to encode two independent clones of 4 to 5 kb (clone 27) and 6 to 7 kb (clone 53) length. Sequencing of clone 27 verified that it contains a coding region of 1.5 kb. FIGS. 13(A–E) shows the sequence of pCEK clone 27 (clone 27) (SEQ ID NO:48).

TABLE 4

| SEQ ID NO. | Nucleotide Sequence Pool (Degenerate substitutions are shown in No. parentheses) |
|---|---|
| 3 | 3407 G.AGA.GAC.GA(GA).GA(GA).CC(AT).GAG.GAG.CC |
| 4 | 3408 G.AGA.GAC.GA(GA).GA(GA).CC(AT).GAA.GAG.CC |
| 5 | 3409 G.AGA.GAC.GA(GA).GA(GA).CC(AT).GAA.GAA.CC |
| 6 | 3410 G.AGA.GAC.GA(GA).GA(GA).CC(AT).GAG.GAA.CC |
| 7 | 3411 AGA.GAC.GA(GA).GA(GA).CC(CG).GAG.GAG.CC |
| 8 | 3412 AGA.GAC.GA(GA).GA(GA).CC(CG).GAA.GAG.CC |
| 9 | 3413 AGA.GAC.GA(GA).GA(GA).CC(CG).GAA.GAA.CC |
| 10 | 3414 AGA.GAC.GA(GA).GA(GA).CC(CG).GAG.GAA.CC |
| 11 | 3415 CG.TCA.CAG.(GA)TT.(GA)TC.AAC.CAT.CTC |
| 12 | 3416 CG.TCA.CAG.(GA)TT.(GA)TC.TAC.CAT.CTC |
| 13 | 3417 CG.TCA.CAG.(GA)TT.(GA)TC.CAC.CAT.CTC |
| 14 | 3418 CG.TCA.CAG.(GA)TT.(GA)TG.GAC.CAT.CTC |
| 15 | 3419 CG.TCA.CAG.(GA)TT.(GA)TC.AAC.CAT.TTC |
| 16 | 3420 CG.TCA.CAG.(GA)TT.(GA)TC.TAC.CAT.TTC |
| 17 | 3421 CG.TCA.CAG.(GA)TT.(GA)TC.CAC.CAT.TTC |
| 18 | 3422 CG.TCA.CAG.(GA)TT.(GA)TC.GAC.CAT.TTC |
| 19 | 3458 GAG GGG CAG CTT TGT GGA GA |
| 20 | 3468 CAG.CAT.AGG.CCA.GCC.CCA.GGA.TGC.CT |
| 21 | 3469 GTG.ATG.GCA.GCA.ATG.TTG.GCA.CGC |

EXAMPLE 2

Screening of Human Fetal Brain cDNA Library

The Origene human fetal brain Rapid-Screen™ cDNA Library Panel is provided as a 96-well format array consisting of 5000 clones (plasmid DNA) per well from a human fetal brain library. Subplates are available for each well consisting of 96 wells of 50 clones each in *E. coli*. This is an oligo-dT primed library, size-selected and unidirectionally inserted into the vector pCMV-XL3.

94 wells from the master plate were screened using PCR. The Reaction 1 Conditions described in Example 1, above, were followed, using only primers 3407 (SEQ ID NO:3) and 3416 (SEQ ID NO:12) with 30 ng of plasmid DNA from each well. Two pools showed the positive 70 bp band. The same primers and conditions were used to screen 1 μl *E. coli* from each well of one of the subplates. *E. coli* from the single positive well was then plated onto LB/amp plates and single colonies screened using the same PCR conditions. The positive clone, about 1 Kb in size, was labeled 9C7E.35.

It contained the original peptide sequence as well as 5' sequence that included a methionine. The 3' sequence did not contain a stop codon, suggesting that this was not a full-length clone, consistent with Northern blot data.

EXAMPLE 3

PCR Cloning Methods

3'RACE was used in experiments carried out in support of the present invention to elucidate the polynucleotide encoding human β-secretase. Methods and conditions appropriate for replicating the experiments described herein and/or determining polynucleotide sequences encoding additional members of the novel family of aspartyl proteases described herein may be found, for example, in White, B. A., ed., PCR Cloning Protocols; Humana Press, Totowa, N.J., 1997, or Ausubel, supra, both of which are incorporated herein by reference.

RT-PCR

For reverse transcription polymerase chain reaction (RT-PCR), two partially degenerate primer sets used for RT-PCR amplification of a cDNA fragment encoding this peptide. Primer set 1 consisted of DNA's #3427–3434 (SEQ ID NOS:22–29 respectively), the sequences of which are shown in Table 5, below. Matrix RT-PCR using combinations of primers from this set with cDNA reverse transcribed from primary human neuronal cultures as template yielded the predicted 54 bp cDNA product with primers #3428+3433 (SEQ ID NOS:23–28 respectively). All RT-PCR reactions employed 10–50 ng input poly-A+ RNA equivalents per reaction, and were carried out for 35 cycles employing step cycle conditions with a 95° C. denaturation for 1 minute, 50° C. annealing for 30 sec, and a 72° C. extension for 30 sec.

The degeneracy of primers #3428+3433 (SEQ ID NOS: 23–28) was further broken down, resulting in primer set 2, comprising DNAs #3448–3455 (SEQ ID NOS:30–37) (Table 5). Matrix RT-PCR was repeated using primer set 2, and cDNA reverse transcribed from poly-A+ RNA from IMR-32 human neuroblastoma cells (American Type Culture Collection, Manassas, Va.), as well as primary human neuronal cultures, as template for amplification. Primers #3450 (SEQ ID NO:32) and 3454 (SEQ ID NO:36) from set 2 most efficiently amplified a cDNA fragment of the predicted size (72 bp), although primers 3450+3453 (SEQ ID NOS:32 and 35), and 3450+3455 (SEQ ID NOS:32 and 37) also amplified the same product, albeit at lower efficiency. A 72 bp PCR product was obtained by amplification of cDNA from IMR-32 cells and primary human neuronal cultures with primers 3450 (SEQ ID NO:32) and 3454 (SEQ ID NO:36).

5' and 3' RACE-PCR

Internal primers matching the upper (coding) strand for 3' Rapid Amplification of 5' Ends (RACE) PCR, and lower (non-coding) strand for 5' RACE PCR were designed and made according to methods known in the art (e.g., Frohman, M. A., M. K. Dush and G. R. Martin (1988). "Rapid production of full-length cDNAs from rare transcripts: amplification using a single gene specific oligo-nucleotide primer." *Proc. Natl. Acad. Sci. U.S.A.* 85(23): 8998–9002.) The DNA primers used for this experiment (#3459 & #3460) (SEQ ID NOS:38 and 39) are illustrated schematically in FIG. 4, and the exact sequence of these primers is presented in Table 3. These primers can be utilized in standard RACE-PCR methodology employing commercially available templates (e.g. Marathon Ready cDNA®, Clontech Labs), or custom tailored cDNA templates prepared from RNAs of interest as described by Frohman et al. (ibid.).

In experiments carried out in support of the present invention, a variation of RACE was employed to exploit an IMR-32 cDNA library cloned in the retrovirus expression vector pLPCXlox, a derivative of pLNCX. As the vector junctions provide unique anchor sequences abutting the cDNA inserts in this library, they serve the purpose of 5' and 3' anchor primers in RACE methodology. The sequences of the specific 5' and 3' anchor primers we employed to amplify β-secretase cDNA clones from the library, primers #3475 (SEQ ID NO:40) and #3476 (SEQ ID NO:41), are derived from the DNA sequence of the vector provided by Clontech Labs, Inc., and are shown in Table 3.

Primers #3459 (SEQ ID NO:38) and #3476 (SEQ ID NO:41) were used for 3' RACE amplification of downstream sequences from our IMR-32 cDNA library in the vector pLPCXlox. The library had previously been sub-divided into 100 pools of 5,000 clones per pool, and plasmid DNA was isolated from each pool. A survey of the 100 pools with the primers identified as diagnostic for presence of the β-secretase clone, according to methods described in Example 1, above, provided individual pools from the library for RACE-PCR. 100 ng template plasmid from pool 23 was used for PCR amplification with primers 3459+3476 (SEQ ID NOS:38 and 41 respectively). Amplification was carried out for 40 cycles using ampli-Taq Gold®, under the following conditions: denaturation at 95° C. for 1 min, annealing at 65° C. for 45 sec., and extension at 72° C. for 2 min. Reaction products were fractionated by agarose gel chromatography, according to methods known in the art (Ausubel; Sambrook).

An approximately 1.8 Kb PCR fragment was revealed by agarose gel fractionation of the reaction products. The PCR product was purified from the gel and subjected to DNA sequence analysis using primer #3459 (SEQ ID NO:38). The resulting sequence, designated 23A, and the predicted amino acid sequence deduced from the DNA sequence are shown in FIG. 5. Six of the first seven deduced amino-acids from one of the reading frames of 23A were an exact match with the last 7 amino-acids of the N-terminal sequence determined from the purified protein, purified and sequenced in further experiments carried out in support of the present invention, from natural sources.

TABLE 5

| SEQ ID NO. | DNA # | NUCLEOTIDE SEQUENCE | COMMENTS |
|---|---|---|---|
| 22 | 3427 | GAY GAR GAG CCN GAG GA | |
| 23 | 3428 | GAY GAR GAG CCN GAa GA | |
| 24 | 3429 | GAY GAR GAa CCN GAg GA | |
| 25 | 3430 | GAY GAR GAa CCN GAa GA | |
| 26 | 3431 | RTT RTC NAC CAT TTC | |
| 27 | 3432 | RTT RTC NAC CAT cTC | |
| 28 | 3433 | TCN ACC ATY TCN ACA AA | |
| 29 | 3434 | TCN ACC ATY TCN ACG AA | |
| 30 | 3448 | ata ttc tag a GAY GAR GAg CCa GAa GA | 5' primer, break down of 3428 w/5' XbaI tail, 1 of 4 |
| 31 | 3449 | ata ttc tag a GAY GAR GAg CCg GAa GA | 5' primer, break down of 3428 w/5' XbaI tail, 2 of 4 |
| 32 | 3450 | ata ttc tag a GAY GAR GAg CCc GAa GA | 5' primer, break down of 3428 w/5' XbaI tail, 3 of 4 |
| 33 | 3451 | ata ttc tag a GAY GAR GAg CCt GAa GA | 5' primer, break down of 3428 w/5' XbaI tail, 4 of 4 |
| 34 | 3452 | aca cga att c TT RTC NAC CAT YTC aAC AAA | breakdown of 3433, 1 of 4; tm = 50 |
| 35 | 3453 | aca cga att c TT RTC NAC CAT YTC gAC AAA | breakdown of 3433 w/5' Eco RI tail, 2 of 4; tm = 50 |
| 36 | 3454 | aca cga att c TT RTC NAC CAT YTC cAC AAA | breakdown of 3433 w/5' Eco RI tail, 3 of 4; tm = 50 |
| 37 | 3455 | aca cga att c TT RTC NAC CAT YTC tAC AAA | breakdown of 3433 w/5' Eco RI tail, 4 of 4; tm = 50 |
| 38 | 3459 | aa gaG CCC GGC CGG AGG GGC A | 5' upper strand primer for 3' race encodes eEPGRRG |
| 39 | 3460 | aaa GCT GCC CCT CCG GCC GGG | 3' lower strand primer for 5' RACE |
| 40 | 3475 | AGC TCG TTT AGT GAA CCG TCA GAT CG | pLNCX 5' primer |
| 41 | 3476 | ACC TAC AGG TGG GGT CTT TCA TTC CC | pLNCX, 3' primer |

EXAMPLE 4

β-secretase Inhibitor Assays

Assays for measuring β-secretase activity are well known in the art. Particularly useful assays, summarized below, are detailed in allowed U.S. Pat. No. 5,744,346, incorporated herein by reference.

A. Preparation of MBP-C125sw
 1. Preparation of cells
 Two 250 ml cell culture flasks containing 50 ml LBamp100 per flask were seeded with one colony per flask of *E. coli* pMAL-C125SW cl. 2 (*E. coli* expressing MBP-C125sw fusion protein). Cells were allowed to grow overnight at 37° C. Aliqouts (25 ml) were seeded in 500 ml per flask of LBamp100 in 2 liter flasks, which were then allowed to grow at 30°. Optical densities were measured at 600 nm (OD600) vs LB broth; 1.5 ml 100 mM IPTG was added when the OD was ~0.5. At this point, a pre-incubation aliqout was removed for SDS-PAGE ("−I"). Of this aliqout, 0.5 ml was centrifuged for 1 min in a Beckman microfuge, and the resulting pellet was dissolved in 0.5 ml 1×LSB. The cells were incubated/induced for 5–6 hours at 30 C, after which a post-incubation aliquot ("+I") was removed. Cells were then centrifuged at 9,000 rpm in a KA9.1 rotor for 10 min at 4° C. Pellets were retained and stored at −20 C.

2. Extraction of bacterial cell pellets

Frozen cell pellets were resuspended in 50 ml 0.2 M NaCl, 50 mM Tris, pH 7.5, then sonicated in rosette vessal for 5×20 sec bursts, with 1 min rests between bursts. The extract was centrifuged at 16,500 rpm in a KA18.5 rotor 30 min (39,000×g). Using pipette as a pestle, the sonicated pellet was suspended in 50 ml urea extraction buffer (7.6 M urea, 50 mM Tris pH 7.5, 1 mM EDTA, 0.5% TX-100). The total volume was about 25 ml per flask. The suspension was then sonicated 6×20 sec, with 1 min rests between bursts. The suspension was then centrifuged again at 16,500 rpm 30 min in the KA18.5 rotor. The resulting supernatant was added to 1.5 L of buffer consisting of 0.2 M NaCl 50 mM Tris buffer, pH 7.5, with 1% Triton X-100 (0.2M NaCl-Tris-1% Tx), and was stirred gently at 4 degrees C. for 1 hour, followed by centrifugation at 9,000 rpm in KA9.1 for 30 min at 4° C. The supernatant was loaded onto a column of washed amylose (100 ml of 50% slurry; New England BioLabs). The column was washed with 0.2 M NaCl-Tris-1% TX to baseline (+10 column volumes), then with 2 column volumes 0.2M NaCl-Tris-1% reduced Triton X-100. The protein was then eluted with 10 mM maltose in the same buffer. An equal volume of 6 M guanidine HCl/0.5% TX-100 was added to each fraction. Peak fractions were pooled and diluted to a final concentration of about 2 mg/ml. The fractions were stored at −40 degrees C., before dilution (20-fold, to 0.1 mg/ml in 0.15% Triton X-100). Diluted aliquots were also stored at −40 C.

B. Antibody-based Assays

The assays described in this section are based on the ability of certain antibodies, hereinafter "cleavage-site antibodies," to distinguish cleavage of APP by β-secretase, based on the unique cleavage site and consequent exposure of a specific C-terminus formed by the cleavage. The recognized sequence is a sequence of usually about 3–5 residues is immediately amino terminal of the β amyloid peptide (βAP) produced by β-secretase cleavage of β-APP, such as Val-Lys-Met in wild-type or Val-Asn-Leu- in the Swedish double mutation variant form of APP. Recombinantly-expressed proteins, described below, were used as substrates for β-secretase.

MBP-C125 Assay:

MBP-C125 substrates were expressed in *E. coli* as a fusion protein of the last 125 amino acids of APP fused to the carboxy-terminal end of maltose-binding protein (MBP), using commercially available vectors from New England Biolabs. The β-cleavage site was thus 26 amino acids downstream of the start of the C-125 region. This latter site is recognized by monoclonal antibody SW192.

Figures 19A, 19B:
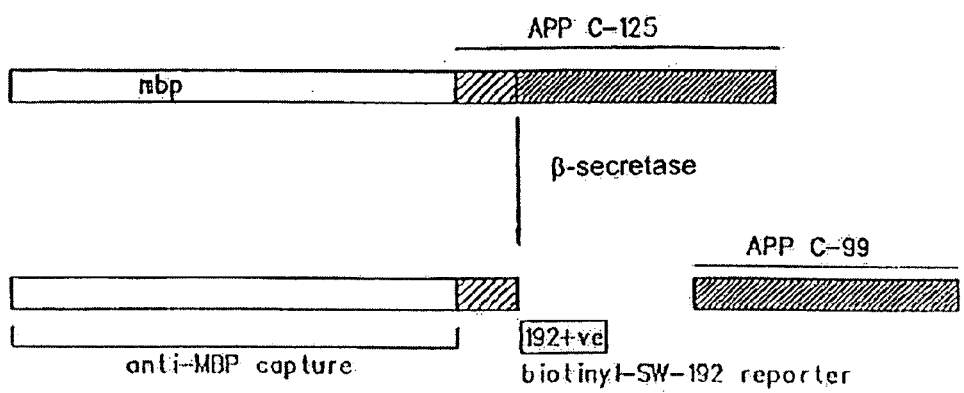
FIG. 19A shows a schematic of an APP substrate fragment, and its use in conjunction with antibodies SW192 and 8E-192 in the assay.
FIG. 19B shows the β-secretase cleavage sites in the wild-type APP sequence (SEQ ID NO: 103) and Swedish APP sequence (SEQ ID NO: 104).
Figure 20:
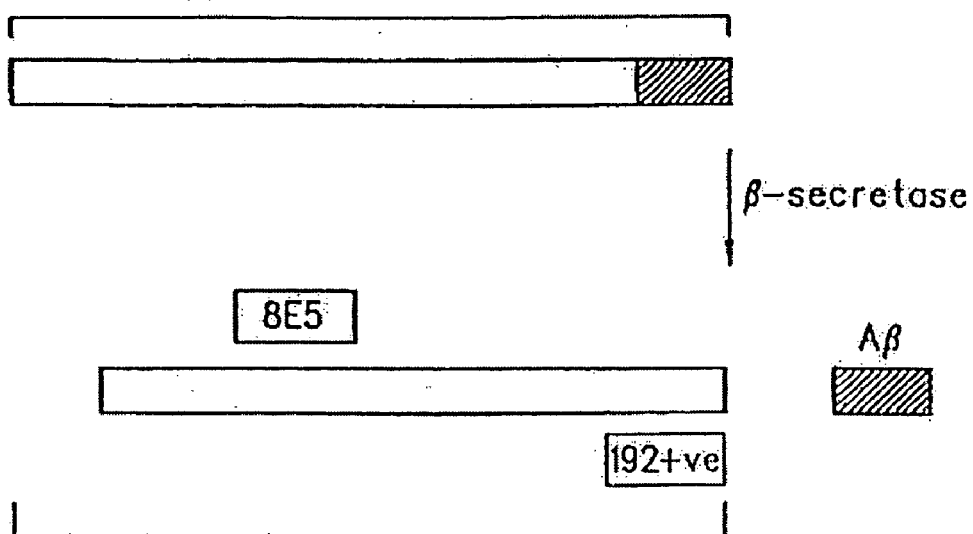
FIG. 20 shows a schematic of a second APP substrate fragment derived from APP 638, and it use in conjunction with antibodies SW 192 and 8E-192 in the assay.

Recombinant proteins were generated with both the wild-type APP sequence (MBP-C125 wt) at the cleavage site ( . . . Val-Lys-Met-Asp-Ala . . . ) (SEQ ID NO:54) or the "Swedish" double mutation (MBP-C125 sw) ( . . . Val-Asn-Leu-Asp-Ala . . . ) (SEQ ID NO:51). As shown schematically in FIG. 19A, cleavage of the intact MBP-fusion protein results in the generation of a truncated amino-terminal fragment, with the new SW-192 Ab-positive epitope uncovered at the carboxy terminus. This amino-terminal fragment can be recognized on Western blots with the same Ab, or, quantitatively, using an anti-MBP capture-biotinylated SW-192 reporter sandwich format, as shown in FIG. 19A. Anti-MBP polyclonal antibodies were raised in rabbits (Josman Labs, Berkeley) by immunization with purified recombinantly expressed MBP (New England Biolabs). Antisera were affinity purified on a column of immobilized MBP. MBP-C125 SW and WT substrates were expressed in *E. coli*, then purified as described above.

Microtiter 96-well plates were coated with purified anti-MBP antibody (at a concentration of 5–10 μg/ml), followed by blocking with 2.5 g/liter human serum albumin in 1 g/liter sodium phosphate monobasic, 10.8 g/liter sodium phosphate dibasic, 25 g/liter sucrose, 0.5 g/liter sodium azide, pH 7.4. Appropriately diluted β-secretase enzyme (5 μl) was mixed with 2.5 μl of 2.2 μM MBP-C125sw substrate stock, in a 50 μl reaction mixture with a final buffer concentration of 20 mM acetate buffer, pH 4.8, 0.06% Triton X-100, in individual wells of a 96-well microtiter plate, and incubated for 1 hour at 37 degrees C. Samples were then diluted 5-fold with Specimen Diluent (0.2 g/l sodium phosphate monobasic, 2.15 g/l sodium phosphate dibasic, 0.5 g/l sodium azide, 8.5 g/l sodium chloride, 0.05% Triton X-405, 6 g/l BSA), further diluted 5–10 fold into Specimen Diluent on anti-MBP coated plates, and incubated for 2 hours at room temperature. Following incubations with samples or antibodies, plates were washed at least four times in TTBS (0.15 M NaCl, 50 mM Tris, ph&.5, 0.05% Tween-20). Biotinylated SW192 antibodies were used as the reporter. SW192 polyclonal antibodies were biotinylated using NHS-biotin (Pierce), following the manufacturer's instruction. Usually, the biotinylated antibodies were used at about 240 ng/ml, the exact concentration varying with the lot of antibodies used. Following incubation of the plates with the reporter, the ELISA was developed using streptavidin-labeled alkaline phosphatase (Boeringer-Mannheim) and 4-methyl-umbelliferyl phosphate as fluorescent substrate. Plates were read in a Cytofluor 2350 Fluorescent Measurement System. Recombinantly generated MBP-26SW (product analog) was used as a standard to generate a standard curve, which allowed the conversion of fluorescent units into amount of product generated.

This assay protocol was used to screen for inhibitor structures, using "libraries" of compounds assembled onto 96-well microtiter plates. Compounds were added, in a final concentration of 20 μg/ml in 2% DMSO, in the assay format described above, and the extent of product generated compared with control (2% DMSO only) β-secretase incubations, to calculate "% inhibition." "Hits" were defined as compounds which result in >35% inhibition of enzyme activity at test concentration. This assay can also be used to provide $IC_{50}$ values for inhibitors, by varying the concentration of test compound over a range to calculate from a dose-response curve the concentration required to inhibit the activity of the enzyme by 50%.

Generally, inhibition is considered significant as compared to control activity in this assay if it results in activity that is at least 1 standard deviation, and preferably 2 standard deviations lower than a mean activity value determined over a range of samples. In addition, a reduction of activity that is greater than about 25%, and preferably greater than about 35% of control activity may also be considered significant.

Using the foregoing assay system, 24 "hits" were identified (>30% inhibition at 50 μM concentration) from the first 6336 compounds tested (0.4% hit rate). Of these 12 compounds had $IC_{50}$s less than 50 μM, including re-P26-P4'sw assay, below.

P26-P4'sw assay The P26-P4'sw substrate is a biotin-linked peptide of the sequence (biotin)CGGADRGLTTR-PGSGLTNIKTEEISEVNLDAEF (SEQ ID NO:63). The P26-P1 standard has the sequence (biotin)CGGADRGLT-TRPGSGLTNIKTEEISEVNL (SEQ ID NO:64), where the N-terminal "CGG" serves as a linker between biotin and the substrate in both cases. Peptides were prepared by Anaspec, Inc. (San Jose, Calif.) using solid phase synthesis with boc-amino acids. Biotin was coupled to the terminal cysteine sulfhydryl by Anaspec, Inc. after synthesis of the peptide, using EZ-link Iodoacetyl-LC-Biotin (Pierce). Peptides are stored as 0.8–1.0 mM stocks in 5 mM Tris, with the pH adjusted to around neutral (pH 6.5–7.5) with sodium hydroxide.

For the enzyme assay, the substrate concentration can vary from 0–200 μM. Specifically for testing compounds for inhibitory activity, substrate concentration is 1.0 μM. Compounds to be tested were added in DMSO, with a final DMSO concentration of 5%; in such experiments, the controls also receive 5% DMSO. Concentration of enzyme was varied, to give product concentrations within the linear range of the ELISA assay (125–2000 pM, after dilution). These components were incubated in 20 mM sodium acetate, pH 4.5, 0.06% Triton X-100, at 37° C. for 1 to 3 hours. Samples were diluted 5-fold in specimen diluent (145.4 mM sodium chloride, 9.51 mM sodium phosphate, 7.7 mM sodium azide, 0.05% Triton X-405, 6 gm/liter bovine serum albumin, pH 7.4) to quench the reaction, then diluted further for the ELISA as needed. For the ELISA, Costar High Binding 96-well assay plates (Corning, Inc., Corning, N.Y.) were coated with SW 192 monoclonal antibody from clone 16A7, or a clone of similar affinity. Biotin-P26-P4' standards were diluted in specimen diluent to a final concentration of 0 to 2 nM. Diluted samples and standards (100 μl) are incubated on the SW192 plates at 4° C. for 24 hours. The plates are washed 4 times in TTBS buffer (150 mM sodium chloride, 25 mM Tris, 0.05% Tween 20, pH 7.5), then incubated with 0.1 ml/well of streptavidin-alkaline phosphatase (Roche Molecular Biochemicals, Indianapolis, Ind.) diluted 1:3000 in specimen diluent. After incubating for one hour at room temperature, the plate was washed 4 times in TTBS, as described in the previous section, and incubated with fluorescent substrate solution A (31.2 gm/liter 2-amino-2-methyl-1-propanol, 30 mg/liter, adjusted to pH 9.5 with HCl). Fluorescent values were read after 30 minutes.

C. Assays Using Synthetic Oligopeptide Substrates

This assay format is particularly useful for measuring activity of partially purified β-secretase preparations. Synthetic oligopeptides are prepared which incorporate the known cleavage site of β-secretase, and optional detectable tags, such as fluorescent or chromogenic moieties. Examples of such peptides, as well as their production and detection methods are described in allowed U.S. Pat. No. 5,942,400, herein incorporated by reference. Cleavage products can be detected using high performance liquid chromatography, or fluorescent or chromogenic detection methods appropriate to the peptide to be detected, according to methods well known in the art. By way of example, one such peptide has the sequence SEVNL DAEF (SEQ ID NO: 52), and the cleavage site is between residues 5 and 6. Another preferred substrate has the sequence ADRGLTTRPGSGLTNIK-TEEISEVNLDAE F (SEQ ID NO: 53), and the cleavage site is between residues 26 and 27.

D. β-secretase Assays of Crude Cell or Tissue Extracts

Cells or tissues were extracted in extraction buffer (20 mM HEPES, pH 7.5, 2 mM EDTA, 0.2% Triton X-100, 1 mM PMSF, 20 μg/ml pepstatin, 10 μg/ml E-64). The volume of extraction buffer will vary between samples, but should be at least 200 μl per $10^6$ cells. Cells can be suspended by trituration with a micropipette, while tissue may require homogenization. The suspended samples were incubated for 30 minutes on ice. If necessary to allow pipetting, unsolubilized material was removed by centrifugation at 4 degrees C., 16,000×g (14,000 rpm in a Beckman microfuge) for 30 minutes. The supernate was assayed by dilution into the final assay solution. The dilution of extract will vary, but should be sufficient so that the protein concentration in the assay is not greater than 60 μg/ml. The assay reaction also contained 20 mM sodium acetate, pH 4.8, and 0.06% Triton X-100 (including Triton contributed by the extract and substrate), and 220–110 nM MBP-C125 (a 1:10 or 1:20 dilution of the 0.1 mg/ml stock described in the protocol for substrate preparation). Reactions were incubated for 1–3 hours at 37 degrees C. before quenching with at least 5-fold dilution in specimen diluent and assaying using the standard protocol.

EXAMPLE 5

Purification of β-secretase

A. Purification of Naturally Occurring β-secretase

Human 293 cells were obtained and processed as described in U.S. Pat. No. 5,744,346, incorporated herein by reference. (293 cells are available from the American Type Culture Collection, Manassas, Va.). Frozen tissue (293 cell paste or human brain) was cut into pieces and combined with five volumes of homogenization buffer (20 mM Hepes, pH 7.5, 0.25 M sucrose, 2 mM EDTA). The suspension was homogenized using a blender and centrifuged at 16,000×g for 30 min at 4° C. The supernatants were discarded and the pellets were suspended in extraction buffer (20 mM MES, pH 6.0, 0.5% Triton X-100, 150 mM NaCl, 2 mM EDTA, 5 μg/ml leupeptin, 5 μg/ml E64, 1 μg/ml pepstatin, 0.2 mM PMSF) at the original volume. After vortex-mixing, the extraction was completed by agitating the tubes at 4° C. for a period of one hour. The mixtures were centrifuged as above at 16,000×g, and the supernatants were pooled. The pH of the extract was adjusted to 7.5 by adding ~1% (v/v) of 1 M Tris base (not neutralized).

The neutralized extract was loaded onto a wheat germ agglutinin-agarose (WGA-agarose) column pre-equilibrated with 10 column volumes of 20 mM Tris, pH 7.5, 0.5% Triton X-100, 150 mM NaCl, 2 mM EDTA, at 4° C. One milliliter of the agarose resin was used for every 1 g of original tissue used. The WGA-column was washed with 1 column volume of the equilibration buffer, then 10 volumes of 20 mM Tris, pH 7.5, 100 mM NaCl, 2 mM NaCl, 2 mM EDTA, 0.2% Triton X-100 and then eluted as follows. Three-quarter column volumes of 10% chitin hydrolysate in 20 mM Tris, pH 7.5, 0.5%, 150 mM NaCl, 0.5% Triton X-100, 2 mM EDTA were passed through the column after which the flow was stopped for fifteen minutes. An additional five column volumes of 10% chitin hydrolysate solution were then used to elute the column. All of the above eluates were combined (pooled WGA-eluate).

The pooled WGA-eluate was diluted 1:4 with 20 mM NaOAc, pH 5.0, 0.5% Triton X-100, 2 mM EDTA. The pH of the diluted solution was adjusted to 5.0 by adding a few drops of glacial acetic acid while monitoring the pH. This "SP load" was passed through a 5-ml Pharmacia HiTrap SP-column equilibrated with 20 mM NaOAc, pH 5.0, 0.5% Triton X-100, 2 mM EDTA, at 4 ml/min at 4° C.

The foregoing methods provided peak activity having a specific activity of greater than 253 nM product/ml/h/μg protein in the MBP-C125-SW assay, where specific activity is determined as described below, with about 1500-fold purification of the protein. Specific activity of the purified β-secretase was measured as follows. MBP C125-SW substrate was combined at approximately 220 nM in 20 mM sodium acetate, pH 4.8, with 0.06% Triton X-100. The amount of product generated was measured by the β-secretase assay, also described below. Specific activity was then calculated as:

$$\text{Specific Activity} = \frac{(\text{Product conc. nM})(\text{Dilution factor})}{(\text{Enzyme sol. vol})(\text{Incub. time h})}$$
$$(\text{Enzyme conc. mg/vol})$$

The Specific Activity is thus expressed as pmoles of product produced per μg of β-secretase per hour. Further purification of human brain enzyme was achieved by loading the SP flow through fraction on to the P10-P4'sta D->V affinity column, according to the general methods described below. Results of this purification step are summarized in Table 1, above.

B. Purification of β-secretase from Recombinant Cells

Recombinant cells produced by the methods described herein generally were made to over-express the enzyme; that is, they produced dramatically more enzyme per cell than is found to be endogenously produced by the cells or by most tissues. It was found that some of the steps described above could be omitted from the preparation of purified enzyme under these circumstances, with the result that even higher levels of purification were achieved.

CosA2 or 293 T cells transfected with β-secretase gene construct (see Example 6) were pelleted, frozen and stored at −80 degrees until use. The cell pellet was resuspended by homogenizing for 30 seconds using a handheld homogenizer (0.5 ml/pellet of approximately $10^6$ cells in extraction buffer consisting of 20 mM TRIS buffer, pH 7.5, 2 mM EDTA, 0.2% Triton X-100, plus protease inhibitors: 5 μg/ml E-64, 10 μg/ml pepstatin, 1 mM PMSF), centrifuged as maximum speed in a microfuge (40 minutes at 4 degrees C.). Pellets were suspended in original volume of extraction buffer, then stirred at 1 hour at 4 degrees C. with rotation, and centrifuted again in a microfuge at maximum speed for 40 minutes. The resulting supernatant was saved as the "extract." The extract was then diluted with 20 mM sodium acetate, pH 5.0, 2 mM EDTA and 0.2% Triton X-100 (SP buffer A), and 5M NaCl was added to a final concentration of 60 mM NaCl. The pH of the solution was then adjusted to pH 5.0 with glacial acetic acid diluted 1:10 in water. Aliquots were saved ("SP load"). The SP load was passed through a 1 ml SP HiTrap column which was pre-washed with 5 ml SP buffer A, 5 ml SP buffer B (SP buffer A with 1 M NaCl) and 10 ml SP buffer A. An additional 2 ml of 5% SP buffer B was passed through the column to dissplace any remaining sample from the column. The pH of the SP flow-through was adjusted to pH 4.5 with 10x diluted acetic acid. This flow-through was then applied to a P10-P4'staD->V-Sepharose Affinity column, as described below. The column (250 μl bed size) was pre-equilibrated with at least 20 column volumes of equilibration buffer (25 mM NaCl, 0.2% Triton X-100, 0.1 mM EDTA, 25 mM sodium acetate, pH 4.5), then loaded with the diluted supernatant. After loading, subsequent steps were carried out at room temperature. The column was washed with washing buffer (125 mM NaCl, 0.2% Triton X-100, 25 mM sodium acetate, pH 4.5) before addition of 0.6 column bed volumes of borate elution buffer (200 mM NaCl, 0.2% reduced Triton X-100, 40 mM sodium borate, pH 9.5). The column was then capped, and an additional 0.2 ml elution buffer was added. The column was allowed to stand for 30 minutes. Two bed volumes elution buffer were added, and column fractions (250 μl) were collected. The protein peak eluted in two fractions. 0.5 ml of 10 mg/ml peptstatin was added per milliliter of collected fractions.

Cell extracts made from cells transfected with full length clone 27 (encoding SEQ ID NO: 2; 1–501), 419stop (SEQ ID NO:57) and 452stop (SEQ ID NO: 59) were detected by Western blot analysis using antibody 264A (polyclonal antibody directed to amino acids 46–67 of β-secretase with reference to SEQ ID NO: 2).

EXAMPLE 6

Preparation of Heterologous Cells Expressing Recombinant β-secretase

Two separate clones (pCEKclone 27 and pCEKclone 53) were transfected into 293T or COS(A2) cells using Fugene and Effectene methods known in the art. 293T cells were obtained from Edge Biosystems (Gaithersburg, Md.). They are KEK293 cells transfected with SV40 large antigen. COSA2 are a subclone of COS1 cells; subcloned in soft agar.

FuGENE Method: 293T cells were seeded at $2\times10^5$ cells per well of a 6 well culture plate. Following overnight growth, cells were at approximately 40–50% confluency. Media was changed a few hours before transfection (2 ml/well). For each sample, 3 μl of FuGENE 6 Transfection Reagent (Roche Molecular Biochemicals, Indianapolis, Ind.) was diluted into 0.1 ml of serum-free culture medium (DME with 10 mM Hepes) and incubated at room temperature for 5 min. One microgram of DNA for each sample (0.5–2 mg/ml) was added to a separate tube. The diluted FuGENE reagent was added drop-wise to the concentrated DNA. After gentle tapping to mix, this mixture was incubated at room temperature for 15 minutes. The mixture was added dropwise onto the cells and swirled gently to mix. The cells were then incubated at 37 degrees C., in an atmosphere of 7.5% $CO_2$. The conditioned media and cells were harvested after 48 hours. Conditioned media was collected, centrifuged and isolated from the pellet. Protease inhibitors (5 μg/ml E64, 2 μg/ml peptstatin, 0.2 mM PMSF) were added prior to freezing. The cell monolayer was rinsed once with PBS, tehn 0.5 ml of lysis buffer (1 mM HIPIS, pH 7.5, 1 mM EDTA, 0.5% Triton X-100, 1 mM PMSF, 10 µg/ml E64) was added. The lysate was frozen and thawed, vortex mixed, then centrifuged, and the supernatant was frozen until assayed.

Effective Method: DNA (0.6 µg) was added with "EFFECTENE" reagent (Qiagen, Valencia, Calif.) into a 6-well culture plate using a standard transfection protocol according to manufacturer's instructions. Cells were harvested 3 days after transfection and the cell pellets were snap frozen. Whole cell lysates were prepared and various amounts of lysate were tested for β-secretase activity using the MBP-C125sw substrate. FIG. 14B shows the results of these experiments, in which picomoles of product formed is plotted against micrograms of COS cell lysate added to the reaction. The legend to the figure describes the enzyme source, where activity from cells transfected with DNA from pCEKclone27 and PCEKclone53 (clones 27 and 53) using Effective are shown as closed diamonds and solid squares, respectively, activity from cells transfected with DNA from clone 27 prepared with FuGENE are shown as open triangles, and mock transfected and control plots show no activity (closed triangles and "X" markers). Values greater than 700 pM product are out of the linear range of the assay.

EXAMPLE 7

Preparation of P10-P4'sta(D->V) Sepharose Affinity Matrix

A. Preparation of P10-P4'sta(D->V) Inhibitor Peptide

P10-P4'sta(D→V) has the sequence $NH_2$-KTEEISEVN[sta]VAEF-COOH (SEQ ID NO: 72), where "sta" represents a statine moiety. The synthetic peptide was synthesized in a peptide synthesizer using boc-protected amino acids for chain assembly. All chemicals, reagents, and boc amino acids were purchased from Applied Biosystems (ABI; Foster City, Calif.) with the exception of dichloromethane and N,N-dimethylformamide which were from Burdick and Jackson. The starting resin, boc-Phe-OCH2-Pam resin was also purchased from ABI. All amino acids were coupled following preactivation to the corresponding HOBT ester using 1.0 equivalent of 1-hydroxybenzotriazole (HOBT), and 1.0 equivalent of N,N-dicyclohexylcarbodiimide (DCC) in dimethylformamide. The boc protecting group on the amino acid α-amine was removed with 50% trifluoroacetic acid in dichloromethane after each coupling step and prior to Hydrogen Fluoride cleavage.

Amino acid side chain protection was as follows: Glu (Bzl), Lys(Cl-CBZ), Ser(OBzl), Thr(OBzl). All other amino acids were used with no further side chain protection including boc-Statine.

[(Bzl) benzyl, (CBZ) carbobenzoxy, (Cl—CBZ) chlorocarbobenzoxy, (OBzl) O-benzyl]

The side chain protected peptide resin was deprotected and cleaved from the resin by reacting with anhydrous hydrogen fluoride (HF) at 0° C. for one hour. This generates the fully deprotected crude peptide as a C-terminal carboxylic acid.

Following HF treatment, the peptide was extracted from the resin in acetic acid and lyophilized. The crude peptide was then purified using preparative reverse phase HPLC on a Vydac C4, 330 Å, 10 µm column 2.2 cm I.D.×25 cm in length. The solvent system used with this column was 0.1% TFA/H2O ([A] buffer) and 0.1% TFA/CH3CN ([B] buffer) as the mobile phase. Typically the peptide was loaded onto the column in 2% [B] at 8–10 mL/min. and eluted using a linear gradient of 2% [B] to 60% [B] in 174 minutes.

The purified peptide was subjected to mass spectrometry, and analytical reverse phase HPLC to confirm its composition and purity.

B. Incorporation into Affinity Matrix

All manipulations were carried out at room temperature. 12.5 ml of 80% slurry of NHS-Sepharose (i.e. 10 ml packed volume; Pharmacia, Piscataway, N.J.) was poured into a Bio-Rad EconoColumn (BioRad, Richmond, Calif.) and washed with 165 ml of ice-cold 1.0 mM HCl. When the bed was fully drained, the bottom of the column was closed off, and 5.0 ml of 7.0 mg/ml P10-P4'sta(D->V) peptide (SEQ ID NO:72) (dissolved in 0.1 M HEPES, pH 8.0) was added. The column was capped and incubated with rotation for 24 hours. After incubation, the column was allowed to drain, then washed with 8 ml of 1.0 M ethanolamine, pH 8.2. An additional 10 ml of the ethanolamine solution was added, and the column was again capped and incubated overnight with rotation. The column bed was washed with 20 ml of 1.5 M sodium chloride, 0.5 M Tris, pH 7.5, followed by a series of buffers containing 0.1 mM EDTA, 0.2% Triton X-100, and the following components; 20 mM sodium acetate, pH 4.5 (100 ml); 20 mM sodium acetate, pH 4.5, 1.0 M sodium chloride (100 ml); 20 mM sodium borate, pH 9.5, 1.0 M sodium chloride (200 ml); 20 mM sodium borate, pH 9.5 (100 ml). Finally, the column bed was washed with 15 ml of 2 mM Tris, 0.01% sodium azide (no Triton or EDTA), and stored in that buffer, at 4° C.

EXAMPLE 8

Co-Transfection of Cells with β-secretase and APP 293T cells were co-transfected with equivalent amounts plasmids encoding APPsw or wt and β-secretase or control β-galalactoside (β-gal) cDNA using FuGene 6 Reagent, as described in Example 4, above. Either pCEKclone 27 or pohCJ containing full length β-secretase were used for expression of β-secretase. The plasmid construct pohCK751 used for the expression of APP in these transfections was derived as described in Dugan et al., JBC, 270(18) 10982–10989(1995) and shown schematically in FIG. 21. A β-gal control plasmid was added so that the total amount of plasmid transfected was the same for each condition. β-gal expressing pCEK and pohCK vectors do not replicate in 293T or COS cells. Triplicate wells of cells were transfected with the plasmid, according to standard methods described above, then incubated for 48 hours, before collection of conditioned media and cells. Whole cell lysates were prepared and tested for the β-secretase enzymatic activity. The amount of β-secretase activity expressed by transfected 293T cells was comparable to or higher than that expressed by CosA2 cells used in the single transfection studies. Western blot assays were carried out on conditioned media and cell lysates, using the antibody 13G8, and Aβ ELISAs carried out on the conditioned media to analyze the various APP cleavage products.

While the invention has been described with reference to specific methods and embodiments, it will be appreciated that various modifications and changes may be made without departing from the invention. All patent and literature references referred to herein are herein incorporated by reference.

What is claimed is:

1. An isolated β-secretase protein beginning at residue 46 and extending to position 452 of SEQ ID NO:2 or up to several amino acids beyond but lacking a transmembrane region.

2. The isolated protein of claim 1 having an amino acid sequence consisting of SEQ ID NO:58.

3. The isolated protein of claim 1, further comprising a FLAG-epitope tag (SEQ ID NO:45) at the C-terminus.

4. A method of making a protein having β-secretase activity involved in processing APP into amyloid beta comprising culturing a host cell comprising a nucleic acid encoding the protein under conditions wherein the cell expresses the protein encoded by the nucleic acid, and isolating the protein, wherein the protein is as defined in claim 1.

* * * * *

SEQUENCE LISTING

<160> NUMBER OF SEQ ID NOS: 104

<210> SEQ ID NO 1
<211> LENGTH: 1503
<212> TYPE: DNA
<213> ORGANISM: Homo sapiens

<400> SEQUENCE: 1

| | | | | | | |
|---|---|---|---|---|---|---|
| atggcccaag | ccctgccctg | gctcctgctg | tggatgggcg | cgggagtgct | gcctgcccac | 60 |
| ggcacccagc | acggcatccg | gctgcccctg | cgcagcggcc | tggggggcgc | cccctgggg | 120 |
| ctgcggctgc | cccgggagac | cgacgaagag | cccgaggagc | ccggccggag | gggcagcttt | 180 |
| gtggagatgg | tggacaacct | gaggggcaag | tcggggcagg | gctactacgt | ggagatgacc | 240 |
| gtgggcagcc | ccccgcagac | gctcaacatc | ctggtggata | caggcagcag | taactttgca | 300 |
| gtgggtgctg | cccccaccc | cttcctgcat | cgctactacc | agaggcagct | gtccagcaca | 360 |
| taccgggacc | tccggaaggg | tgtgtatgtg | ccctacaccc | agggcaagtg | ggaaggggag | 420 |
| ctgggcaccg | acctggtaag | catcccccat | ggccccaacg | tcactgtgcg | tgccaacatt | 480 |
| gctgccatca | ctgaatcaga | caagttcttc | atcaacggct | ccaactggga | aggcatcctg | 540 |
| gggctggcct | atgctgagat | tgccaggcct | gacgactccc | tggagccttt | ctttgactct | 600 |
| ctggtaaagc | agacccacgt | tcccaacctc | ttctccctgc | agctttgtgg | tgctggcttc | 660 |
| cccctcaacc | agtctgaagt | gctggcctct | gtcggaggga | gcatgatcat | tggaggtatc | 720 |
| gaccactcgc | tgtacacagg | cagtctctgg | tatacaccca | tccggcggga | gtggtattat | 780 |
| gaggtgatca | ttgtgcgggt | ggagatcaat | ggacaggatc | tgaaaatgga | ctgcaaggag | 840 |
| tacaactatg | acaagagcat | tgtggacagt | ggcaccacca | accttcgttt | gcccaagaaa | 900 |
| gtgtttgaag | ctgcagtcaa | atccatcaag | gcagcctcct | ccacggagaa | gttccctgat | 960 |
| ggtttctggc | taggagagca | gctggtgtgc | tggcaagcag | gcaccacccc | ttggaacatt | 1020 |
| ttcccagtca | tctcactcta | cctaatgggt | gaggttacca | accagtcctt | ccgcatcacc | 1080 |
| atccttccgc | agcaatacct | gcggccagtg | aagatgtgg | ccacgtccca | agacgactgt | 1140 |
| tacaagtttg | ccatctcaca | gtcatccacg | ggcactgtta | tgggagctgt | tatcatggag | 1200 |
| ggcttctacg | ttgtctttga | tcgggcccga | aaacgaattg | gctttgctgt | cagcgcttgc | 1260 |
| catgtgcacg | atgagttcag | gacggcagcg | gtggaaggcc | cttttgtcac | cttggacatg | 1320 |
| gaagactgtg | gctacaacat | tccacagaca | gatgagtcaa | ccctcatgac | catagcctat | 1380 |
| gtcatggctg | ccatctgcgc | cctcttcatg | ctgccactct | gcctcatggt | gtgtcagtgg | 1440 |
| cgctgcctcc | gctgcctgcg | ccagcagcat | gatgactttg | ctgatgacat | ctccctgctg | 1500 |
| aag | | | | | | 1503 |

<210> SEQ ID NO 2
<211> LENGTH: 501
<212> TYPE: PRT
<213> ORGANISM: Homo sapiens

<400> SEQUENCE: 2

Met Ala Gln Ala Leu Pro Trp Leu Leu Leu Trp Met Gly Ala Gly Val
 1               5                  10                  15

Leu Pro Ala His Gly Thr Gln His Gly Ile Arg Leu Pro Leu Arg Ser
            20                  25                  30

Gly Leu Gly Gly Ala Pro Leu Gly Leu Arg Leu Pro Arg Glu Thr Asp

-continued

```
                35                  40                  45
Glu Glu Pro Glu Pro Gly Arg Arg Gly Ser Phe Val Glu Met Val
 50                  55                  60

Asp Asn Leu Arg Gly Lys Ser Gly Gln Gly Tyr Tyr Val Glu Met Thr
 65                  70                  75                  80

Val Gly Ser Pro Pro Gln Thr Leu Asn Ile Leu Val Asp Thr Gly Ser
                 85                  90                  95

Ser Asn Phe Ala Val Gly Ala Ala Pro His Pro Phe Leu His Arg Tyr
                100                 105                 110

Tyr Gln Arg Gln Leu Ser Ser Thr Tyr Arg Asp Leu Arg Lys Gly Val
                115                 120                 125

Tyr Val Pro Tyr Thr Gln Gly Lys Trp Glu Gly Glu Leu Gly Thr Asp
            130                 135                 140

Leu Val Ser Ile Pro His Gly Pro Asn Val Thr Val Arg Ala Asn Ile
145                 150                 155                 160

Ala Ala Ile Thr Glu Ser Asp Lys Phe Phe Ile Asn Gly Ser Asn Trp
                165                 170                 175

Glu Gly Ile Leu Gly Leu Ala Tyr Ala Glu Ile Ala Arg Pro Asp Asp
                180                 185                 190

Ser Leu Glu Pro Phe Phe Asp Ser Leu Val Lys Gln Thr His Val Pro
                195                 200                 205

Asn Leu Phe Ser Leu Gln Leu Cys Gly Ala Gly Phe Pro Leu Asn Gln
            210                 215                 220

Ser Glu Val Leu Ala Ser Val Gly Gly Ser Met Ile Ile Gly Gly Ile
225                 230                 235                 240

Asp His Ser Leu Tyr Thr Gly Ser Leu Trp Tyr Thr Pro Ile Arg Arg
                245                 250                 255

Glu Trp Tyr Tyr Glu Val Ile Ile Val Arg Val Glu Ile Asn Gly Gln
                260                 265                 270

Asp Leu Lys Met Asp Cys Lys Glu Tyr Asn Tyr Asp Lys Ser Ile Val
            275                 280                 285

Asp Ser Gly Thr Thr Asn Leu Arg Leu Pro Lys Lys Val Phe Glu Ala
290                 295                 300

Ala Val Lys Ser Ile Lys Ala Ala Ser Ser Thr Glu Lys Phe Pro Asp
305                 310                 315                 320

Gly Phe Trp Leu Gly Glu Gln Leu Val Cys Trp Gln Ala Gly Thr Thr
                325                 330                 335

Pro Trp Asn Ile Phe Pro Val Ile Ser Leu Tyr Leu Met Gly Glu Val
            340                 345                 350

Thr Asn Gln Ser Phe Arg Ile Thr Ile Leu Pro Gln Gln Tyr Leu Arg
                355                 360                 365

Pro Val Glu Asp Val Ala Thr Ser Gln Asp Asp Cys Tyr Lys Phe Ala
            370                 375                 380

Ile Ser Gln Ser Ser Thr Gly Thr Val Met Gly Ala Val Ile Met Glu
385                 390                 395                 400

Gly Phe Tyr Val Val Phe Asp Arg Ala Arg Lys Arg Ile Gly Phe Ala
                405                 410                 415

Val Ser Ala Cys His Val His Asp Glu Phe Arg Thr Ala Ala Val Glu
                420                 425                 430

Gly Pro Phe Val Thr Leu Asp Met Glu Asp Cys Gly Tyr Asn Ile Pro
            435                 440                 445

Gln Thr Asp Glu Ser Thr Leu Met Thr Ile Ala Tyr Val Met Ala Ala
450                 455                 460
```

```
Ile Cys Ala Leu Phe Met Leu Pro Leu Cys Leu Met Val Cys Gln Trp
465                 470                 475                 480

Arg Cys Leu Arg Cys Leu Arg Gln Gln His Asp Asp Phe Ala Asp Asp
                485                 490                 495

Ile Ser Leu Leu Lys
            500

<210> SEQ ID NO 3
<211> LENGTH: 24
<212> TYPE: DNA
<213> ORGANISM: Homo sapiens

<400> SEQUENCE: 3
gagagacgar garccwgagg agcc                                          24

<210> SEQ ID NO 4
<211> LENGTH: 24
<212> TYPE: DNA
<213> ORGANISM: Artificial Sequence
<220> FEATURE:
<223> OTHER INFORMATION: Degenerate oligonucleotide primer derived from
      SEQ ID NO: 2

<400> SEQUENCE: 4
gagagacgar garccwgaag agcc                                          24

<210> SEQ ID NO 5
<211> LENGTH: 24
<212> TYPE: DNA
<213> ORGANISM: Artificial Sequence
<220> FEATURE:
<223> OTHER INFORMATION: Degenerate oligonucleotide primer derived from
      SEQ ID NO: 2

<400> SEQUENCE: 5
gagagacgar garccwgaag aacc                                          24

<210> SEQ ID NO 6
<211> LENGTH: 24
<212> TYPE: DNA
<213> ORGANISM: Artificial Sequence
<220> FEATURE:
<223> OTHER INFORMATION: Degenerate oligonucleotide primer derived from
      SEQ ID NO: 2

<400> SEQUENCE: 6
gagagacgar garccwgagg aacc                                          24

<210> SEQ ID NO 7
<211> LENGTH: 23
<212> TYPE: DNA
<213> ORGANISM: Artificial Sequence
<220> FEATURE:
<223> OTHER INFORMATION: Degenerate oligonucleotide primer derived from
      SEQ ID NO: 2

<400> SEQUENCE: 7
agagacgarg arccsgagga gcc                                           23

<210> SEQ ID NO 8
<211> LENGTH: 23
<212> TYPE: DNA
<213> ORGANISM: Artificial Sequence
<220> FEATURE:
<223> OTHER INFORMATION: Degenerate oligonucleotide primer derived from
```

SEQ ID NO: 2

<400> SEQUENCE: 8
agagacgarg arccsgaaga gcc                                          23

<210> SEQ ID NO 9
<211> LENGTH: 23
<212> TYPE: DNA
<213> ORGANISM: Artificial Sequence
<220> FEATURE:
<223> OTHER INFORMATION: Degenerate oligonucleotide primer derived from
      SEQ ID NO: 2

<400> SEQUENCE: 9
agagacgarg arccsgaaga acc                                          23

<210> SEQ ID NO 10
<211> LENGTH: 23
<212> TYPE: DNA
<213> ORGANISM: Artificial Sequence
<220> FEATURE:
<223> OTHER INFORMATION: Degenerate oligonucleotide primer derived from
      SEQ ID NO: 2

<400> SEQUENCE: 10
agagacgarg arccsgagga acc                                          23

<210> SEQ ID NO 11
<211> LENGTH: 23
<212> TYPE: DNA
<213> ORGANISM: Artificial Sequence
<220> FEATURE:
<223> OTHER INFORMATION: Degenerate oligonucleotide primer derived from
      SEQ ID NO: 2

<400> SEQUENCE: 11
cgtcacagrt trtcaaccat ctc                                          23

<210> SEQ ID NO 12
<211> LENGTH: 23
<212> TYPE: DNA
<213> ORGANISM: Artificial Sequence
<220> FEATURE:
<223> OTHER INFORMATION: Degenerate oligonucleotide primer derived from
      SEQ ID NO: 2

<400> SEQUENCE: 12
cgtcacagrt trtctaccat ctc                                          23

<210> SEQ ID NO 13
<211> LENGTH: 23
<212> TYPE: DNA
<213> ORGANISM: Artificial Sequence
<220> FEATURE:
<223> OTHER INFORMATION: Degenerate oligonucleotide primer derived from
      SEQ ID NO: 2

<400> SEQUENCE: 13
cgtcacagrt trtccaccat ctc                                          23

<210> SEQ ID NO 14
<211> LENGTH: 23
<212> TYPE: DNA
<213> ORGANISM: Artificial Sequence
<220> FEATURE:
<223> OTHER INFORMATION: Degenerate oligonucleotide primer derived from
      SEQ ID NO: 2

```
<400> SEQUENCE: 14
cgtcacagrt trtcgaccat ctc                                          23

<210> SEQ ID NO 15
<211> LENGTH: 23
<212> TYPE: DNA
<213> ORGANISM: Artificial Sequence
<220> FEATURE:
<223> OTHER INFORMATION: Degenerate oligonucleotide primer derived from
      SEQ ID NO: 2

<400> SEQUENCE: 15
cgtcacagrt trtcaaccat ttc                                          23

<210> SEQ ID NO 16
<211> LENGTH: 23
<212> TYPE: DNA
<213> ORGANISM: Artificial Sequence
<220> FEATURE:
<223> OTHER INFORMATION: Degenerate oligonucleotide primer derived from
      SEQ ID NO: 2

<400> SEQUENCE: 16
cgtcacagrt trtctaccat ttc                                          23

<210> SEQ ID NO 17
<211> LENGTH: 23
<212> TYPE: DNA
<213> ORGANISM: Artificial Sequence
<220> FEATURE:
<223> OTHER INFORMATION: Degenerate oligonucleotide primer derived from
      SEQ ID NO: 2

<400> SEQUENCE: 17
cgtcacagrt trtccaccat ttc                                          23

<210> SEQ ID NO 18
<211> LENGTH: 23
<212> TYPE: DNA
<213> ORGANISM: Artificial Sequence
<220> FEATURE:
<223> OTHER INFORMATION: Degenerate oligonucleotide primer derived from
      SEQ ID NO: 2

<400> SEQUENCE: 18
cgtcacagrt trtcgaccat ttc                                          23

<210> SEQ ID NO 19
<211> LENGTH: 20
<212> TYPE: DNA
<213> ORGANISM: Artificial Sequence
<220> FEATURE:
<223> OTHER INFORMATION: Degenerate oligonucleotide primer derived from
      SEQ ID NO: 2

<400> SEQUENCE: 19
gaggggcagc tttgtggaga                                              20

<210> SEQ ID NO 20
<211> LENGTH: 26
<212> TYPE: DNA
<213> ORGANISM: Artificial Sequence
<220> FEATURE:
<223> OTHER INFORMATION: Degenerate oligonucleotide primer derived from
      SEQ ID NO: 2
```

-continued

```
<400> SEQUENCE: 20
cagcataggc cagccccagg atgcct                                          26

<210> SEQ ID NO 21
<211> LENGTH: 24
<212> TYPE: DNA
<213> ORGANISM: Artificial Sequence
<220> FEATURE:
<223> OTHER INFORMATION: Degenerate oligonucleotide primer derived from
      SEQ ID NO: 2

<400> SEQUENCE: 21
gtgatggcag caatgttggc acgc                                            24

<210> SEQ ID NO 22
<211> LENGTH: 17
<212> TYPE: DNA
<213> ORGANISM: Artificial Sequence
<220> FEATURE:
<223> OTHER INFORMATION: Degenerate oligonucleotide primer
<220> FEATURE:
<221> NAME/KEY: misc_feature
<222> LOCATION: (1)...(17)
<223> OTHER INFORMATION: n = A,T,C or G

<400> SEQUENCE: 22
gaygargagc cngagga                                                    17

<210> SEQ ID NO 23
<211> LENGTH: 17
<212> TYPE: DNA
<213> ORGANISM: Artificial Sequence
<220> FEATURE:
<223> OTHER INFORMATION: Degenerate oligonucleotide primer
<220> FEATURE:
<221> NAME/KEY: misc_feature
<222> LOCATION: (1)...(17)
<223> OTHER INFORMATION: n = A,T,C or G

<400> SEQUENCE: 23
gaygargagc cngaaga                                                    17

<210> SEQ ID NO 24
<211> LENGTH: 17
<212> TYPE: DNA
<213> ORGANISM: Artificial Sequence
<220> FEATURE:
<223> OTHER INFORMATION: Degenerate oligonucleotide primer
<220> FEATURE:
<221> NAME/KEY: misc_feature
<222> LOCATION: (1)...(17)
<223> OTHER INFORMATION: n = A,T,C or G

<400> SEQUENCE: 24
gaygargaac cngagga                                                    17

<210> SEQ ID NO 25
<211> LENGTH: 17
<212> TYPE: DNA
<213> ORGANISM: Artificial Sequence
<220> FEATURE:
<223> OTHER INFORMATION: Degenerate oligonucleotide primer
<220> FEATURE:
<221> NAME/KEY: misc_feature
<222> LOCATION: (1)...(17)
<223> OTHER INFORMATION: n = A,T,C or G

<400> SEQUENCE: 25
```
gaygargaac cngaaga                                          17

<210> SEQ ID NO 26
<211> LENGTH: 15
<212> TYPE: DNA
<213> ORGANISM: Artificial Sequence
<220> FEATURE:
<223> OTHER INFORMATION: Degenerate oligonucleotide primer
<220> FEATURE:
<221> NAME/KEY: misc_feature
<222> LOCATION: (1)...(15)
<223> OTHER INFORMATION: n = A,T,C or G

<400> SEQUENCE: 26
rttrtcnacc atttc                                            15

<210> SEQ ID NO 27
<211> LENGTH: 15
<212> TYPE: DNA
<213> ORGANISM: Artificial Sequence
<220> FEATURE:
<223> OTHER INFORMATION: Degenerate oligonucleotide primer
<220> FEATURE:
<221> NAME/KEY: misc_feature
<222> LOCATION: (1)...(15)
<223> OTHER INFORMATION: n = A,T,C or G

<400> SEQUENCE: 27
rttrtcnacc atctc                                            15

<210> SEQ ID NO 28
<211> LENGTH: 17
<212> TYPE: DNA
<213> ORGANISM: Artificial Sequence
<220> FEATURE:
<223> OTHER INFORMATION: Degenerate oligonucleotide primer
<220> FEATURE:
<221> NAME/KEY: misc_feature
<222> LOCATION: (1)...(17)
<223> OTHER INFORMATION: n = A,T,C or G

<400> SEQUENCE: 28
tcnaccatyt cnacaaa                                          17

<210> SEQ ID NO 29
<211> LENGTH: 17
<212> TYPE: DNA
<213> ORGANISM: Artificial Sequence
<220> FEATURE:
<223> OTHER INFORMATION: Degenerate oligonucleotide primer
<220> FEATURE:
<221> NAME/KEY: misc_feature
<222> LOCATION: (1)...(17)
<223> OTHER INFORMATION: n = A,T,C or G

<400> SEQUENCE: 29
tcnaccatyt cnacgaa                                          17

<210> SEQ ID NO 30
<211> LENGTH: 27
<212> TYPE: DNA
<213> ORGANISM: Artificial Sequence
<220> FEATURE:
<223> OTHER INFORMATION: Degenerate oligonucleotide primer

<400> SEQUENCE: 30
atattctaga gaygargagc cagaaga                               27

<210> SEQ ID NO 31
<211> LENGTH: 27
<212> TYPE: DNA
<213> ORGANISM: Artificial Sequence
<220> FEATURE:
<223> OTHER INFORMATION: Degenerate oligonucleotide primer

<400> SEQUENCE: 31
atattctaga gaygargagc cggaaga                                27

<210> SEQ ID NO 32
<211> LENGTH: 27
<212> TYPE: DNA
<213> ORGANISM: Artificial Sequence
<220> FEATURE:
<223> OTHER INFORMATION: Degenerate oligonucleotide primer

<400> SEQUENCE: 32
atattctaga gaygargagc ccgaaga                                27

<210> SEQ ID NO 33
<211> LENGTH: 27
<212> TYPE: DNA
<213> ORGANISM: Artificial Sequence
<220> FEATURE:
<223> OTHER INFORMATION: Degenerate oligonucleotide primer

<400> SEQUENCE: 33
atattctaga gaygargagc ctgaaga                                27

<210> SEQ ID NO 34
<211> LENGTH: 30
<212> TYPE: DNA
<213> ORGANISM: Artificial Sequence
<220> FEATURE:
<223> OTHER INFORMATION: Degenerate oligonucleotide primer
<220> FEATURE:
<221> NAME/KEY: misc_feature
<222> LOCATION: (1)...(30)
<223> OTHER INFORMATION: n = A,T,C or G

<400> SEQUENCE: 34
acacgaattc ttrtcnacca tytcaacaaa                             30

<210> SEQ ID NO 35
<211> LENGTH: 30
<212> TYPE: DNA
<213> ORGANISM: Artificial Sequence
<220> FEATURE:
<223> OTHER INFORMATION: Degenerate oligonucleotide primer
<220> FEATURE:
<221> NAME/KEY: misc_feature
<222> LOCATION: (1)...(30)
<223> OTHER INFORMATION: n = A,T,C or G

<400> SEQUENCE: 35
acacgaattc ttrtcnacca tytcgacaaa                             30

<210> SEQ ID NO 36
<211> LENGTH: 30
<212> TYPE: DNA
<213> ORGANISM: Artificial Sequence
<220> FEATURE:
<223> OTHER INFORMATION: Degenerate oligonucleotide primer
<220> FEATURE:
<221> NAME/KEY: misc_feature
<222> LOCATION: (1)...(30)
<223> OTHER INFORMATION: n = A,T,C or G

```
<400> SEQUENCE: 36
acacgaattc ttrtcnacca tytccacaaa                                30

<210> SEQ ID NO 37
<211> LENGTH: 30
<212> TYPE: DNA
<213> ORGANISM: Artificial Sequence
<220> FEATURE:
<223> OTHER INFORMATION: Degenerate oligonucleotide primer
<220> FEATURE:
<221> NAME/KEY: misc_feature
<222> LOCATION: (1)...(30)
<223> OTHER INFORMATION: n = A,T,C or G

<400> SEQUENCE: 37
acacgaattc ttrtcnacca tytctacaaa                                30

<210> SEQ ID NO 38
<211> LENGTH: 21
<212> TYPE: DNA
<213> ORGANISM: Artificial Sequence
<220> FEATURE:
<223> OTHER INFORMATION: Degenerate oligonucleotide primer

<400> SEQUENCE: 38
aagagcccgg ccggaggggc a                                         21

<210> SEQ ID NO 39
<211> LENGTH: 21
<212> TYPE: DNA
<213> ORGANISM: Artificial Sequence
<220> FEATURE:
<223> OTHER INFORMATION: Degenerate oligonucleotide primer

<400> SEQUENCE: 39
aaagctgccc ctccggccgg g                                         21

<210> SEQ ID NO 40
<211> LENGTH: 26
<212> TYPE: DNA
<213> ORGANISM: Artificial Sequence
<220> FEATURE:
<223> OTHER INFORMATION: Degenerate oligonucleotide primer

<400> SEQUENCE: 40
agctcgttta gtgaaccgtc agatcg                                    26

<210> SEQ ID NO 41
<211> LENGTH: 26
<212> TYPE: DNA
<213> ORGANISM: Artificial Sequence
<220> FEATURE:
<223> OTHER INFORMATION: Degenerate oligonucleotide primer

<400> SEQUENCE: 41
acctacaggt ggggtctttc attccc                                    26

<210> SEQ ID NO 42
<211> LENGTH: 1368
<212> TYPE: DNA
<213> ORGANISM: Homo sapiens

<400> SEQUENCE: 42
gagaccgacg aagagcccga ggagcccggc cggaggggca gctttgtgga gatggtggac    60
aacctgaggg gcaagtcggg gcagggctac tacgtggaga tgaccgtggg cagccccccg    120
```

```
cagacgctca acatcctggt ggatacaggc agcagtaact ttgcagtggg tgctgccccc    180
caccccttcc tgcatcgcta ctaccagagg cagctgtcca gcacataccg ggacctccgg    240
aagggtgtgt atgtgcccta cacccagggc aagtgggaag gggagctggg caccgacctg    300
gtaagcatcc cccatggccc caacgtcact gtgcgtgcca acattgctgc catcactgaa    360
tcagacaagt tcttcatcaa cggctccaac tgggaaggca tcctggggct ggcctatgct    420
gagattgcca ggcctgacga ctccctggag cctttctttg actctctggt aaagcagacc    480
cacgttccca acctcttctc cctgcagctt tgtggtgctg gcttccccct caaccagtct    540
gaagtgctgg cctctgtcgg agggagcatg atcattggag gtatcgacca ctcgctgtac    600
acaggcagtc tctggtatac acccatccgg cgggagtggt attatgaggt gatcattgtg    660
cgggtggaga tcaatggaca ggatctgaaa atggactgca aggagtacaa ctatgacaag    720
agcattgtgg acagtggcac caccaacctt cgtttgccca agaaagtgtt tgaagctgca    780
gtcaaatcca tcaaggcagc ctcctccacg gagaagttcc ctgatggttt ctggctagga    840
gagcagctgg tgtgctggca agcaggcacc acccccttgga acatttttccc agtcatctca    900 ctctacctaa tgggtgaggt taccaaccag tccttccgca tcaccatcct tccgcagcaa    960
tacctgcggc cagtgaaga tgtgccacgt tcccaagacg actgttacaa gtttgccatc    1020
tcacagtcat ccacgggcac tgttatggga gctgttatca tggagggctt ctacgttgtc    1080
tttgatcggg cccgaaaacg aattggcttt gctgtcagcg cttgccatgt gcacgatgag    1140
ttcaggacgg cagcggtgga aggccctttt gtcaccttgg acatggaaga ctgtggctac    1200
aacattccac agacagatga gtcaacccctc atgaccatag cctatgtcat ggctgccatc    1260
tgcgccctct tcatgctgcc actctgcctc atggtgtgtc agtggcgctg cctccgctgc    1320
ctgcgccagc agcatgatga ctttgctgat gacatctccc tgctgaag                 1368
```

<210> SEQ ID NO 43
<211> LENGTH: 456
<212> TYPE: PRT
<213> ORGANISM: Homo sapiens
<400> SEQUENCE: 43

```
Glu Thr Asp Glu Glu Pro Glu Pro Gly Arg Arg Gly Ser Phe Val
 1               5                  10                  15

Glu Met Val Asp Asn Leu Arg Gly Lys Ser Gly Gln Gly Tyr Tyr Val
                20                  25                  30

Glu Met Thr Val Gly Ser Pro Pro Gln Thr Leu Asn Ile Leu Val Asp
            35                  40                  45

Thr Gly Ser Ser Asn Phe Ala Val Gly Ala Ala Pro His Pro Phe Leu
        50                  55                  60

His Arg Tyr Tyr Gln Arg Gln Leu Ser Ser Thr Tyr Arg Asp Leu Arg
    65                  70                  75                  80

Lys Gly Val Tyr Val Pro Tyr Thr Gln Gly Lys Trp Glu Gly Glu Leu
                    85                  90                  95

Gly Thr Asp Leu Val Ser Ile Pro His Gly Pro Asn Val Thr Val Arg
                100                 105                 110

Ala Asn Ile Ala Ala Ile Thr Glu Ser Asp Lys Phe Phe Ile Asn Gly
            115                 120                 125

Ser Asn Trp Glu Gly Ile Leu Gly Leu Ala Tyr Ala Glu Ile Ala Arg
        130                 135                 140

Pro Asp Asp Ser Leu Glu Pro Phe Phe Asp Ser Leu Val Lys Gln Thr
```

```
145                 150                 155                 160
His Val Pro Asn Leu Phe Ser Leu Gln Leu Cys Gly Ala Gly Phe Pro
                165                 170                 175
Leu Asn Gln Ser Glu Val Leu Ala Ser Val Gly Gly Ser Met Ile Ile
            180                 185                 190
Gly Gly Ile Asp His Ser Leu Tyr Thr Gly Ser Leu Trp Tyr Thr Pro
        195                 200                 205
Ile Arg Arg Glu Trp Tyr Tyr Glu Val Ile Ile Val Arg Val Glu Ile
    210                 215                 220
Asn Gly Gln Asp Leu Lys Met Asp Cys Lys Glu Tyr Asn Tyr Asp Lys
225                 230                 235                 240
Ser Ile Val Asp Ser Gly Thr Thr Asn Leu Arg Leu Pro Lys Lys Val
                245                 250                 255
Phe Glu Ala Ala Val Lys Ser Ile Lys Ala Ala Ser Ser Thr Glu Lys
            260                 265                 270
Phe Pro Asp Gly Phe Trp Leu Gly Glu Gln Leu Val Cys Trp Gln Ala
        275                 280                 285
Gly Thr Thr Pro Trp Asn Ile Phe Pro Val Ile Ser Leu Tyr Leu Met
    290                 295                 300
Gly Glu Val Thr Asn Gln Ser Phe Arg Ile Thr Ile Leu Pro Gln Gln
305                 310                 315                 320
Tyr Leu Arg Pro Val Glu Asp Val Ala Thr Ser Gln Asp Asp Cys Tyr
                325                 330                 335
Lys Phe Ala Ile Ser Gln Ser Ser Thr Gly Thr Val Met Gly Ala Val
            340                 345                 350
Ile Met Glu Gly Phe Tyr Val Val Phe Asp Arg Ala Arg Lys Arg Ile
        355                 360                 365
Gly Phe Ala Val Ser Ala Cys His Val His Asp Glu Phe Arg Thr Ala
    370                 375                 380
Ala Val Glu Gly Pro Phe Val Thr Leu Asp Met Glu Asp Cys Gly Tyr
385                 390                 395                 400
Asn Ile Pro Gln Thr Asp Glu Ser Thr Leu Met Thr Ile Ala Tyr Val
                405                 410                 415
Met Ala Ala Ile Cys Ala Leu Phe Met Leu Pro Leu Cys Leu Met Val
            420                 425                 430
Cys Gln Trp Arg Cys Leu Arg Cys Leu Arg Gln Gln His Asp Asp Phe
        435                 440                 445
Ala Asp Asp Ile Ser Leu Leu Lys
    450                 455

<210> SEQ ID NO 44
<211> LENGTH: 2348
<212> TYPE: DNA
<213> ORGANISM: Homo sapiens

<400> SEQUENCE: 44
ccatgccggc ccctcacagc cccgccggga gcccgagccc gctgcccagg ctggccgccg      60
ccgtgccgat gtagcgggct ccggatccca gcctctcccc tgctcccgtg ctctgcggat     120
ctcccctgac cgctctccac agcccggacc cgggggctgg cccagggccc tgcaggccct     180
ggcgtcctga tgcccccaag ctccctctcc tgagaagcca ccagcaccac ccagacttgg     240
gggcaggcgc cagggacgga cgtgggccag tgcgagccca gagggcccga aggccggggc     300
ccaccatggc ccaagccctg ccctggctcc tgctgtggat gggcgcggga gtgctgcctg     360
```

```
cccacggcac  ccagcacggc  atccggctgc  ccctgcgcag  cggcctgggg  ggcgcccccc    420
tggggctgcg  gctgccccgg  gagaccgacg  aagagcccga  ggagcccggc  cggaggggca    480
gctttgtgga  gatggtggac  aacctgaggg  gcaagtcggg  gcagggctac  tacgtggaga    540
tgaccgtggg  cagcccccg   cagacgctca  acatcctggt  ggatacaggc  agcagtaact    600
ttgcagtggg  tgctgccccc  cacccttcc   tgcatcgcta  ctaccagagg  cagctgtcca    660
gcacataccg  ggacctccgg  aagggtgtgt  atgtgcccta  cacccaggg   aagtgggaag    720 gggagctggg  caccgacctg  gtaagcatcc  cccatggccc  caacgtcact  gtgcgtgcca    780
acattgctgc  catcactgaa  tcagacaagt  tcttcatcaa  cggctccaac  tgggaaggca    840
tcctggggct  ggcctatgct  gagattgcca  ggcctgacga  ctccctggag  cctttctttg    900
actctctggt  aaagcagacc  cacgttccca  acctcttctc  cctgcagctt  tgtggtgctg    960
gcttccccct  caaccagtct  gaagtgctgg  cctctgtcgg  agggagcatg  atcattggag    1020
gtatcgacca  ctcgctgtac  acaggcagtc  tctggtatac  acccatccgg  cgggagtggt    1080
attatgaggt  gatcattgtg  cgggtggaga  tcaatggaca  ggatctgaaa  atggactgca    1140
aggagtacaa  ctatgacaag  agcattgtgg  acagtgcac   caccaacctt  cgtttgccca    1200
agaaagtgtt  tgaagctgca  gtcaaatcca  tcaaggcagc  ctcctccacg  gagaagttcc    1260
ctgatggttt  ctggctagga  gagcagctgg  tgtgctggca  agcaggcacc  acccccttgga   1320 acatttccc   agtcatctca  ctctacctaa  tgggtgaggt  taccaaccag  tccttccgca    1380
tcaccatcct  tccgcagcaa  tacctgcggc  cagtggaaga  tgtggccacg  tcccaagacg    1440
actgttacaa  gtttgccatc  tcacagtcat  ccacgggcac  tgttatggga  gctgttatca    1500
tggagggctt  ctacgttgtc  tttgatcggg  cccgaaaacg  aattggcttt  gctgtcagcg    1560
cttgccatgt  gcacgatgag  ttcaggacgg  cagcggtgga  aggcccttt   gtcaccttgg    1620 acatggaaga  ctgtggctac  aacattccac  agacagatga  gtcaaccctc  atgaccatag    1680
cctatgtcat  ggctgccatc  tgcgccctct  tcatgctgcc  actctgcctc  atggtgtgtc    1740
agtggcgctg  cctccgctgc  ctgcgccagc  agcatgatga  ctttgctgat  gacatctccc    1800
tgctgaagtg  aggaggccca  tgggcagaag  atagagattc  ccctggacca  cacctccgtg    1860
gttcactttg  gtcacaagta  ggagacacag  atggcacctg  tggccagagc  acctcaggac    1920 cctcccccacc caccaaatgc ctctgccttg atggagaagg aaaaggctgg caaggtgggt    1980
tccagggact  gtacctgtag  gaaacagaaa  agagaagaaa  gaagcactct  gctggcggga    2040
atactcttgg  tcacctcaaa  tttaagtcgg  gaaattctgc  tgcttgaaac  ttcagccctg    2100
aacctttgtc  caccattcct  ttaaattctc  caacccaaag  tattcttctt  ttcttagttt    2160
cagaagtact  ggcatcacac  gcaggttacc  ttggcgtgtg  tccctgtggt  accctggcag    2220
agaagagacc  aagcttgttt  ccctgctggc  caaagtcagt  aggagaggat  gcacagtttg    2280
ctatttgctt  tagagacagg  gactgtataa  acaagcctaa  cattggtgca  aagattgcct    2340
cttgaatt                                                                 2348
```

<210> SEQ ID NO 45
<211> LENGTH: 8
<212> TYPE: PRT
<213> ORGANISM: Artificial Sequence
<220> FEATURE:
<223> OTHER INFORMATION: Flag sequence

<400> SEQUENCE: 45

Asp Tyr Lys Asp Asp Asp Asp Lys

-continued

<210> SEQ ID NO 46
<211> LENGTH: 21
<212> TYPE: PRT
<213> ORGANISM: Homo sapiens

<400> SEQUENCE: 46

Met Ala Gln Ala Leu Pro Trp Leu Leu Leu Trp Met Gly Ala Gly Val
1               5                   10                  15

Leu Pro Ala His Gly
            20

<210> SEQ ID NO 47
<211> LENGTH: 24
<212> TYPE: PRT
<213> ORGANISM: Homo sapiens

<400> SEQUENCE: 47

Thr Gln His Gly Ile Arg Leu Pro Leu Arg Ser Gly Leu Gly Gly Ala
1               5                   10                  15

Pro Leu Gly Leu Arg Leu Pro Arg
            20

<210> SEQ ID NO 48
<211> LENGTH: 16080
<212> TYPE: DNA
<213> ORGANISM: Artificial Sequence
<220> FEATURE:
<223> OTHER INFORMATION: Expression Vector pCEK
<220> FEATURE:
<221> NAME/KEY: misc_feature
<222> LOCATION: (1)...(16080)
<223> OTHER INFORMATION: n = A,T,C or G

<400> SEQUENCE: 48

| | | |
|---|---|---|
| ttctcatgtt tgacagctta tcatcgcaga tccgggcaac gttgttgcat tgctgcaggc | 60 |
| gcagaactgg taggtatgga agatccgatg tacgggccag atatacgcgt tgacattgat | 120 |
| tattgactag ttattaatag taatcaatta cggggtcatt agttcatagc ccatatatgg | 180 |
| agttccgcgt tacataactt acggtaaatg gcccgcctgg ctgaccgccc aacgaccccc | 240 |
| gcccattgac gtcaataatg acgtatgttc ccatagtaac gccaataggg actttccatt | 300 |
| gacgtcaatg ggtggactat ttacggtaaa ctgcccactt ggcagtacat caagtgtatc | 360 |
| atatgccaag tacgccccct attgacgtca atgacgtaa atggcccgcc tggcattatg | 420 |
| cccagtacat gaccttatgg gactttccta cttggcagta catctacgta ttagtcatcg | 480 |
| ctattaccat ggtgatgcgg ttttggcagt acatcaatgg gcgtggatag cggtttgact | 540 |
| cacgggggatt tccaagtctc caccccattg acgtcaatgg gagtttgttt tggcaccaaa | 600 |
| atcaacggga ctttccaaaa tgtcgtaaca actccgcccc attgacgcaa atgggcggta | 660 |
| ggcgtgtacg gtgggaggtc tatataagca gagctctctg gctaactaga acccactg | 720 |
| cttactggct tatcgaaatt aatacgactc actatagggga gacccaagct ctgttgggct | 780 |
| cgcggttgag gacaaactct tcgcggtctt tccagtactc ttggatcgga acccgtcgg | 840 |
| cctccgaacg gtactccgcc accgagggac ctgagcgagt ccgcatcgac cggatcggaa | 900 |
| aacctctcga ctgttggggt gagtactccc tctcaaaagc gggcatgact tctgcgctaa | 960 |
| gattgtcagt ttccaaaaac gaggaggatt tgatattcac ctggcccgcg gtgatgcctt | 1020 |
| tgagggtggc cgcgtccatc tggtcagaaa agacaatctt tttgttgtca agcttgaggt | 1080 |

-continued

```
gtggcaggct tgagatctgg ccatacactt gagtgacaat gacatccact ttgcctttct    1140
ctccacaggt gtccactccc aggtccaact gcaggtcgac tctagacccg ggaattctg     1200
cagatatcca tcacactggc cgcactcgtc cccagcccgc ccgggagctg cgagccgcga    1260
gctggattat ggtggcctga gcagccaacg cagccgcagg agcccggagc ccttgcccct    1320
gcccgcgccg ccgcccgccg gggggaccag ggaagccgcc accggcccgc catgcccgcc    1380
cctcccagcc ccgccgggag cccgcgcccg ctgcccaggc tggccgccgc cgtgccgatg    1440
tagcgggctc cggatcccag cctctcccct gctcccgtgc tctgcggatc tccctgacc     1500
gctctccaca gcccggaccc ggggctggc ccagggccct gcaggccctg gcgtcctgat     1560
gcccccaagc tccctctcct gagaagccac cagcaccacc cagacttggg ggcaggcgcc    1620
agggacggac gtgggccagt gcgagcccag agggcccgaa ggccggggcc caccatggcc    1680
caagccctgc cctggctcct gctgtggatg gcgcgggag tgctgcctgc ccacggcacc     1740
cagcacggca tccggctgcc cctgcgcagc ggcctggggg gcgcccccct ggggctgcgg    1800
ctgccccggg agaccgacga agagcccgag gagcccggcc ggaggggcag ctttgtggag    1860
atggtggaca acctgagggg caagtcgggg cagggctact acgtggagat gaccgtgggc    1920
agcccccgc agacgctcaa catcctggtg gatacaggca gcagtaactt tgcagtgggt    1980
gctgccccc accccttcct gcatcgctac taccagaggc agctgtccag cacataccgg    2040
gacctccgga agggtgtgta tgtgccctac acccagggca agtgggaagg ggagctgggc    2100
accgacctgg taagcatccc ccatggcccc aacgtcactg tgcgtgccaa cattgctgcc    2160
atcactgaat cagacaagtt cttcatcaac ggctccaact gggaaggcat cctgggctg     2220
gcctatgctg agattgccag gcctgacgac tccctggagc cttctcttga ctctctggta    2280
aagcagaccc acgttcccaa cctcttctcc ctgcagcttt gtggtgctgg cttccccctc    2340
aaccagtctg aagtgctggc ctctgtcgga gggagcatga tcattggagg tatcgaccac    2400
tcgctgtaca caggcagtct ctggtataca cccatccggc gggagtggta ttatgaggtc    2460
atcattgtgc gggtggagat caatggacag gatctgaaaa tggactgcaa ggagtacaac    2520
tatgacaaga gcattgtgga cagtggcacc accaaccttc gtttgcccaa gaaagtgttt    2580
gaagctgcag tcaaatccat caaggcagcc tcctccacgg agaagttccc tgatggtttc    2640
tggctaggag agcagctggt gtgctggcaa gcaggcacca ccccttggaa cattttccca    2700
gtcatctcac tctacctaat gggtgaggtt accaaccagt ccttccgcat caccatcctt    2760
ccgcagcaat acctgcggcc agtggaagat gtggccacgt cccaagacga ctgttacaag    2820
tttgccatct cacagtcatc cacgggcact gttatgggag ctgttatcat ggaggcttc     2880
tacgttgtct ttgatcgggc ccgaaaacga attggctttg ctgtcagcgc ttgccatgtg    2940
cacgatgagt tcaggacggc agcggtggaa ggcccttttg tcaccttgga catggaagac    3000
tgtggctaca acattccaca gacagatgag tcaaccctca tgaccatagc ctatgtcatg    3060
gctgccatct cgcgccctct tcatgctgcc atctgcctca tggtgtgtca gtggcgctgc    3120
ctccgctgcc tgcgccagca gcatgatgac tttgctgatg acatctccct gctgaagtga    3180
ggaggcccat gggcagaaga tagagattcc cctggaccac acctccgtgg ttcactttgg    3240
tcacaagtag gagacacaga tggcacctgt ggccagagca cctcaggacc ctccccaccc    3300
accaaatgcc tctgccttga tggagaagga aaaggctggc aagtgggtt ccagggactg     3360
tacctgtagg aaacagaaaa gagaagaaag aagcactctg ctggcgggaa tactcttggt    3420
```

```
cacctcaaat ttaagtcggg aaattctgct gcttgaaact tcagccctga acctttgtcc    3480
accattcctt taaattctcc aacccaaagt attcttcttt tcttagtttc agaagtactg    3540
gcatcacacg caggttacct tggcgtgtgt ccctgtggta ccctggcaga gaagagacca    3600
agcttgtttc cctgctggcc aaagtcagta ggagaggatg cacagtttgc tatttgcttt    3660
agagacaggg actgtataaa caagcctaac attggtgcaa agattgcctc ttgaattaaa    3720
aaaaaaaact agattgacta tttatacaaa tgggggcggc tggaaagagg agaaggagag    3780
ggagtacaaa gacagggaat agtgggatca aagctaggaa aggcagaaac acaaccactc    3840
accagtccta gttttagacc tcatctccaa gatagcatcc catctcagaa gatgggtgtt    3900
gttttcaatg ttttcttttc tgtggttgca gcctgaccaa aagtgagatg ggaagggctt    3960
atctagccaa agagctcttt tttagctctc ttaaatgaag tgcccactaa gaagttccac    4020
ttaacacatg aatttctgcc atattaattt cattgtctct atctgaacca ccctttattc    4080
tacatatgat aggcagcact gaaatatcct aacccctaa gctccaggtg ccctgtggga    4140
gagcaactgg actatagcag ggctgggctc tgtcttcctg gtcataggct cactcttttcc    4200 cccaaatctt cctctggagc tttgcagcca aggtgctaaa aggaataggt aggagacctc    4260
ttctatctaa tccttaaaag cataatgttg aacattcatt caacagctga tgccctataa    4320
cccctgcctg gatttcttcc tattaggcta taagaagtag caagatcttt acataattca    4380
gagtggtttc attgccttcc taccctctct aatggcccct ccatttattt gactaaagca    4440
tcacacagtg gcactagcat tataccaaga gtatgagaaa tacagtgctt tatggctcta    4500
acattactgc cttcagtatc aaggctgcct ggagaaagga tggcagcctc agggcttcct    4560
tatgtcctcc accacaagag ctccttgatg aaggtcatct ttttcccta tcctgttctt    4620 cccctcccccg ctcctaatgg tacgtgggta cccaggctgg ttcttgggct aggtagtggg    4680
gaccaagttc attacctccc tatcagttct agcatagtaa actacggtac cagtgttagt    4740
gggaagagct gggttttcct agtatacccca ctgcatccta ctcctacctg gtcaacccgc    4800
tgcttccagg tatgggacct gctaagtgtg gaattacctg ataagggaga gggaaataca    4860
aggagggcct ctggtgttcc tggcctcagc cagctgccca caagccataa accaataaaa    4920
caagaatact gagtcagttt tttatctggg ttctcttcat tcccactgca cttggtgctg    4980
ctttggctga ctgggaacac cccataacta cagagtctga caggaagact ggagactgtc    5040
cacttctagc tcggaactta ctgtgtaaat aaactttcag aactgctacc atgaagtgaa    5100
aatgccacat tttgctttat aatttctacc catgttggga aaaactggct ttttcccagc    5160
cctttccagg gcataaaact caacccttc gatagcaagt cccatcagcc tattattttt    5220
ttaaagaaaa cttgcacttg ttttttcttt tacagttact tccttcctgc cccaaaatta    5280
taaactctaa gtgtaaaaaa aagtcttaac aacagcttct tgcttgtaaa aatatgtatt    5340
atacatctgt attttaaat tctgctcctg aaaaatgact gtcccattct ccactcactg    5400
catttggggc ctttcccatt ggtctgcatg tcttttatca ttgcaggcca gtggacagag    5460
ggagaaggga gaacagggggt cgccaacact tgtgttgctt tctgactgat cctgaacaag    5520
aaagagtaac actgaggcgc tcgctcccat gcacaactct ccaaaacact tatcctcctg    5580
caagagtggg ctttccgggt ctttactggg aagcagttaa gccccctcct cacccctttcc    5640 ttttttcttt ctttactcct ttggcttcaa aggatttttgg aaaagaaaca atatgcttta    5700
cactcatttt caatttctaa atttgcaggg gatactgaaa aatacggcag gtggcctaag    5760
gctgctgtaa agttgagggg agaggaaatc ttaagattac aagataaaaa acgaatcccc    5820
```

```
taaacaaaaa gaacaataga actggtcttc cattttgcca cctttcctgt tcatgacagc    5880
tactaacctg gagacagtaa catttcatta accaaagaaa gtgggtcacc tgacctctga    5940
agagctgagt actcaggcca ctccaatcac cctacaagat gccaaggagg tcccaggaag    6000
tccagctcct taaactgacg ctagtcaata aacctgggca agtgaggcaa gagaaatgag    6060
gaagaatcca tctgtgaggt gacaggcacg gatgaaagac aaagacggaa aagagtatca    6120
aaggcagaaa ggagatcatt tagttgggtc tgaaaggaaa agtnttttgct atccgacatg    6180 tactgctagt wcctgtaagc attttaggtc ccagaatgga aaaaaaaatc aagctatngg    6240
ttatataata atgnnnnnnn nnnnnnnnnn nntcgagcat gcatctagag ggccctattc    6300
tatagtgtca cctaaatgct agagctcgct gatcagcctc gactgtgcct tctagttgcc    6360
agccatctgt tgtttgcccc tccccgtgc cttccttgac cctggaaggt gccactccca    6420
ctgtcctttc ctaataaaat gaggaaattg catcgcattg tctgagtagg tgtcattcta    6480
ttctgggggg tggggtgggg caggacagca agggggagga ttgggaagac aatagcaggc    6540
atgctgggga tgcggtgggc tctatggctt ctgaggcgga agaaccagc tggggctcta    6600 gggggtatcc ccacgcgccc tgtagcggcg cattaagcgc ggcgggtgtg gtggttacgc    6660
gcagcgtgac cgctacactt gccagcgccc tagcgcccgc tcctttcgct ttcttccctt    6720
cctttctcgc cacgttcgcc ggctttcccc gtcaagctct aaatcggggc atccctttag    6780
ggttccgatt tagtgcttta cggcacctcg accccaaaaa acttgattag ggtgatggtt    6840
cacgtagtgg gccatcgccc tgatagacgg tttttcgccc tttgacgttg gagtccacgt    6900
tctttaatag tggactcttg ttccaaactg gaacaacact caaccctatc tcggtctatt    6960
cttttgattt ataaggggatt tgggggattt cggcctattg gttaaaaaat gagctgattt    7020
aacaaaaatt taacgcgaat tctagagccc cgccgccgga cgaactaaac ctgactacgg    7080
catctctgcc ccttcttcgc ggggcagtgc atgtaatccc ttcagttggt tggtacaact    7140
tgccaactgg gccctgttcc acatgtgaca cggggggga ccaaacacaa agggggtctc    7200
tgactgtagt tgacatcctt ataaatggat gtgcacattt gccaacactg agtggctttc    7260
atcctggagc agactttgca gtctgtggac tgcaacacaa cattgccttt atgtgtaact    7320
cttggctgaa gctcttacac caatgctggg ggacatgtac ctcccagggg cccaggaaga    7380
ctacgggagg ctacaccaac gtcaatcaga ggggcctgtg tagctaccga taagcggacc    7440
ctcaagaggg cattagcaat agtgtttata aggccccctt gttaaccta acgggtagc    7500 atatgcttcc cgggtagtag tatatactat ccagactaac cctaattcaa tagcatatgt    7560
tacccaacgg gaagcatatg ctatcgaatt agggttagta aaagggtcct aaggaacagc    7620
gatatctccc accccatgag ctgtcacggt tttatttaca tggggtcagg attccacgag    7680
ggtagtgaac cattttagtc acaagggcag tggctgaaga tcaaggagcg ggcagtgaac    7740
tctcctgaat cttcgcctgc ttcttcattc tccttcgttt agctaataga ataactgctg    7800
agttgtgaac agtaaggtgt atgtgaggtg ctcgaaaaca aggtttcagg tgacgccccc    7860
agaataaaat ttggacgggg ggttcagtgg tggcattgtg ctatgacacc aatataaccc    7920
tcacaaaccc cttgggcaat aaatactagt gtaggaatga acattctga atatctttaa    7980 caatagaaat ccatgggtgt gggacaagcc gtaaagactg gatgtccatc tcacacgaat    8040
ttatggctat gggcaacaca taatcctagt gcaatatgat actggggtta ttaagatgtg    8100
tcccaggcag ggaccaagac aggtgaacca tgttgttaca ctctatttgt aacaagggga    8160
```

```
aagagagtgg acgccgacag cagcggactc cactggttgt ctctaacacc cccgaaaatt    8220
aaacggggct ccacgccaat ggggcccata aacaaagaca agtggccact ctttttttg      8280
aaattgtgga gtgggggcac gcgtcagccc ccacacgccg ccctgcggtt ttggactgta    8340
aaataagggt gtaataactt ggctgattgt aaccccgcta accactgcgg tcaaaccact    8400
tgcccacaaa accactaatg gcaccccggg gaatacctgc ataagtaggt gggcgggcca    8460
agatagggc gcgattgctg cgatctggag gacaaaattac acacacttgc gcctgagcgc    8520
caagcacagg gttgttggtc ctcatattca cgaggtcgct gagagcacgg tgggctaatg    8580
ttgccatggg tagcatatac tacccaaata tctggatagc atatgctatc ctaatctata    8640
tctgggtagc ataggctatc ctaatctata tctgggtagc atatgctatc ctaatctata    8700
tctgggtagt atatgctatc ctaatttata tctgggtagc ataggctatc ctaatctata    8760
tctgggtagc atatgctatc ctaatctata tctgggtagt atatgctatc ctaatctgta    8820
tccgggtagc atatgctatc ctaatagaga ttagggtagt atatgctatc ctaatttata    8880
tctgggtagc atatactacc caaatatctg gatagcatat gctatcctaa tctatatctg    8940
ggtagcatat gctatcctaa tctatatctg gtagcatag gctatcctaa tctatatctg     9000
ggtagcatat gctatcctaa tctatatctg gtagtatat gctatcctaa tttatatctg     9060
ggtagcatag gctatcctaa tctatatctg gtagcatat gctatcctaa tctatatctg     9120
ggtagtatat gctatcctaa tctgtatccg gtagcatat gctatcctca tgcatataca     9180
gtcagcatat gatacccagt agtagagtgg gagtgctatc cttttgcatat gccgccacct   9240
cccaagggg cgtgaatttt cgctgcttgt ccttttcctg catgctggtt gctcccattc     9300
ttaggtgaat ttaaggaggc caggctaaag ccgtcgcatg tctgattgct caccaggtaa    9360
atgtcgctaa tgttttccaa cgcgagaagg tgttgagcgc ggagctgagt gacgtgacaa    9420
catgggtatg cccaattgcc ccatgttggg aggacgaaaa tggtgacaag acagatggcc    9480
agaaatacac caacagcacg catgatgtct actggggatt tattctttag tgcgggggaa    9540
tacacggctt ttaatacgat tgagggcgtc tcctaacaag ttacatcact cctgcccttc    9600
ctcaccctca tctccatcac ctccttcatc tccgtcatct ccgtcatcac cctccgcggc    9660
agccccttcc accataggtg gaaaccaggg aggcaaatct actccatcgt caaagctgca    9720
cacagtcacc ctgatattgc aggtaggagc gggctttgtc ataacaaggt ccttaatcgc    9780
atccttcaaa acctcagcaa atatatgagt ttgtaaaaag accatgaaat aacagacaat    9840
ggactcccct agcgggccag gttgtgggcc gggtccaggg gccattccaa aggggagacg    9900
actcaatggt gtaagacgac attgtggaat agcaagggca gttcctcgcc ttaggttgta    9960
aagggaggtc ttactacctc catatacgaa cacaccggcg acccaagttc cttcgtcggt   10020
agtcctttct acgtgactcc tagccaggag agctcttaaa ccttctgcaa tgttctcaaa   10080
tttcgggttg gaacctcctt gaccacgatg ctttccaaac caccctcctt ttttgcgcct   10140
gcctccatca ccctgacccc ggggtccagt gcttgggcct tctcctgggt catctgcggg   10200
gccctgctct atcgctcccg ggggcacgtc aggctcacca tctgggccac cttcttggtg   10260
gtattcaaaa taatcggctt cccctacagg gtggaaaaat ggccttctac ctggaggggg   10320
cctgcgcggt ggagacccgg atgatgatga ctgactactg ggactcctgg gcctcttttc   10380
tccacgtcca cgacctctcc ccctggctct ttcacgactt ccccccctgg ctctttcacg   10440
tcctctaccc cggcggcctc cactacctcc tcgaccccgg cctccactac ctcctcgacc   10500
ccggcctcca ctgcctcctc gaccccggcc tccacctcct gctcctgccc ctcctgctcc   10560
```

```
tgcccctcct cctgctcctg cccctcctgc ccctcctgct cctgcccctc ctgcccctcc    10620
tgctcctgcc cctcctgccc ctcctgctcc tgcccctcct gcccctcctc ctgctcctgc    10680
ccctcctgcc cctcctcctg ctcctgcccc tcctgcccct cctgctcctg cccctcctgc    10740
ccctcctgct cctgcccctc ctgcccctcc tgctcctgcc cctcctgctc ctgcccctcc    10800
tgctcctgcc cctcctgctc ctgcccctcc tgcccctcct gcccctcctc ctgctcctgc    10860
ccctcctgct cctgcccctc ctgcccctcc tgcccctcct gctcctgccc ctcctcctgc    10920
tcctgcccct cctgcccctc ctgcccctcc tcctgctcct gcccctcctg cccctcctcc    10980
tgctcctgcc cctcctcctg ctcctgcccc tcctgcccct cctgcccctc ctcctgctcc    11040
tgcccctcct gcccctcctc ctgctcctgc ccctcctcct gctcctgccc ctcctgcccc    11100
tcctgcccct cctcctgctc ctgcccctcc tcctgctcct gcccctcctg cccctcctgc    11160
ccctcctgcc cctcctcctg ctcctgcccc tcctcctgct cctgcccctc ctgctcctgc    11220
ccctcccgct cctgctcctg ctcctgttcc accgtgggtc cctttgcagc caatgcaact    11280
tggacgtttt tggggtctcc ggacaccatc tctatgtctt ggccctgatc ctgagccgcc    11340
cggggctcct ggtcttccgc ctcctcgtcc tcgtcctctt cccgtcctc gtccatggtt     11400 atcaccccc cttctttgag gtccactgcc gccggagcct tctggtccag atgtgtctcc     11460
cttctctcct aggccatttc caggtcctgt acctggcccc tcgtcagaca tgattcacac    11520
taaaagagat caatagacat ctttattaga cgacgctcag tgaatacagg gagtgcagac    11580
tcctgccccc tccaacagcc cccccaccct catcccttc atggtcgctg tcagacagat     11640
ccaggtctga aaattcccca tcctccgaac catcctcgtc ctcatcacca attactcgca    11700
gcccggaaaa ctcccgctga acatcctcaa gatttgcgtc ctgagcctca agccaggcct    11760
caaattcctc gtccccttt ttgctggacg gtagggatgg ggattctcgg gaccctcct     11820 cttcctcttc aaggtcacca gacagagatg ctactgggc aacggaagaa aagctgggtg     11880
cggcctgtga ggatcagctt atcgatgata agctgtcaaa catgagaatt cttgaagacg    11940
aaagggcctc gtgatacgcc tattttata ggttaatgtc atgataataa tggtttctta     12000
gacgtcaggt ggcacttttc ggggaaatgt gcgcggaacc cctatttgtt tatttttcta    12060
aatacattca aatatgtatc cgctcatgag acaataaccc tgataaatgc ttcaataata    12120
ttgaaaaagg aagagtatga gtattcaaca tttccgtgtc gcccttattc ccttttttgc    12180
ggcattttgc cttcctgttt ttgctcaccc agaaacgctg gtgaaagtaa agatgctga    12240 agatcagttg ggtgcacgag tgggttacat cgaactggat ctcaacagcg gtaagatcct    12300
tgagagtttt cgccccgaag aacgttttcc aatgatgagc acttttaaag ttctgctatg    12360
tggcgcggta ttatcccgtg ttgacgccgg gcaagagcaa ctcggtcgcc gcatacacta    12420
ttctcagaat gacttggttg agtactcacc agtcacagaa aagcatctta cggatggcat    12480
gacagtaaga gaattatgca gtgctgccat aaccatgagt gataacactg cggccaactt    12540
acttctgaca acgatcggag gaccgaagga gctaaccgct tttttgcaca acatggggga    12600
tcatgtaact cgccttgatc gttgggaacc ggagctgaat gaagccatac caaacgacga    12660
gcgtgacacc acgatgcctg cagcaatggc aacaacgttg cgcaaactat taactggcga    12720
actacttact ctagcttccc ggcaacaatt aatagactgg atggaggcgg ataaagttgc    12780
aggaccactt ctgcgctcgg cccttccggc tggctggttt attgctgata atctggagc     12840 cggtgagcgt gggtctcgcg gtatcattgc agcactgggg ccagatggta agccctcccg    12900
```

```
tatcgtagtt atctacacga cggggagtca ggcaactatg gatgaacgaa atagacagat   12960
cgctgagata ggtgcctcac tgattaagca ttggtaactg tcagaccaag tttactcata   13020
tatactttag attgatttaa aacttcattt ttaatttaaa aggatctagg tgaagatcct   13080
ttttgataat ctcatgacca aaatccctta acgtgagttt tcgttccact gagcgtcaga   13140
ccccgtagaa aagatcaaag gatcttcttg agatcctttt tttctgcgcg taatctgctg   13200
cttgcaaaca aaaaaaccac cgctaccagc ggtggtttgt ttgccggatc aagagctacc   13260
aactcttttt ccgaaggtaa ctggcttcag cagagcgcag ataccaaata ctgtccttct   13320
agtgtagccg tagttaggcc accacttcaa gaactctgta gcaccgccta catacctcgc   13380
tctgctaatc ctgttaccag tggctgctgc cagtggcgat aagtcgtgtc ttaccgggtt   13440
ggactcaaga cgatagttac cggataaggc gcagcggtcg ggctgaacgg ggggttcgtg   13500
cacacagccc agcttggagc gaacgaccta caccgaactg agatacctac agcgtgagct   13560
atgagaaagc gccacgcttc ccgaagggag aaaggcggac aggtatccgg taagcggcag   13620
ggtcggaaca ggagagcgca cgagggagct tccagggga acgcctggt atctttatag   13680
tcctgtcggg tttcgccacc tctgacttga gcgtcgattt ttgtgatgct cgtcaggggg   13740
gcggagccta tggaaaaacg ccagcaacgc ggccttttta cggttcctgg ccttttgctg   13800
gccgcgtgc ggctgctgga gatggcggac gcgatggata tgttctgcca agggttggtt   13860
tgcgcattca cagttctccg caagaattga ttggctccaa ttcttggagt ggtgaatccg   13920
ttagcgaggt gccgccggct tccattcagg tcgaggtggc ccggctccat gcaccgcgac   13980
gcaacgcggg gaggcagaca aggtataggg cggcgcctac aatccatgcc aacccgttcc   14040
atgtgctcgc cgaggcggca taaatcgccg tgacgatcag cggtccagtg atcgaagtta   14100
ggctggtaag agccgcgagc gatccttgaa gctgtccctg atggtcgtca tctacctgcc   14160
tggacagcat ggcctgcaac gcgggcatcc cgatgccgcc ggaagcgaga agaatcataa   14220
tggggaaggc catccagcct cgcgtcgcga acgccagcaa gacgtagccc agcgcgtcgg   14280
ccgccatgcc ctgcttcatc cccgtggccc gttgctcgcg tttgctgcg gtgtccccgg   14340
aagaaatata tttgcatgtc tttagttcta tgatgacaca accccgccc agcgtcttgt   14400
cattggcgaa ttcgaacacg cagatgcagt cggggcggcg cggtcccagg tccacttcgc   14460
atattaaggt gacgcgtgtg gcctcgaaca ccgagcgacc ctgcagcgac ccgcttaaca   14520
gcgtcaacag cgtgccgcag atcccgggca atgagatatg aaaaagcctg aactcaccgc   14580
gacgtctgtc gagaagtttc tgatcgaaaa gttcgacagc gtctccgacc tgatgcagct   14640
ctcggagggc gaagaatctc gtgctttcag cttcgatgta ggagggcgtg gatatgtcct   14700
gcgggtaaat agctgcgccg atggtttcta caaagatcgt tagtgggatc ggcactttgc   14760
atcggccgcg ctccccgatt ccggaagtgc ttgacattgg ggaattcagc gagagcctga   14820
cctattgcat ctcccgccgt gcacagggtg tcacgttgca agacctgcct gaaaccgaac   14880
tgcccgctgt tctgcagccg gtcgcggagg ccatggatgc gatcgctgcg gccgatctta   14940
gccagacgag cgggttcggc ccattcggac cgcaaggaat cggtcaatac actacatggc   15000
gtgatttcat atgcgcgatt gctgatcccc atgtgtatca ctggcaaact gtgatggacg   15060
acaccgtcag tgcgtccgtc gcgcaggctc tcgatgagct gatgctttgg gccgaggact   15120
gccccgaagt ccggcacctc gtgcacgcgg atttcggctc caacaatgtc ctgacggaca   15180
atggccgcat aacagcggtc attgactgga gcgaggcgat gttcgggat cccaatacg   15240
aggtcgccaa catcttcttc tggaggccgt ggttggcggg tatggagcag cagacgcgct   15300
```

```
acttcgagcg gaggcatccg gagcttgcag gatcgccgcg gctccgggcg tatatgctcc    15360
gcattggtct tgaccaactc tatcagagct tggttgacgg caatttcgat gatgcagctt    15420
gggcgcaggg tcgatgcgac gcaatcgtcc gatccggagc cgggactgtc gggcgtacac    15480
aaatcgcccg cagaagcgcg gccgtctgga ccgatggctg tgtagaagta ctcgccgata    15540
gtggaaacgg gagatggggg aggctaactg aaacacggaa ggagacaata ccggaaggaa    15600
cccgcgctat gacggcaata aaaagacaga ataaaacgca cgggtgttgg gtcgtttgtt    15660
cataaacgcg gggttcggtc ccagggctgg cactctgtcg ataccccacc gagacccat     15720 tggggccaat acgcccgcgt ttcttccttt tccccacccc accccccaag ttcgggtgaa    15780
ggcccagggc tcgcagccaa cgtcggggcg gcaggccctg ccatagccac tggccccgtg    15840
ggttagggac ggggtccccc atggggaatg gtttatggtt cgtgggggtt attattttgg    15900
gcgttgcgtg gggtctggtc cacgactgga ctgagcagac agaccatgg tttttggatg     15960 gcctgggcat ggaccgcatg tactggcgcg acacgaacac cgggcgtctg tggctgccaa    16020
acaccccgga ccccaaaaa ccaccgcgcg gatttctggc gtgccaagct agtcgaccaa     16080
```

<210> SEQ ID NO 49
<211> LENGTH: 32
<212> TYPE: DNA
<213> ORGANISM: Homo sapiens

<400> SEQUENCE: 49
cccggccgga ggggcagctt tgtggagatg gt                                  32

<210> SEQ ID NO 50
<211> LENGTH: 11
<212> TYPE: PRT
<213> ORGANISM: Homo sapiens

<400> SEQUENCE: 50

Pro Gly Arg Arg Gly Ser Phe Val Glu Met Val
1               5                   10

<210> SEQ ID NO 51
<211> LENGTH: 5
<212> TYPE: PRT
<213> ORGANISM: Homo sapiens

<400> SEQUENCE: 51

Val Asn Leu Asp Ala
1               5

<210> SEQ ID NO 52
<211> LENGTH: 9
<212> TYPE: PRT
<213> ORGANISM: Artificial Sequence
<220> FEATURE:
<223> OTHER INFORMATION: Synthetic oligopeptide substrate

<400> SEQUENCE: 52

Ser Glu Val Asn Leu Asp Ala Glu Phe
1               5

<210> SEQ ID NO 53
<211> LENGTH: 30
<212> TYPE: PRT
<213> ORGANISM: Artificial Sequence
<220> FEATURE:
<223> OTHER INFORMATION: Synthetic oligopeptide substrate -continued

<400> SEQUENCE: 53

Ala Asp Arg Gly Leu Thr Thr Arg Pro Gly Ser Gly Leu Thr Asn Ile
1               5                   10                  15

Lys Thr Glu Glu Ile Ser Glu Val Asn Leu Asp Ala Glu Phe
            20                  25                  30

<210> SEQ ID NO 54
<211> LENGTH: 5
<212> TYPE: PRT
<213> ORGANISM: Homo sapiens
<220> FEATURE:
<223> OTHER INFORMATION: Wild type Amyloid Precursor Protein cleavage
      site (fragment)

<400> SEQUENCE: 54

Val Lys Met Asp Ala
1               5

<210> SEQ ID NO 55
<211> LENGTH: 24
<212> TYPE: PRT
<213> ORGANISM: Homo sapiens

<400> SEQUENCE: 55

Glu Thr Asp Glu Glu Pro Glu Glu Pro Gly Arg Arg Gly Ser Phe Val
1               5                   10                  15

Glu Met Val Asp Asn Leu Arg Gly
            20

<210> SEQ ID NO 56
<211> LENGTH: 15
<212> TYPE: PRT
<213> ORGANISM: Homo sapiens

<400> SEQUENCE: 56

Ile Gly Phe Ala Val Ser Ala Cys His Val His Asp Glu Phe Arg
1               5                   10                  15

<210> SEQ ID NO 57
<211> LENGTH: 419
<212> TYPE: PRT
<213> ORGANISM: Homo sapiens

<400> SEQUENCE: 57

Met Ala Gln Ala Leu Pro Trp Leu Leu Leu Trp Met Gly Ala Gly Val
1               5                   10                  15

Leu Pro Ala His Gly Thr Gln His Gly Ile Arg Leu Pro Leu Arg Ser
            20                  25                  30

Gly Leu Gly Gly Ala Pro Leu Gly Leu Arg Leu Pro Arg Glu Thr Asp
        35                  40                  45

Glu Glu Pro Glu Glu Pro Gly Arg Arg Gly Ser Phe Val Glu Met Val
    50                  55                  60

Asp Asn Leu Arg Gly Lys Ser Gly Gln Gly Tyr Tyr Val Glu Met Thr
65                  70                  75                  80

Val Gly Ser Pro Pro Gln Thr Leu Asn Ile Leu Val Asp Thr Gly Ser
                85                  90                  95

Ser Asn Phe Ala Val Gly Ala Ala Pro His Pro Phe Leu His Arg Tyr
            100                 105                 110

Tyr Gln Arg Gln Leu Ser Ser Thr Tyr Arg Asp Leu Arg Lys Gly Val
        115                 120                 125

```
Tyr Val Pro Tyr Thr Gln Gly Lys Trp Glu Gly Glu Leu Gly Thr Asp
        130                 135                 140

Leu Val Ser Ile Pro His Gly Pro Asn Val Thr Val Arg Ala Asn Ile
145                 150                 155                 160

Ala Ala Ile Thr Glu Ser Asp Lys Phe Phe Ile Asn Gly Ser Asn Trp
                165                 170                 175

Glu Gly Ile Leu Gly Leu Ala Tyr Ala Glu Ile Ala Arg Pro Asp Asp
            180                 185                 190

Ser Leu Glu Pro Phe Phe Asp Ser Leu Val Lys Gln Thr His Val Pro
        195                 200                 205

Asn Leu Phe Ser Leu Gln Leu Cys Gly Ala Gly Phe Pro Leu Asn Gln
    210                 215                 220

Ser Glu Val Leu Ala Ser Val Gly Gly Ser Met Ile Ile Gly Gly Ile
225                 230                 235                 240

Asp His Ser Leu Tyr Thr Gly Ser Leu Trp Tyr Thr Pro Ile Arg Arg
                245                 250                 255

Glu Trp Tyr Tyr Glu Val Ile Ile Val Arg Val Glu Ile Asn Gly Gln
            260                 265                 270

Asp Leu Lys Met Asp Cys Lys Glu Tyr Asn Tyr Asp Lys Ser Ile Val
        275                 280                 285

Asp Ser Gly Thr Thr Asn Leu Arg Leu Pro Lys Lys Val Phe Glu Ala
    290                 295                 300

Ala Val Lys Ser Ile Lys Ala Ala Ser Ser Thr Glu Lys Phe Pro Asp
305                 310                 315                 320

Gly Phe Trp Leu Gly Glu Gln Leu Val Cys Trp Gln Ala Gly Thr Thr
                325                 330                 335

Pro Trp Asn Ile Phe Pro Val Ile Ser Leu Tyr Leu Met Gly Glu Val
            340                 345                 350

Thr Asn Gln Ser Phe Arg Ile Thr Ile Leu Pro Gln Gln Tyr Leu Arg
        355                 360                 365

Pro Val Glu Asp Val Ala Thr Ser Gln Asp Asp Cys Tyr Lys Phe Ala
    370                 375                 380

Ile Ser Gln Ser Ser Thr Gly Thr Val Met Gly Ala Val Ile Met Glu
385                 390                 395                 400

Gly Phe Tyr Val Val Phe Asp Arg Ala Arg Lys Arg Ile Gly Phe Ala
                405                 410                 415

Val Ser Ala

<210> SEQ ID NO 58
<211> LENGTH: 407
<212> TYPE: PRT
<213> ORGANISM: Homo sapiens

<400> SEQUENCE: 58

Glu Thr Asp Glu Glu Pro Glu Glu Pro Gly Arg Arg Gly Ser Phe Val
  1               5                  10                  15

Glu Met Val Asp Asn Leu Arg Gly Lys Ser Gly Gln Gly Tyr Tyr Val
                20                  25                  30

Glu Met Thr Val Gly Ser Pro Pro Gln Thr Leu Asn Ile Leu Val Asp
            35                  40                  45

Thr Gly Ser Ser Asn Phe Ala Val Gly Ala Ala Pro His Pro Phe Leu
        50                  55                  60

His Arg Tyr Tyr Gln Arg Gln Leu Ser Ser Thr Tyr Arg Asp Leu Arg
65                  70                  75                  80
```

```
Lys Gly Val Tyr Val Pro Tyr Thr Gln Gly Lys Trp Glu Gly Glu Leu
                85                  90                  95

Gly Thr Asp Leu Val Ser Ile Pro His Gly Pro Asn Val Thr Val Arg
            100                 105                 110

Ala Asn Ile Ala Ala Ile Thr Glu Ser Asp Lys Phe Phe Ile Asn Gly
        115                 120                 125

Ser Asn Trp Glu Gly Ile Leu Gly Leu Ala Tyr Ala Glu Ile Ala Arg
    130                 135                 140

Pro Asp Asp Ser Leu Glu Pro Phe Phe Asp Ser Leu Val Lys Gln Thr
145                 150                 155                 160

His Val Pro Asn Leu Phe Ser Leu Gln Leu Cys Gly Ala Gly Phe Pro
                165                 170                 175

Leu Asn Gln Ser Glu Val Leu Ala Ser Val Gly Gly Ser Met Ile Ile
            180                 185                 190

Gly Gly Ile Asp His Ser Leu Tyr Thr Gly Ser Leu Trp Tyr Thr Pro
        195                 200                 205

Ile Arg Arg Glu Trp Tyr Tyr Glu Val Ile Ile Val Arg Val Glu Ile
    210                 215                 220

Asn Gly Gln Asp Leu Lys Met Asp Cys Lys Glu Tyr Asn Tyr Asp Lys
225                 230                 235                 240

Ser Ile Val Asp Ser Gly Thr Thr Asn Leu Arg Leu Pro Lys Lys Val
                245                 250                 255

Phe Glu Ala Ala Val Lys Ser Ile Lys Ala Ala Ser Ser Thr Glu Lys
            260                 265                 270

Phe Pro Asp Gly Phe Trp Leu Gly Glu Gln Leu Val Cys Trp Gln Ala
        275                 280                 285

Gly Thr Thr Pro Trp Asn Ile Phe Pro Val Ile Ser Leu Tyr Leu Met
    290                 295                 300

Gly Glu Val Thr Asn Gln Ser Phe Arg Ile Thr Ile Leu Pro Gln Gln
305                 310                 315                 320

Tyr Leu Arg Pro Val Glu Asp Val Ala Thr Ser Gln Asp Asp Cys Tyr
                325                 330                 335

Lys Phe Ala Ile Ser Gln Ser Ser Thr Gly Thr Val Met Gly Ala Val
            340                 345                 350

Ile Met Glu Gly Phe Tyr Val Val Phe Asp Arg Ala Arg Lys Arg Ile
        355                 360                 365

Gly Phe Ala Val Ser Ala Cys His Val His Asp Glu Phe Arg Thr Ala
    370                 375                 380

Ala Val Glu Gly Pro Phe Val Thr Leu Asp Met Glu Asp Cys Gly Tyr
385                 390                 395                 400

Asn Ile Pro Gln Thr Asp Glu
                405

<210> SEQ ID NO 59
<211> LENGTH: 452
<212> TYPE: PRT
<213> ORGANISM: Homo sapiens

<400> SEQUENCE: 59

Met Ala Gln Ala Leu Pro Trp Leu Leu Leu Trp Met Gly Ala Gly Val
 1               5                  10                  15

Leu Pro Ala His Gly Thr Gln His Gly Ile Arg Leu Pro Leu Arg Ser
            20                  25                  30

Gly Leu Gly Gly Ala Pro Leu Gly Leu Arg Leu Pro Arg Glu Thr Asp
```

```
                35                  40                  45
Glu Glu Pro Glu Pro Gly Arg Arg Gly Ser Phe Val Glu Met Val
 50                  55                  60

Asp Asn Leu Arg Gly Lys Ser Gly Gln Gly Tyr Tyr Val Glu Met Thr
 65                  70                  75                  80

Val Gly Ser Pro Pro Gln Thr Leu Asn Ile Leu Val Asp Thr Gly Ser
                 85                  90                  95

Ser Asn Phe Ala Val Gly Ala Ala Pro His Pro Phe Leu His Arg Tyr
            100                 105                 110

Tyr Gln Arg Gln Leu Ser Ser Thr Tyr Arg Asp Leu Arg Lys Gly Val
        115                 120                 125

Tyr Val Pro Tyr Thr Gln Gly Lys Trp Glu Gly Glu Leu Gly Thr Asp
130                 135                 140

Leu Val Ser Ile Pro His Gly Pro Asn Val Thr Val Arg Ala Asn Ile
145                 150                 155                 160

Ala Ala Ile Thr Glu Ser Asp Lys Phe Phe Ile Asn Gly Ser Asn Trp
                165                 170                 175

Glu Gly Ile Leu Gly Leu Ala Tyr Ala Glu Ile Ala Arg Pro Asp Asp
            180                 185                 190

Ser Leu Glu Pro Phe Phe Asp Ser Leu Val Lys Gln Thr His Val Pro
        195                 200                 205

Asn Leu Phe Ser Leu Gln Leu Cys Gly Ala Gly Phe Pro Leu Asn Gln
210                 215                 220

Ser Glu Val Leu Ala Ser Val Gly Gly Ser Met Ile Ile Gly Gly Ile
225                 230                 235                 240

Asp His Ser Leu Tyr Thr Gly Ser Leu Trp Tyr Thr Pro Ile Arg Arg
                245                 250                 255

Glu Trp Tyr Tyr Glu Val Ile Ile Val Arg Val Glu Ile Asn Gly Gln
            260                 265                 270

Asp Leu Lys Met Asp Cys Lys Glu Tyr Asn Tyr Asp Lys Ser Ile Val
        275                 280                 285

Asp Ser Gly Thr Thr Asn Leu Arg Leu Pro Lys Lys Val Phe Glu Ala
290                 295                 300

Ala Val Lys Ser Ile Lys Ala Ala Ser Ser Thr Glu Lys Phe Pro Asp
305                 310                 315                 320

Gly Phe Trp Leu Gly Glu Gln Leu Val Cys Trp Gln Ala Gly Thr Thr
                325                 330                 335

Pro Trp Asn Ile Phe Pro Val Ile Ser Leu Tyr Leu Met Gly Glu Val
            340                 345                 350

Thr Asn Gln Ser Phe Arg Ile Thr Ile Leu Pro Gln Gln Tyr Leu Arg
        355                 360                 365

Pro Val Glu Asp Val Ala Thr Ser Gln Asp Asp Cys Tyr Lys Phe Ala
370                 375                 380

Ile Ser Gln Ser Ser Thr Gly Thr Val Met Gly Ala Val Ile Met Glu
385                 390                 395                 400

Gly Phe Tyr Val Val Phe Asp Arg Ala Arg Lys Arg Ile Gly Phe Ala
                405                 410                 415

Val Ser Ala Cys His Val His Asp Glu Phe Arg Thr Ala Ala Val Glu
            420                 425                 430

Gly Pro Phe Val Thr Leu Asp Met Glu Asp Cys Gly Tyr Asn Ile Pro
        435                 440                 445

Gln Thr Asp Glu
450
```

<210> SEQ ID NO 60
<211> LENGTH: 420
<212> TYPE: PRT
<213> ORGANISM: Homo sapiens

<400> SEQUENCE: 60

```
Met Ala Gln Ala Leu Pro Trp Leu Leu Leu Trp Met Gly Ala Gly Val
1               5                   10                  15

Leu Pro Ala His Gly Thr Gln His Gly Ile Arg Leu Pro Leu Arg Ser
            20                  25                  30

Gly Leu Gly Gly Ala Pro Leu Gly Leu Arg Leu Pro Arg Glu Thr Asp
        35                  40                  45

Glu Glu Pro Glu Glu Pro Gly Arg Arg Gly Ser Phe Val Glu Met Val
    50                  55                  60

Asp Asn Leu Arg Gly Lys Ser Gly Gln Gly Tyr Tyr Val Glu Met Thr
65                  70                  75                  80

Val Gly Ser Pro Pro Gln Thr Leu Asn Ile Leu Val Asp Thr Gly Ser
                85                  90                  95

Ser Asn Phe Ala Val Gly Ala Ala Pro His Pro Phe Leu His Arg Tyr
            100                 105                 110

Tyr Gln Arg Gln Leu Ser Ser Thr Tyr Arg Asp Leu Arg Lys Gly Val
            115                 120                 125

Tyr Val Pro Tyr Thr Gln Gly Lys Trp Glu Gly Glu Leu Gly Thr Asp
    130                 135                 140

Leu Val Ser Ile Pro His Gly Pro Asn Val Thr Val Arg Ala Asn Ile
145                 150                 155                 160

Ala Ala Ile Thr Glu Ser Asp Lys Phe Phe Ile Asn Gly Ser Asn Trp
                165                 170                 175

Glu Gly Ile Leu Gly Leu Ala Tyr Ala Glu Ile Ala Arg Pro Asp Asp
            180                 185                 190

Ser Leu Glu Pro Phe Phe Asp Ser Leu Val Lys Gln Thr His Val Pro
            195                 200                 205

Asn Leu Phe Ser Leu Gln Leu Cys Gly Ala Gly Phe Pro Leu Asn Gln
    210                 215                 220

Ser Glu Val Leu Ala Ser Val Gly Gly Ser Met Ile Ile Gly Gly Ile
225                 230                 235                 240

Asp His Ser Leu Tyr Thr Gly Ser Leu Trp Tyr Thr Pro Ile Arg Arg
                245                 250                 255

Glu Trp Tyr Tyr Glu Val Ile Ile Val Arg Val Glu Ile Asn Gly Gln
            260                 265                 270

Asp Leu Lys Met Asp Cys Lys Glu Tyr Asn Tyr Asp Lys Ser Ile Val
            275                 280                 285

Asp Ser Gly Thr Thr Asn Leu Arg Leu Pro Lys Lys Val Phe Glu Ala
    290                 295                 300

Ala Val Lys Ser Ile Lys Ala Ala Ser Ser Thr Glu Lys Phe Pro Asp
305                 310                 315                 320

Gly Phe Trp Leu Gly Glu Gln Leu Val Cys Trp Gln Ala Gly Thr Thr
                325                 330                 335

Pro Trp Asn Ile Phe Pro Val Ile Ser Leu Tyr Leu Met Gly Glu Val
            340                 345                 350

Thr Asn Gln Ser Phe Arg Ile Thr Ile Leu Pro Gln Gln Tyr Leu Arg
            355                 360                 365

Pro Val Glu Asp Val Ala Thr Ser Gln Asp Asp Cys Tyr Lys Phe Ala
```

```
            370                 375                 380
Ile Ser Gln Ser Ser Thr Gly Thr Val Met Gly Ala Val Ile Met Glu
385                 390                 395                 400

Gly Phe Tyr Val Val Phe Asp Arg Ala Arg Lys Arg Ile Gly Phe Ala
                405                 410                 415

Val Ser Ala Cys
            420

<210> SEQ ID NO 61
<211> LENGTH: 7
<212> TYPE: PRT
<213> ORGANISM: Artificial Sequence
<220> FEATURE:
<223> OTHER INFORMATION: Synthetic peptide inhibitor
<220> FEATURE:
<221> NAME/KEY: MOD_RES
<222> LOCATION: 4
<223> OTHER INFORMATION: Xaa = hydroxyethlene

<400> SEQUENCE: 61

Glu Val Met Xaa Ala Glu Phe
1               5

<210> SEQ ID NO 62
<211> LENGTH: 26
<212> TYPE: PRT
<213> ORGANISM: Homo sapiens

<400> SEQUENCE: 62

Leu Met Thr Ile Ala Tyr Val Met Ala Ala Ile Cys Ala Leu Phe Met
1               5                   10                  15

Leu Pro Leu Cys Leu Met Val Cys Gln Trp
            20                  25

<210> SEQ ID NO 63
<211> LENGTH: 33
<212> TYPE: PRT
<213> ORGANISM: Homo sapiens
<220> FEATURE:
<223> OTHER INFORMATION: P26-P4'sw peptide substrate

<400> SEQUENCE: 63

Cys Gly Gly Ala Asp Arg Gly Leu Thr Thr Arg Pro Gly Ser Gly Leu
1               5                   10                  15

Thr Asn Ile Lys Thr Glu Glu Ile Ser Glu Val Asn Leu Asp Ala Glu
            20                  25                  30

Phe

<210> SEQ ID NO 64
<211> LENGTH: 29
<212> TYPE: PRT
<213> ORGANISM: Homo sapiens
<220> FEATURE:
<223> OTHER INFORMATION: P26-P1' peptide substrate with CGG linker

<400> SEQUENCE: 64

Cys Gly Gly Ala Asp Arg Gly Leu Thr Thr Arg Pro Gly Ser Gly Leu
1               5                   10                  15

Thr Asn Ile Lys Thr Glu Glu Ile Ser Glu Val Asn Leu
            20                  25

<210> SEQ ID NO 65
<211> LENGTH: 501
```

<212> TYPE: PRT
<213> ORGANISM: Mus musculus

<400> SEQUENCE: 65

```
Met Ala Pro Ala Leu His Trp Leu Leu Leu Trp Val Gly Ser Gly Met
 1               5                  10                  15

Leu Pro Ala Gln Gly Thr His Leu Gly Ile Arg Leu Pro Leu Arg Ser
            20                  25                  30

Gly Leu Ala Gly Pro Pro Leu Gly Leu Arg Leu Pro Arg Glu Thr Asp
        35                  40                  45

Glu Glu Ser Glu Pro Gly Arg Arg Gly Ser Phe Val Glu Met Val
50                  55                  60

Asp Asn Leu Arg Gly Lys Ser Gly Gln Gly Tyr Tyr Val Glu Met Thr
65                  70                  75                  80

Val Gly Ser Pro Pro Gln Thr Leu Asn Ile Leu Val Asp Thr Gly Ser
                85                  90                  95

Ser Asn Phe Ala Val Gly Ala Ala Pro His Pro Phe Leu His Arg Tyr
            100                 105                 110

Tyr Gln Arg Gln Leu Ser Ser Thr Tyr Arg Asp Leu Arg Lys Gly Val
        115                 120                 125

Tyr Val Pro Tyr Thr Gln Gly Lys Trp Glu Gly Glu Leu Gly Thr Asp
130                 135                 140

Leu Val Ser Ile Pro His Gly Pro Asn Val Thr Val Arg Ala Asn Ile
145                 150                 155                 160

Ala Ala Ile Thr Glu Ser Asp Lys Phe Phe Ile Asn Gly Ser Asn Trp
                165                 170                 175

Glu Gly Ile Leu Gly Leu Ala Tyr Ala Glu Ile Ala Arg Pro Asp Asp
            180                 185                 190

Ser Leu Glu Pro Phe Phe Asp Ser Leu Val Lys Gln Thr His Ile Pro
        195                 200                 205

Asn Ile Phe Ser Leu Gln Leu Cys Gly Ala Gly Phe Pro Leu Asn Gln
210                 215                 220

Thr Glu Ala Leu Ala Ser Val Gly Gly Ser Met Ile Ile Gly Gly Ile
225                 230                 235                 240

Asp His Ser Leu Tyr Thr Gly Ser Leu Trp Tyr Thr Pro Ile Arg Arg
                245                 250                 255

Glu Trp Tyr Tyr Glu Val Ile Ile Val Arg Val Glu Ile Asn Gly Gln
            260                 265                 270

Asp Leu Lys Met Asp Cys Lys Glu Tyr Asn Tyr Asp Lys Ser Ile Val
        275                 280                 285

Asp Ser Gly Thr Thr Asn Leu Arg Leu Pro Lys Lys Val Phe Glu Ala
290                 295                 300

Ala Val Lys Ser Ile Lys Ala Ala Ser Ser Thr Glu Lys Phe Pro Asp
305                 310                 315                 320

Gly Phe Trp Leu Gly Glu Gln Leu Val Cys Trp Gln Ala Gly Thr Thr
                325                 330                 335

Pro Trp Asn Ile Phe Pro Val Ile Ser Leu Tyr Leu Met Gly Glu Val
            340                 345                 350

Thr Asn Gln Ser Phe Arg Ile Thr Ile Leu Pro Gln Gln Tyr Leu Arg
        355                 360                 365

Pro Val Glu Asp Val Ala Thr Ser Gln Asp Asp Cys Tyr Lys Phe Ala
370                 375                 380

Val Ser Gln Ser Ser Thr Gly Thr Val Met Gly Ala Val Ile Met Glu
385                 390                 395                 400
```

```
Gly Phe Tyr Val Val Phe Asp Arg Ala Arg Lys Arg Ile Gly Phe Ala
                405                 410                 415
Val Ser Ala Cys His Val His Asp Glu Phe Arg Thr Ala Ala Val Glu
            420                 425                 430
Gly Pro Phe Val Thr Ala Asp Met Glu Asp Cys Gly Tyr Asn Ile Pro
        435                 440                 445
Gln Thr Asp Glu Ser Thr Leu Met Thr Ile Ala Tyr Val Met Ala Ala
450                 455                 460
Ile Cys Ala Leu Phe Met Leu Pro Leu Cys Leu Met Val Cys Gln Trp
465                 470                 475                 480
Arg Cys Leu Arg Cys Leu Arg His Gln His Asp Asp Phe Gly Asp Asp
                485                 490                 495
Ile Ser Leu Leu Lys
                500

<210> SEQ ID NO 66
<211> LENGTH: 480
<212> TYPE: PRT
<213> ORGANISM: Homo sapiens

<400> SEQUENCE: 66

Thr Gln His Gly Ile Arg Leu Pro Leu Arg Ser Gly Leu Gly Gly Ala
1               5                   10                  15
Pro Leu Gly Leu Arg Leu Pro Arg Glu Thr Asp Glu Glu Pro Glu Glu
            20                  25                  30
Pro Gly Arg Arg Gly Ser Phe Val Glu Met Val Asp Asn Leu Arg Gly
        35                  40                  45
Lys Ser Gly Gln Gly Tyr Tyr Val Glu Met Thr Val Gly Ser Pro Pro
    50                  55                  60
Gln Thr Leu Asn Ile Leu Val Asp Thr Gly Ser Ser Asn Phe Ala Val
65                  70                  75                  80
Gly Ala Ala Pro His Pro Phe Leu His Arg Tyr Tyr Gln Arg Gln Leu
                85                  90                  95
Ser Ser Thr Tyr Arg Asp Leu Arg Lys Gly Val Tyr Val Pro Tyr Thr
            100                 105                 110
Gln Gly Lys Trp Glu Gly Glu Leu Gly Thr Asp Leu Val Ser Ile Pro
        115                 120                 125
His Gly Pro Asn Val Thr Val Arg Ala Asn Ile Ala Ala Ile Thr Glu
    130                 135                 140
Ser Asp Lys Phe Phe Ile Asn Gly Ser Asn Trp Glu Gly Ile Leu Gly
145                 150                 155                 160
Leu Ala Tyr Ala Glu Ile Ala Arg Pro Asp Asp Ser Leu Glu Pro Phe
                165                 170                 175
Phe Asp Ser Leu Val Lys Gln Thr His Val Pro Asn Leu Phe Ser Leu
            180                 185                 190
Gln Leu Cys Gly Ala Gly Phe Pro Leu Asn Gln Ser Glu Val Leu Ala
        195                 200                 205
Ser Val Gly Gly Ser Met Ile Ile Gly Gly Ile Asp His Ser Leu Tyr
    210                 215                 220
Thr Gly Ser Leu Trp Tyr Thr Pro Ile Arg Arg Glu Trp Tyr Tyr Glu
225                 230                 235                 240
Val Ile Ile Val Arg Val Glu Ile Asn Gly Gln Asp Leu Lys Met Asp
                245                 250                 255
Cys Lys Glu Tyr Asn Tyr Asp Lys Ser Ile Val Asp Ser Gly Thr Thr
```

-continued

```
                260                 265                 270
Asn Leu Arg Leu Pro Lys Lys Val Phe Glu Ala Ala Val Lys Ser Ile
            275                 280                 285
Lys Ala Ala Ser Ser Thr Glu Lys Phe Pro Asp Gly Phe Trp Leu Gly
        290                 295                 300
Glu Gln Leu Val Cys Trp Gln Ala Gly Thr Thr Pro Trp Asn Ile Phe
305                 310                 315                 320
Pro Val Ile Ser Leu Tyr Leu Met Gly Glu Val Thr Asn Gln Ser Phe
                325                 330                 335
Arg Ile Thr Ile Leu Pro Gln Gln Tyr Leu Arg Pro Val Glu Asp Val
            340                 345                 350
Ala Thr Ser Gln Asp Asp Cys Tyr Lys Phe Ala Ile Ser Gln Ser Ser
        355                 360                 365
Thr Gly Thr Val Met Gly Ala Val Ile Met Glu Gly Phe Tyr Val Val
370                 375                 380
Phe Asp Arg Ala Arg Lys Arg Ile Gly Phe Ala Val Ser Ala Cys His
                385                 390                 395                 400
Val His Asp Glu Phe Arg Thr Ala Ala Val Glu Gly Pro Phe Val Thr
            405                 410                 415
Leu Asp Met Glu Asp Cys Gly Tyr Asn Ile Pro Gln Thr Asp Glu Ser
        420                 425                 430
Thr Leu Met Thr Ile Ala Tyr Val Met Ala Ala Ile Cys Ala Leu Phe
    435                 440                 445
Met Leu Pro Leu Cys Leu Met Val Cys Gln Trp Arg Cys Leu Arg Cys
450                 455                 460
Leu Arg Gln Gln His Asp Asp Phe Ala Asp Asp Ile Ser Leu Leu Lys
465                 470                 475                 480

<210> SEQ ID NO 67
<211> LENGTH: 444
<212> TYPE: PRT
<213> ORGANISM: Homo sapiens

<400> SEQUENCE: 67

Gly Ser Phe Val Glu Met Val Asp Asn Leu Arg Gly Lys Ser Gly Gln
1               5                   10                  15
Gly Tyr Tyr Val Glu Met Thr Val Gly Ser Pro Pro Gln Thr Leu Asn
            20                  25                  30
Ile Leu Val Asp Thr Gly Ser Ser Asn Phe Ala Val Gly Ala Ala Pro
        35                  40                  45
His Pro Phe Leu His Arg Tyr Tyr Gln Arg Gln Leu Ser Ser Thr Tyr
    50                  55                  60
Arg Asp Leu Arg Lys Gly Val Tyr Val Pro Tyr Thr Gln Gly Lys Trp
65                  70                  75                  80
Glu Gly Glu Leu Gly Thr Asp Leu Val Ser Ile Pro His Gly Pro Asn
                85                  90                  95
Val Thr Val Arg Ala Asn Ile Ala Ala Ile Thr Glu Ser Asp Lys Phe
            100                 105                 110
Phe Ile Asn Gly Ser Asn Trp Glu Gly Ile Leu Gly Leu Ala Tyr Ala
        115                 120                 125
Glu Ile Ala Arg Pro Asp Asp Ser Leu Glu Pro Phe Phe Asp Ser Leu
    130                 135                 140
Val Lys Gln Thr His Val Pro Asn Leu Phe Ser Leu Gln Leu Cys Gly
145                 150                 155                 160
```

```
Ala Gly Phe Pro Leu Asn Gln Ser Glu Val Leu Ala Ser Val Gly Gly
            165                 170                 175

Ser Met Ile Ile Gly Gly Ile Asp His Ser Leu Tyr Thr Gly Ser Leu
            180                 185                 190

Trp Tyr Thr Pro Ile Arg Arg Glu Trp Tyr Tyr Glu Val Ile Ile Val
            195                 200                 205

Arg Val Glu Ile Asn Gly Gln Asp Leu Lys Met Asp Cys Lys Glu Tyr
    210                 215                 220

Asn Tyr Asp Lys Ser Ile Val Asp Ser Gly Thr Thr Asn Leu Arg Leu
225                 230                 235                 240

Pro Lys Lys Val Phe Glu Ala Ala Val Lys Ser Ile Lys Ala Ala Ser
                245                 250                 255

Ser Thr Glu Lys Phe Pro Asp Gly Phe Trp Leu Gly Glu Gln Leu Val
            260                 265                 270

Cys Trp Gln Ala Gly Thr Thr Pro Trp Asn Ile Phe Pro Val Ile Ser
            275                 280                 285

Leu Tyr Leu Met Gly Glu Val Thr Asn Gln Ser Phe Arg Ile Thr Ile
            290                 295                 300

Leu Pro Gln Gln Tyr Leu Arg Pro Val Glu Asp Val Ala Thr Ser Gln
305                 310                 315                 320

Asp Asp Cys Tyr Lys Phe Ala Ile Ser Gln Ser Ser Thr Gly Thr Val
                325                 330                 335

Met Gly Ala Val Ile Met Glu Gly Phe Tyr Val Val Phe Asp Arg Ala
            340                 345                 350

Arg Lys Arg Ile Gly Phe Ala Val Ser Ala Cys His Val His Asp Glu
            355                 360                 365

Phe Arg Thr Ala Ala Val Glu Gly Pro Phe Val Thr Leu Asp Met Glu
            370                 375                 380

Asp Cys Gly Tyr Asn Ile Pro Gln Thr Asp Glu Ser Thr Leu Met Thr
385                 390                 395                 400

Ile Ala Tyr Val Met Ala Ala Ile Cys Ala Leu Phe Met Leu Pro Leu
                405                 410                 415

Cys Leu Met Val Cys Gln Trp Arg Cys Leu Arg Cys Leu Arg Gln Gln
            420                 425                 430

His Asp Asp Phe Ala Asp Asp Ile Ser Leu Leu Lys
            435                 440

<210> SEQ ID NO 68
<211> LENGTH: 395
<212> TYPE: PRT
<213> ORGANISM: Homo sapiens

<400> SEQUENCE: 68

Gly Ser Phe Val Glu Met Val Asp Asn Leu Arg Gly Lys Ser Gly Gln
1               5                   10                  15

Gly Tyr Tyr Val Glu Met Thr Val Gly Ser Pro Pro Gln Thr Leu Asn
            20                  25                  30

Ile Leu Val Asp Thr Gly Ser Ser Asn Phe Ala Val Gly Ala Ala Pro
            35                  40                  45

His Pro Phe Leu His Arg Tyr Tyr Gln Arg Gln Leu Ser Ser Thr Tyr
        50                  55                  60

Arg Asp Leu Arg Lys Gly Val Tyr Val Pro Tyr Thr Gln Gly Lys Trp
65                  70                  75                  80

Glu Gly Glu Leu Gly Thr Asp Leu Val Ser Ile Pro His Gly Pro Asn
                85                  90                  95
```

```
Val Thr Val Arg Ala Asn Ile Ala Ala Ile Thr Glu Ser Asp Lys Phe
            100                 105                 110

Phe Ile Asn Gly Ser Asn Trp Glu Gly Ile Leu Gly Leu Ala Tyr Ala
            115                 120                 125

Glu Ile Ala Arg Pro Asp Asp Ser Leu Glu Pro Phe Phe Asp Ser Leu
            130                 135                 140

Val Lys Gln Thr His Val Pro Asn Leu Phe Ser Leu Gln Leu Cys Gly
145                 150                 155                 160

Ala Gly Phe Pro Leu Asn Gln Ser Glu Val Leu Ala Ser Val Gly Gly
                165                 170                 175

Ser Met Ile Ile Gly Gly Ile Asp His Ser Leu Tyr Thr Gly Ser Leu
                180                 185                 190

Trp Tyr Thr Pro Ile Arg Arg Glu Trp Tyr Tyr Glu Val Ile Ile Val
            195                 200                 205

Arg Val Glu Ile Asn Gly Gln Asp Leu Lys Met Asp Cys Lys Glu Tyr
            210                 215                 220

Asn Tyr Asp Lys Ser Ile Val Asp Ser Gly Thr Thr Asn Leu Arg Leu
225                 230                 235                 240

Pro Lys Lys Val Phe Glu Ala Ala Val Lys Ser Ile Lys Ala Ala Ser
                245                 250                 255

Ser Thr Glu Lys Phe Pro Asp Gly Phe Trp Leu Gly Glu Gln Leu Val
                260                 265                 270

Cys Trp Gln Ala Gly Thr Thr Pro Trp Asn Ile Phe Pro Val Ile Ser
            275                 280                 285

Leu Tyr Leu Met Gly Glu Val Thr Asn Gln Ser Phe Arg Ile Thr Ile
290                 295                 300

Leu Pro Gln Gln Tyr Leu Arg Pro Val Glu Asp Val Ala Thr Ser Gln
305                 310                 315                 320

Asp Asp Cys Tyr Lys Phe Ala Ile Ser Gln Ser Ser Thr Gly Thr Val
                325                 330                 335

Met Gly Ala Val Ile Met Glu Gly Phe Tyr Val Val Phe Asp Arg Ala
            340                 345                 350

Arg Lys Arg Ile Gly Phe Ala Val Ser Ala Cys His Val His Asp Glu
            355                 360                 365

Phe Arg Thr Ala Ala Val Glu Gly Pro Phe Val Thr Leu Asp Met Glu
            370                 375                 380

Asp Cys Gly Tyr Asn Ile Pro Gln Thr Asp Glu
385                 390                 395

<210> SEQ ID NO 69
<211> LENGTH: 439
<212> TYPE: PRT
<213> ORGANISM: Homo sapiens

<400> SEQUENCE: 69

Met Val Asp Asn Leu Arg Gly Lys Ser Gly Gln Gly Tyr Tyr Val Glu
  1               5                  10                  15

Met Thr Val Gly Ser Pro Pro Gln Thr Leu Asn Ile Leu Val Asp Thr
             20                  25                  30

Gly Ser Ser Asn Phe Ala Val Gly Ala Ala Pro His Pro Phe Leu His
             35                  40                  45

Arg Tyr Tyr Gln Arg Gln Leu Ser Ser Thr Tyr Arg Asp Leu Arg Lys
         50                  55                  60

Gly Val Tyr Val Pro Tyr Thr Gln Gly Lys Trp Glu Gly Glu Leu Gly
```

```
                65                  70                  75                  80
Thr Asp Leu Val Ser Ile Pro His Gly Pro Asn Val Thr Val Arg Ala
                    85                  90                  95
Asn Ile Ala Ala Ile Thr Glu Ser Asp Lys Phe Phe Ile Asn Gly Ser
                100                 105                 110
Asn Trp Glu Gly Ile Leu Gly Leu Ala Tyr Ala Glu Ile Ala Arg Pro
            115                 120                 125
Asp Asp Ser Leu Glu Pro Phe Phe Asp Ser Leu Val Lys Gln Thr His
        130                 135                 140
Val Pro Asn Leu Phe Ser Leu Gln Leu Cys Gly Ala Gly Phe Pro Leu
145                 150                 155                 160
Asn Gln Ser Glu Val Leu Ala Ser Val Gly Gly Ser Met Ile Ile Gly
                165                 170                 175
Gly Ile Asp His Ser Leu Tyr Thr Gly Ser Leu Trp Tyr Thr Pro Ile
            180                 185                 190
Arg Arg Glu Trp Tyr Tyr Glu Val Ile Ile Val Arg Val Glu Ile Asn
        195                 200                 205
Gly Gln Asp Leu Lys Met Asp Cys Lys Glu Tyr Asn Tyr Asp Lys Ser
    210                 215                 220
Ile Val Asp Ser Gly Thr Thr Asn Leu Arg Leu Pro Lys Lys Val Phe
225                 230                 235                 240
Glu Ala Ala Val Lys Ser Ile Lys Ala Ala Ser Ser Thr Glu Lys Phe
                245                 250                 255
Pro Asp Gly Phe Trp Leu Gly Glu Gln Leu Val Cys Trp Gln Ala Gly
            260                 265                 270
Thr Thr Pro Trp Asn Ile Phe Pro Val Ile Ser Leu Tyr Leu Met Gly
        275                 280                 285
Glu Val Thr Asn Gln Ser Phe Arg Ile Thr Ile Leu Pro Gln Gln Tyr
    290                 295                 300
Leu Arg Pro Val Glu Asp Val Ala Thr Ser Gln Asp Asp Cys Tyr Lys
305                 310                 315                 320
Phe Ala Ile Ser Gln Ser Ser Thr Gly Thr Val Met Gly Ala Val Ile
                325                 330                 335
Met Glu Gly Phe Tyr Val Val Phe Asp Arg Ala Arg Lys Arg Ile Gly
            340                 345                 350
Phe Ala Val Ser Ala Cys His Val His Asp Glu Phe Arg Thr Ala Ala
        355                 360                 365
Val Glu Gly Pro Phe Val Thr Leu Asp Met Glu Asp Cys Gly Tyr Asn
    370                 375                 380
Ile Pro Gln Thr Asp Glu Ser Thr Leu Met Thr Ile Ala Tyr Val Met
385                 390                 395                 400
Ala Ala Ile Cys Ala Leu Phe Met Leu Pro Leu Cys Leu Met Val Cys
                405                 410                 415
Gln Trp Arg Cys Leu Arg Cys Leu Arg Gln Gln His Asp Asp Phe Ala
            420                 425                 430
Asp Asp Ile Ser Leu Leu Lys
        435

<210> SEQ ID NO 70
<211> LENGTH: 390
<212> TYPE: PRT
<213> ORGANISM: Homo sapiens

<400> SEQUENCE: 70
```

```
Met Val Asp Asn Leu Arg Gly Lys Ser Gly Gln Gly Tyr Tyr Val Glu
 1               5                  10                  15

Met Thr Val Gly Ser Pro Pro Gln Thr Leu Asn Ile Leu Val Asp Thr
                20                  25                  30

Gly Ser Ser Asn Phe Ala Val Gly Ala Ala Pro His Pro Phe Leu His
             35                  40                  45

Arg Tyr Tyr Gln Arg Gln Leu Ser Ser Thr Tyr Arg Asp Leu Arg Lys
         50                  55                  60

Gly Val Tyr Val Pro Tyr Thr Gln Gly Lys Trp Glu Gly Glu Leu Gly
 65                  70                  75                  80

Thr Asp Leu Val Ser Ile Pro His Gly Pro Asn Val Thr Val Arg Ala
                 85                  90                  95

Asn Ile Ala Ala Ile Thr Glu Ser Asp Lys Phe Phe Ile Asn Gly Ser
             100                 105                 110

Asn Trp Glu Gly Ile Leu Gly Leu Ala Tyr Ala Glu Ile Ala Arg Pro
         115                 120                 125

Asp Asp Ser Leu Glu Pro Phe Phe Asp Ser Leu Val Lys Gln Thr His
         130                 135                 140

Val Pro Asn Leu Phe Ser Leu Gln Leu Cys Gly Ala Gly Phe Pro Leu
145                 150                 155                 160

Asn Gln Ser Glu Val Leu Ala Ser Val Gly Gly Ser Met Ile Ile Gly
                165                 170                 175

Gly Ile Asp His Ser Leu Tyr Thr Gly Ser Leu Trp Tyr Thr Pro Ile
             180                 185                 190

Arg Arg Glu Trp Tyr Tyr Glu Val Ile Ile Val Arg Val Glu Ile Asn
         195                 200                 205

Gly Gln Asp Leu Lys Met Asp Cys Lys Glu Tyr Asn Tyr Asp Lys Ser
         210                 215                 220

Ile Val Asp Ser Gly Thr Thr Asn Leu Arg Leu Pro Lys Lys Val Phe
225                 230                 235                 240

Glu Ala Ala Val Lys Ser Ile Lys Ala Ala Ser Ser Thr Glu Lys Phe
                245                 250                 255

Pro Asp Gly Phe Trp Leu Gly Glu Gln Leu Val Cys Trp Gln Ala Gly
             260                 265                 270

Thr Thr Pro Trp Asn Ile Phe Pro Val Ile Ser Leu Tyr Leu Met Gly
         275                 280                 285

Glu Val Thr Asn Gln Ser Phe Arg Ile Thr Ile Leu Pro Gln Gln Tyr
         290                 295                 300

Leu Arg Pro Val Glu Asp Val Ala Thr Ser Gln Asp Asp Cys Tyr Lys
305                 310                 315                 320

Phe Ala Ile Ser Gln Ser Ser Thr Gly Thr Val Met Gly Ala Val Ile
                325                 330                 335

Met Glu Gly Phe Tyr Val Val Phe Asp Arg Ala Arg Lys Arg Ile Gly
             340                 345                 350

Phe Ala Val Ser Ala Cys His Val His Asp Glu Phe Arg Thr Ala Ala
         355                 360                 365

Val Glu Gly Pro Phe Val Thr Leu Asp Met Glu Asp Cys Gly Tyr Asn
         370                 375                 380

Ile Pro Gln Thr Asp Glu
385                 390

<210> SEQ ID NO 71
<211> LENGTH: 374
<212> TYPE: PRT
```

<213> ORGANISM: Homo sapiens

<400> SEQUENCE: 71

```
Glu Thr Asp Glu Glu Pro Glu Pro Gly Arg Arg Gly Ser Phe Val
1               5                   10                  15
Glu Met Val Asp Asn Leu Arg Gly Lys Ser Gly Gln Gly Tyr Tyr Val
            20                  25                  30
Glu Met Thr Val Gly Ser Pro Pro Gln Thr Leu Asn Ile Leu Val Asp
        35                  40                  45
Thr Gly Ser Ser Asn Phe Ala Val Gly Ala Ala Pro His Pro Phe Leu
    50                  55                  60
His Arg Tyr Tyr Gln Arg Gln Leu Ser Ser Thr Tyr Arg Asp Leu Arg
65              70                  75                  80
Lys Gly Val Tyr Val Pro Tyr Thr Gln Gly Lys Trp Glu Gly Glu Leu
                85                  90                  95
Gly Thr Asp Leu Val Ser Ile Pro His Gly Pro Asn Val Thr Val Arg
            100                 105                 110
Ala Asn Ile Ala Ala Ile Thr Glu Ser Asp Lys Phe Phe Ile Asn Gly
        115                 120                 125
Ser Asn Trp Glu Gly Ile Leu Gly Leu Ala Tyr Ala Glu Ile Ala Arg
    130                 135                 140
Pro Asp Asp Ser Leu Glu Pro Phe Phe Asp Ser Leu Val Lys Gln Thr
145                 150                 155                 160
His Val Pro Asn Leu Phe Ser Leu Gln Leu Cys Gly Ala Gly Phe Pro
                165                 170                 175
Leu Asn Gln Ser Glu Val Leu Ala Ser Val Gly Gly Ser Met Ile Ile
            180                 185                 190
Gly Gly Ile Asp His Ser Leu Tyr Thr Gly Ser Leu Trp Tyr Thr Pro
        195                 200                 205
Ile Arg Arg Glu Trp Tyr Tyr Glu Val Ile Ile Val Arg Val Glu Ile
    210                 215                 220
Asn Gly Gln Asp Leu Lys Met Asp Cys Lys Glu Tyr Asn Tyr Asp Lys
225                 230                 235                 240
Ser Ile Val Asp Ser Gly Thr Thr Asn Leu Arg Leu Pro Lys Lys Val
                245                 250                 255
Phe Glu Ala Ala Val Lys Ser Ile Lys Ala Ala Ser Ser Thr Glu Lys
            260                 265                 270
Phe Pro Asp Gly Phe Trp Leu Gly Glu Gln Leu Val Cys Trp Gln Ala
        275                 280                 285
Gly Thr Thr Pro Trp Asn Ile Phe Pro Val Ile Ser Leu Tyr Leu Met
    290                 295                 300
Gly Glu Val Thr Asn Gln Ser Phe Arg Ile Thr Ile Leu Pro Gln Gln
305                 310                 315                 320
Tyr Leu Arg Pro Val Glu Asp Val Ala Thr Ser Gln Asp Asp Cys Tyr
                325                 330                 335
Lys Phe Ala Ile Ser Gln Ser Ser Thr Gly Thr Val Met Gly Ala Val
            340                 345                 350
Ile Met Glu Gly Phe Tyr Val Val Phe Asp Arg Ala Arg Lys Arg Ile
        355                 360                 365
Gly Phe Ala Val Ser Ala
    370
```

<210> SEQ ID NO 72
<211> LENGTH: 14

```
<212> TYPE: PRT
<213> ORGANISM: Artificial Sequence
<220> FEATURE:
<223> OTHER INFORMATION: P10-P4'staD-V peptide inhibitor
<220> FEATURE:
<221> NAME/KEY: MOD_RES
<222> LOCATION: 10
<223> OTHER INFORMATION: Xaa is statine moiety

<400> SEQUENCE: 72

Lys Thr Glu Glu Ile Ser Glu Val Asn Xaa Val Ala Glu Phe
 1               5                  10

<210> SEQ ID NO 73
<211> LENGTH: 9
<212> TYPE: PRT
<213> ORGANISM: Artificial Sequence
<220> FEATURE:
<223> OTHER INFORMATION: P4-P4'staD-V peptide inhibitor
<220> FEATURE:
<221> NAME/KEY: MOD_RES
<222> LOCATION: 5
<223> OTHER INFORMATION: Xaa is statine moiety

<400> SEQUENCE: 73

Ser Glu Val Asn Xaa Val Ala Glu Phe
 1               5

<210> SEQ ID NO 74
<211> LENGTH: 431
<212> TYPE: PRT
<213> ORGANISM: Homo sapiens

<400> SEQUENCE: 74

Thr Gln His Gly Ile Arg Leu Pro Leu Arg Ser Gly Leu Gly Gly Ala
 1               5                  10                  15

Pro Leu Gly Leu Arg Leu Pro Arg Glu Thr Asp Glu Glu Pro Glu Glu
                20                  25                  30

Pro Gly Arg Arg Gly Ser Phe Val Glu Met Val Asp Asn Leu Arg Gly
            35                  40                  45

Lys Ser Gly Gln Gly Tyr Tyr Val Glu Met Thr Val Gly Ser Pro Pro
 50                  55                  60

Gln Thr Leu Asn Ile Leu Val Asp Thr Gly Ser Ser Asn Phe Ala Val
65                  70                  75                  80

Gly Ala Ala Pro His Pro Phe Leu His Arg Tyr Tyr Gln Arg Gln Leu
                85                  90                  95

Ser Ser Thr Tyr Arg Asp Leu Arg Lys Gly Val Tyr Val Pro Tyr Thr
            100                 105                 110

Gln Gly Lys Trp Glu Gly Glu Leu Gly Thr Asp Leu Val Ser Ile Pro
        115                 120                 125

His Gly Pro Asn Val Thr Val Arg Ala Asn Ile Ala Ala Ile Thr Glu
130                 135                 140

Ser Asp Lys Phe Phe Ile Asn Gly Ser Asn Trp Glu Gly Ile Leu Gly
145                 150                 155                 160

Leu Ala Tyr Ala Glu Ile Ala Arg Pro Asp Asp Ser Leu Glu Pro Phe
                165                 170                 175

Phe Asp Ser Leu Val Lys Gln Thr His Val Pro Asn Leu Phe Ser Leu
            180                 185                 190

Gln Leu Cys Gly Ala Gly Phe Pro Leu Asn Gln Ser Glu Val Leu Ala
        195                 200                 205

Ser Val Gly Gly Ser Met Ile Ile Gly Gly Ile Asp His Ser Leu Tyr
```

```
            210                 215                 220
Thr Gly Ser Leu Trp Tyr Thr Pro Ile Arg Arg Glu Trp Tyr Tyr Glu
225                 230                 235                 240

Val Ile Ile Val Arg Val Glu Ile Asn Gly Gln Asp Leu Lys Met Asp
                245                 250                 255

Cys Lys Glu Tyr Asn Tyr Asp Lys Ser Ile Val Asp Ser Gly Thr Thr
            260                 265                 270

Asn Leu Arg Leu Pro Lys Lys Val Phe Glu Ala Ala Val Lys Ser Ile
        275                 280                 285

Lys Ala Ala Ser Ser Thr Glu Lys Phe Pro Asp Gly Phe Trp Leu Gly
290                 295                 300

Glu Gln Leu Val Cys Trp Gln Ala Gly Thr Thr Pro Trp Asn Ile Phe
305                 310                 315                 320

Pro Val Ile Ser Leu Tyr Leu Met Gly Glu Val Thr Asn Gln Ser Phe
                325                 330                 335

Arg Ile Thr Ile Leu Pro Gln Gln Tyr Leu Arg Pro Val Glu Asp Val
            340                 345                 350

Ala Thr Ser Gln Asp Asp Cys Tyr Lys Phe Ala Ile Ser Gln Ser Ser
        355                 360                 365

Thr Gly Thr Val Met Gly Ala Val Ile Met Glu Gly Phe Tyr Val Val
370                 375                 380

Phe Asp Arg Ala Arg Lys Arg Ile Gly Phe Ala Val Ser Ala Cys His
385                 390                 395                 400

Val His Asp Glu Phe Arg Thr Ala Ala Val Glu Gly Pro Phe Val Thr
                405                 410                 415

Leu Asp Met Glu Asp Cys Gly Tyr Asn Ile Pro Gln Thr Asp Glu
            420                 425                 430

<210> SEQ ID NO 75
<211> LENGTH: 361
<212> TYPE: PRT
<213> ORGANISM: Homo sapiens

<400> SEQUENCE: 75

Met Val Asp Asn Leu Arg Gly Lys Ser Gly Gln Gly Tyr Tyr Val Glu
1               5                   10                  15

Met Thr Val Gly Ser Pro Pro Gln Thr Leu Asn Ile Leu Val Asp Thr
            20                  25                  30

Gly Ser Ser Asn Phe Ala Val Gly Ala Ala Pro His Pro Phe Leu His
        35                  40                  45

Arg Tyr Tyr Gln Arg Gln Leu Ser Ser Thr Tyr Arg Asp Leu Arg Lys
    50                  55                  60

Gly Val Tyr Val Pro Tyr Thr Gln Gly Lys Trp Glu Gly Glu Leu Gly
65                  70                  75                  80

Thr Asp Leu Val Ser Ile Pro His Gly Pro Asn Val Thr Val Arg Ala
                85                  90                  95

Asn Ile Ala Ala Ile Thr Glu Ser Asp Lys Phe Phe Ile Asn Gly Ser
            100                 105                 110

Asn Trp Glu Gly Ile Leu Gly Leu Ala Tyr Ala Glu Ile Ala Arg Pro
        115                 120                 125

Asp Asp Ser Leu Glu Pro Phe Phe Asp Ser Leu Val Lys Gln Thr His
    130                 135                 140

Val Pro Asn Leu Phe Ser Leu Gln Leu Cys Gly Ala Gly Phe Pro Leu
145                 150                 155                 160
```

```
Asn Gln Ser Glu Val Leu Ala Ser Val Gly Gly Ser Met Ile Ile Gly
                165                 170                 175

Gly Ile Asp His Ser Leu Tyr Thr Gly Ser Leu Trp Tyr Thr Pro Ile
            180                 185                 190

Arg Arg Glu Trp Tyr Tyr Glu Val Ile Ile Val Arg Val Glu Ile Asn
        195                 200                 205

Gly Gln Asp Leu Lys Met Asp Cys Lys Glu Tyr Asn Tyr Asp Lys Ser
    210                 215                 220

Ile Val Asp Ser Gly Thr Thr Asn Leu Arg Leu Pro Lys Lys Val Phe
225                 230                 235                 240

Glu Ala Ala Val Lys Ser Ile Lys Ala Ala Ser Ser Thr Glu Lys Phe
                245                 250                 255

Pro Asp Gly Phe Trp Leu Gly Glu Gln Leu Val Cys Trp Gln Ala Gly
            260                 265                 270

Thr Thr Pro Trp Asn Ile Phe Pro Val Ile Ser Leu Tyr Leu Met Gly
        275                 280                 285

Glu Val Thr Asn Gln Ser Phe Arg Ile Thr Ile Leu Pro Gln Gln Tyr
    290                 295                 300

Leu Arg Pro Val Glu Asp Val Ala Thr Ser Gln Asp Asp Cys Tyr Lys
305                 310                 315                 320

Phe Ala Ile Ser Gln Ser Ser Thr Gly Thr Val Met Gly Ala Val Ile
                325                 330                 335

Met Glu Gly Phe Tyr Val Val Phe Asp Arg Ala Arg Lys Arg Ile Gly
            340                 345                 350

Phe Ala Val Ser Ala Cys His Val His
            355                 360

<210> SEQ ID NO 76
<211> LENGTH: 63
<212> TYPE: DNA
<213> ORGANISM: Homo sapiens
<220> FEATURE:
<221> NAME/KEY: misc_feature
<222> LOCATION: (1)...(63)
<223> OTHER INFORMATION: n = A,T,C or G

<400> SEQUENCE: 76
garacngayg argarccnga rgarccnggn mgnmgnggnw snttygtnga ratggtngay      60 aay                                                                   63

<210> SEQ ID NO 77
<211> LENGTH: 21
<212> TYPE: PRT
<213> ORGANISM: Homo sapiens

<400> SEQUENCE: 77

Glu Thr Asp Glu Glu Pro Glu Glu Pro Gly Arg Arg Gly Ser Phe Val
1               5                   10                  15

Glu Met Val Asp Asn
            20

<210> SEQ ID NO 78
<211> LENGTH: 7
<212> TYPE: PRT
<213> ORGANISM: Artificial Sequence
<220> FEATURE:
<223> OTHER INFORMATION: Peptide inhibitor P3-P4' XD-V
<220> FEATURE:
<221> NAME/KEY: MOD_RES
<222> LOCATION: 3
```

```
<223> OTHER INFORMATION: Xaa is hydroxyethylene or statine

<400> SEQUENCE: 78

Val Met Xaa Val Ala Glu Phe
 1               5

<210> SEQ ID NO 79
<211> LENGTH: 11
<212> TYPE: PRT
<213> ORGANISM: Homo sapiens

<400> SEQUENCE: 79

Pro Glu Glu Pro Gly Arg Arg Gly Ser Phe Val
 1               5                  10

<210> SEQ ID NO 80
<211> LENGTH: 419
<212> TYPE: DNA
<213> ORGANISM: Artificial Sequence
<220> FEATURE:
<223> OTHER INFORMATION: nucleotide insert in vector pCF

<400> SEQUENCE: 80
ctgttgggct cgcggttgag gacaaactct tcgcggtctt tccagtactc ttggatcgga      60
aacccgtcgg cctccgaacg gtactccgcc accgagggac ctgagcgagt ccgcatcgac     120
cggatcggaa aacctctcga ctgttggggt gagtactccc tctcaaaagc gggcatgact     180
tctgcgctaa gattgtcagt ttccaaaaac gaggaggatt tgatattcac ctggcccgcg     240
gtgatgcctt tgagggtggc cgcgtccatc tggtcagaaa agacaatctt tttgttgtca     300
agcttgaggt gtggcaggct tgagatctgg ccatacactt gagtgacaat gacatccact     360
ttgcctttct ctccacaggt gtccactccc aggtccaact gcaggtcgac tctagaccc     419

<210> SEQ ID NO 81
<211> LENGTH: 8
<212> TYPE: PRT
<213> ORGANISM: Artificial Sequence
<220> FEATURE:
<223> OTHER INFORMATION: Peptide inhibitor P4-P4' XD-V
<220> FEATURE:
<221> NAME/KEY: MOD_RES
<222> LOCATION: 4
<223> OTHER INFORMATION: Xaa is hydroxyethylene or statine

<400> SEQUENCE: 81

Glu Val Met Xaa Val Ala Glu Phe
 1               5

<210> SEQ ID NO 82
<211> LENGTH: 9
<212> TYPE: PRT
<213> ORGANISM: Homo sapiens
<220> FEATURE:
<223> OTHER INFORMATION: APP fragment P5-P4' wt

<400> SEQUENCE: 82

Ser Glu Val Lys Met Asp Ala Glu Phe
 1               5

<210> SEQ ID NO 83
<211> LENGTH: 9
<212> TYPE: PRT
<213> ORGANISM: Homo sapiens
<220> FEATURE:
<223> OTHER INFORMATION: APP fragment P5-P4'wt
```

-continued

<400> SEQUENCE: 83

Ser Glu Val Asn Leu Asp Ala Glu Phe
1               5

<210> SEQ ID NO 84
<211> LENGTH: 9
<212> TYPE: PRT
<213> ORGANISM: Artificial Sequence
<220> FEATURE:
<223> OTHER INFORMATION: APP fragment

<400> SEQUENCE: 84

Ser Glu Val Lys Leu Asp Ala Glu Phe
1               5

<210> SEQ ID NO 85
<211> LENGTH: 9
<212> TYPE: PRT
<213> ORGANISM: Artificial Sequence
<220> FEATURE:
<223> OTHER INFORMATION: APP fragment

<400> SEQUENCE: 85

Ser Glu Val Lys Phe Asp Ala Glu Phe
1               5

<210> SEQ ID NO 86
<211> LENGTH: 9
<212> TYPE: PRT
<213> ORGANISM: Artificial Sequence
<220> FEATURE:
<223> OTHER INFORMATION: APP fragment

<400> SEQUENCE: 86

Ser Glu Val Asn Phe Asp Ala Glu Phe
1               5

<210> SEQ ID NO 87
<211> LENGTH: 9
<212> TYPE: PRT
<213> ORGANISM: Artificial Sequence
<220> FEATURE:
<223> OTHER INFORMATION: APP fragment

<400> SEQUENCE: 87

Ser Glu Val Lys Met Ala Ala Glu Phe
1               5

<210> SEQ ID NO 88
<211> LENGTH: 9
<212> TYPE: PRT
<213> ORGANISM: Artificial Sequence
<220> FEATURE:
<223> OTHER INFORMATION: APP fragment

<400> SEQUENCE: 88

Ser Glu Val Asn Leu Ala Ala Glu Phe
1               5

<210> SEQ ID NO 89
<211> LENGTH: 9
<212> TYPE: PRT
<213> ORGANISM: Artificial Sequence
<220> FEATURE:
<223> OTHER INFORMATION: APP fragment

```
<400> SEQUENCE: 89

Ser Glu Val Lys Leu Ala Ala Glu Phe
1               5

<210> SEQ ID NO 90
<211> LENGTH: 9
<212> TYPE: PRT
<213> ORGANISM: Artificial Sequence
<220> FEATURE:
<223> OTHER INFORMATION: APP fragment

<400> SEQUENCE: 90

Ser Glu Val Lys Met Leu Ala Glu Phe
1               5

<210> SEQ ID NO 91
<211> LENGTH: 9
<212> TYPE: PRT
<213> ORGANISM: Artificial Sequence
<220> FEATURE:
<223> OTHER INFORMATION: APP fragment

<400> SEQUENCE: 91

Ser Glu Val Asn Leu Leu Ala Glu Phe
1               5

<210> SEQ ID NO 92
<211> LENGTH: 9
<212> TYPE: PRT
<213> ORGANISM: Artificial Sequence
<220> FEATURE:
<223> OTHER INFORMATION: APP fragment

<400> SEQUENCE: 92

Ser Glu Val Lys Leu Leu Ala Glu Phe
1               5

<210> SEQ ID NO 93
<211> LENGTH: 9
<212> TYPE: PRT
<213> ORGANISM: Artificial Sequence
<220> FEATURE:
<223> OTHER INFORMATION: APP fragment

<400> SEQUENCE: 93

Ser Glu Val Lys Phe Ala Ala Glu Phe
1               5

<210> SEQ ID NO 94
<211> LENGTH: 9
<212> TYPE: PRT
<213> ORGANISM: Artificial Sequence
<220> FEATURE:
<223> OTHER INFORMATION: APP fragment

<400> SEQUENCE: 94

Ser Glu Val Asn Phe Ala Ala Glu Phe
1               5

<210> SEQ ID NO 95
<211> LENGTH: 9
<212> TYPE: PRT
<213> ORGANISM: Artificial Sequence
<220> FEATURE:
<223> OTHER INFORMATION: APP fragment

<400> SEQUENCE: 95
```

Ser Glu Val Lys Phe Leu Ala Glu Phe
1               5

<210> SEQ ID NO 96
<211> LENGTH: 9
<212> TYPE: PRT
<213> ORGANISM: Artificial Sequence
<220> FEATURE:
<223> OTHER INFORMATION: APP fragment

<400> SEQUENCE: 96

Ser Glu Val Asn Phe Leu Ala Glu Phe
1               5

<210> SEQ ID NO 97
<211> LENGTH: 14
<212> TYPE: PRT
<213> ORGANISM: Artificial Sequence
<220> FEATURE:
<223> OTHER INFORMATION: APP-derived fragment P10-P4'(D-V)

<400> SEQUENCE: 97

Lys Thr Glu Glu Ile Ser Glu Val Asn Leu Val Ala Glu Phe
1               5                   10

<210> SEQ ID NO 98
<211> LENGTH: 35
<212> TYPE: DNA
<213> ORGANISM: Homo sapiens

<400> SEQUENCE: 98
cccgaagagc ccggccggag gggcagcttt gtcga                               35

<210> SEQ ID NO 99
<211> LENGTH: 11
<212> TYPE: PRT
<213> ORGANISM: Homo sapiens

<400> SEQUENCE: 99

Glu Thr Asp Glu Glu Pro Glu Glu Pro Gly Arg
1               5                   10

<210> SEQ ID NO 100
<211> LENGTH: 10
<212> TYPE: PRT
<213> ORGANISM: Artificial Sequence
<220> FEATURE:
<223> OTHER INFORMATION: Recombinant 293T cells

<400> SEQUENCE: 100

Thr Gln His Gly Ile Arg Leu Pro Leu Arg
1               5                   10

<210> SEQ ID NO 101
<211> LENGTH: 9
<212> TYPE: PRT
<213> ORGANISM: Artificial Sequence
<220> FEATURE:
<223> OTHER INFORMATION: Recombinant 293T cells

<400> SEQUENCE: 101

Met Val Asp Asn Leu Arg Gly Lys Ser
1               5

<210> SEQ ID NO 102

```
-continued

<211> LENGTH: 10
<212> TYPE: PRT
<213> ORGANISM: Artificial Sequence
<220> FEATURE:
<223> OTHER INFORMATION: Recombinant CosA2 cells

<400> SEQUENCE: 102

Gly Ser Phe Val Glu Met Val Asp Asn Leu
 1               5                  10

<210> SEQ ID NO 103
<211> LENGTH: 4
<212> TYPE: PRT
<213> ORGANISM: Artificial Sequence
<220> FEATURE:
<223> OTHER INFORMATION: APP substrate fragment:WT Sequence

<400> SEQUENCE: 103

Val Lys Met Asp
 1

<210> SEQ ID NO 104
<211> LENGTH: 4
<212> TYPE: PRT
<213> ORGANISM: Artificial Sequence
<220> FEATURE:
<223> OTHER INFORMATION: APP substrate fragment:Swedish Sequence

<400> SEQUENCE: 104

Val Asn Leu Asp
 1
```